US012767651B2

(12) United States Patent
Bhujade et al.

(10) Patent No.: US 12,767,651 B2
(45) Date of Patent: Oct. 20, 2026

(54) OXADIAZOLE COMPOUNDS CONTAINING 5-MEMBERED HETEROAROMATIC RING FOR CONTROLLING OR PREVENTING PHYTOPATHOGENIC FUNGI

(71) Applicant: PI INDUSTRIES LTD., Udaipur-Rajasthan (IN)

(72) Inventors: Paras Raybhan Bhujade, Ahmednagar-Maharashtra (IN); Maruti N. Naik, Bhatkal-Karnataka (IN); Shantanu Ganesh Kulkarni, Ahmednagar-Maharashtra (IN); Rohit Arvind Dengale, Ahmednagar-Maharashtra (IN); Vinod Sunil Waghmare, Pune-Maharashtra (IN); Sonali Swarnkar, Chittorgarh-Rajasthan (IN); Nitin Ramesh Tembhare, Gondia-Maharashtra (IN); Santosh Shridhar Autkar, Akola-Maharashtra (IN); Ruchi Garg, Varanasi-Uttar Pradesh (IN); Vishwanath Gade, Thane West-Maharashtra (IN); Alexander G.M. Klausener, Pulheim (DE)

(73) Assignee: PI INDUSTRIES LTD., Udaipur-Rajasthan (IN)

(*) Notice: Subject to any disclaimer, the term of this patent is extended or adjusted under 35 U.S.C. 154(b) by 1283 days.

(21) Appl. No.: 17/753,065

(22) PCT Filed: Aug. 18, 2020

(86) PCT No.: PCT/IB2020/057756

§ 371 (c)(1),
(2) Date: Feb. 17, 2022

(87) PCT Pub. No.: WO2021/033133

PCT Pub. Date: Feb. 25, 2021

(65) Prior Publication Data

US 2022/0348567 A1 Nov. 3, 2022

(30) Foreign Application Priority Data

Aug. 19, 2019 (IN) ............................ 201911033375

(51) Int. Cl.
*C07D 413/10* (2006.01)
*A01N 43/82* (2006.01)

(52) U.S. Cl.
CPC ........... *C07D 413/10* (2013.01); *A01N 43/82* (2013.01)

(58) Field of Classification Search
CPC ..................................................... A01N 43/82
See application file for complete search history.

(56) References Cited

U.S. PATENT DOCUMENTS

| | | | | |
|---|---|---|---|---|
| 3,296,272 | A | 1/1967 | Johnston | |
| 3,325,503 | A | 6/1967 | Bimber | |
| 2004/0110749 | A1 | 6/2004 | Masao | |
| 2020/0190076 | A1 * | 6/2020 | Hoffman | C07D 417/10 |

FOREIGN PATENT DOCUMENTS

| | | | |
|---|---|---|---|
| DE | 19650197 | A1 | 6/1998 |
| DE | 10021412 | A1 | 6/2001 |
| DE | 10-2005-009458 | A1 | 9/2006 |
| EP | 0 141 317 | A2 | 5/1985 |
| EP | 0 152 031 | A2 | 8/1985 |
| EP | 0 226 917 | A1 | 7/1987 |
| EP | 0 243 970 | A1 | 11/1987 |
| EP | 0 256 503 | A2 | 2/1988 |
| EP | 0 374 753 | A2 | 6/1990 |
| EP | 0 392 225 | A2 | 10/1990 |
| EP | 0 427 529 | A1 | 5/1991 |
| EP | 0 428 941 | A1 | 5/1991 |
| EP | 0 451 878 | A1 | 10/1991 |
| EP | 0 532 022 | A1 | 3/1993 |
| EP | 1 028 125 | A1 | 8/2000 |
| EP | 1 035 122 | A1 | 9/2000 |
| EP | 1 122 244 | A1 | 8/2001 |
| EP | 1 201 648 | A1 | 5/2002 |
| EP | 3 165 093 | A1 | 5/2017 |
| JP | 2002-316902 | A | 10/2002 |
| WO | 93/07278 | A1 | 4/1993 |
| WO | 95/34656 | A1 | 12/1995 |
| WO | 98/46608 | A1 | 10/1998 |
| WO | 99/14187 | A1 | 3/1999 |
| WO | 99/24413 | A2 | 5/1999 |
| WO | 99/27783 | A1 | 6/1999 |
| WO | 00/29404 | A1 | 5/2000 |
| WO | 00/46148 | A1 | 8/2000 |
| WO | 00/65913 | A1 | 11/2000 |
| WO | 01/54501 | A2 | 8/2001 |
| WO | 01/56358 | A2 | 8/2001 |
| WO | 02/15701 | A2 | 2/2002 |
| WO | 02/22583 | A2 | 3/2002 |

(Continued)

*Primary Examiner* — Jeffrey S Lundgren
*Assistant Examiner* — Eric Tran
(74) *Attorney, Agent, or Firm* — Lippes Mathias LLP

(57) ABSTRACT

The present invention relates to a compound of formula (I),

Formula (I)

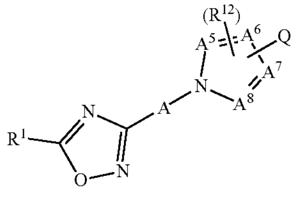

wherein, $R^1$, A, $A^5$, $A^6$, $A^7$, $A^8$, $R^{12}$, n and Q are as defined in the detailed description and a process for preparing the compound of formula (I). The present invention also relates to a method for controlling or preventing phytopathogenic fungi.

7 Claims, No Drawings

(56) References Cited

FOREIGN PATENT DOCUMENTS

| | | | | | |
|---|---|---|---|---|---|
| WO | 02/40431 | A2 | | 5/2002 | |
| WO | 03/010149 | A1 | | 2/2003 | |
| WO | 03/011853 | A1 | | 2/2003 | |
| WO | 03/014103 | A1 | | 2/2003 | |
| WO | 03/016286 | A1 | | 2/2003 | |
| WO | 03/016303 | A1 | | 2/2003 | |
| WO | 03/018810 | A2 | | 3/2003 | |
| WO | 03/052073 | A2 | | 6/2003 | |
| WO | 03/053145 | A1 | | 7/2003 | |
| WO | 03/061388 | A1 | | 7/2003 | |
| WO | 03/066609 | A1 | | 8/2003 | |
| WO | 03/074491 | A1 | | 9/2003 | |
| WO | 2004/049804 | A2 | | 6/2004 | |
| WO | 2004/083193 | A1 | | 9/2004 | |
| WO | 2005/063721 | A1 | | 7/2005 | |
| WO | 2005/087772 | A1 | | 9/2005 | |
| WO | 2005/087773 | A1 | | 9/2005 | |
| WO | 2005/120234 | A2 | | 12/2005 | |
| WO | 2005/123689 | A1 | | 12/2005 | |
| WO | 2005/123690 | A1 | | 12/2005 | |
| WO | 2006/002099 | A2 | | 1/2006 | |
| WO | 2006/015866 | A1 | | 2/2006 | |
| WO | 2006/071940 | A2 | | 7/2006 | |
| WO | 2006/087325 | A1 | | 8/2006 | |
| WO | 2006/087343 | A1 | | 8/2006 | |
| WO | 2007/006670 | A1 | | 1/2007 | |
| WO | 2007/082098 | A2 | | 7/2007 | |
| WO | 2007/090624 | A2 | | 8/2007 | |
| WO | 2008/138876 | A1 | | 11/2008 | |
| WO | 2009/090181 | A2 | | 7/2009 | |
| WO | 2010/069882 | A1 | | 6/2010 | |
| WO | 2011/028657 | A1 | | 3/2011 | |
| WO | 2011/077514 | A1 | | 6/2011 | |
| WO | 2011/135833 | A1 | | 11/2011 | |
| WO | 2012/168188 | A1 | | 12/2012 | |
| WO | 2013/007767 | A1 | | 1/2013 | |
| WO | 2013/010862 | A1 | | 1/2013 | |
| WO | 2013/024009 | A1 | | 2/2013 | |
| WO | 2013/024010 | A1 | | 2/2013 | |
| WO | 2013/047441 | A1 | | 4/2013 | |
| WO | 2013/047749 | A1 | | 4/2013 | |
| WO | 2013/092224 | A1 | | 6/2013 | |
| WO | 2013/127704 | A1 | | 9/2013 | |
| WO | 2013/162072 | A1 | | 10/2013 | |
| WO | 2015/185485 | A1 | | 12/2015 | |
| WO | 2017/076740 | A1 | | 5/2017 | |
| WO | 2017/093019 | A1 | | 6/2017 | |
| WO | 2017/093348 | A1 | | 6/2017 | |
| WO | 2017/118689 | A1 | | 7/2017 | |
| WO | WO-2017162868 | A1 | * | 9/2017 | ............ A01N 25/28 |
| WO | 2017/220485 | A1 | | 12/2017 | |
| WO | 2018/118781 | A1 | | 6/2018 | |
| WO | 2018/158365 | A1 | | 9/2018 | |
| WO | 2018/184970 | A1 | | 10/2018 | |
| WO | 2018/187553 | A1 | | 10/2018 | |
| WO | 2018/202491 | A1 | | 11/2018 | |
| WO | 2019/011923 | A1 | | 1/2019 | |
| WO | 2019/011926 | A1 | | 1/2019 | |
| WO | 2019/011928 | A1 | | 1/2019 | |
| WO | 2019/011929 | A1 | | 1/2019 | |
| WO | 2019/012001 | A1 | | 1/2019 | |
| WO | 2019/012003 | A1 | | 1/2019 | |
| WO | 2019/012011 | A1 | | 1/2019 | |

* cited by examiner

OXADIAZOLE COMPOUNDS CONTAINING 5-MEMBERED HETEROAROMATIC RING FOR CONTROLLING OR PREVENTING PHYTOPATHOGENIC FUNGI

This application is a National Stage Entry of International Application No. PCT/IB2020/057756, filed Aug. 18, 2020, and entitled "NOVEL OXADIAZOLE COMPOUNDS CONTAINING 5-MEMBERED HETEROAROMATIC RING FOR CONTROLLING OR PREVENTING PHYTOPATHOGENIC FUNGI;" which claims priority to Indian Application No. 201911033375, filed Aug. 19, 2019, and entitled "NOVEL OXADIAZOLE COMPOUNDS CONTAINING 5-MEMBERED HETEROAROMATIC RING FOR CONTROLLING OR PREVENTING PHYTOPATHOGENIC FUNGI," the contents of which are incorporated by reference herein.

FIELD OF THE INVENTION

The present invention relates to novel oxadiazole compounds that are useful in combating phytopathogenic fungi, a process for preparing oxadiazoles, a combination and a composition comprising novel oxadiazoles. The present invention also relates to a method for controlling or preventing phytopathogenic fungi.

BACKGROUND OF THE INVENTION

Oxadiazoles have already been disclosed in the literature. For example in EP3165093, WO2017076740, WO2017093019, WO2017093348, WO2017118689, WO2017162868, WO2017220485, WO2018118781, WO2018158365, WO2018184970, WO2018187553, WO2018202491, WO2019011923, WO2019012003, WO2019011926, WO2019011928, WO2019011929, WO2019012001 and WO2019012011 various oxadiazoles have been disclosed.

The oxadiazole compounds reported in the above cited literature have disadvantages in certain aspects, such as that they exhibit a narrow spectrum of efficacy or that they do not have satisfactory fungicidal activity, particularly at low application rates.

Therefore, it is an object of the present invention to provide compounds having an improved/enhanced activity and/or a broader efficacy spectrum against phytopathogenic fungi.

This objective is achieved by using a compound of formula (I) of the present invention for controlling or preventing phytopathogenic fungi.

SUMMARY OF THE INVENTION

The present invention relates to a compound of formula (I),

Formula (I)

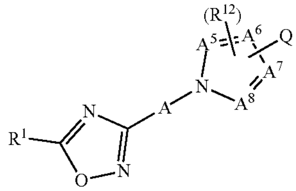

wherein, $R^1$, A, $A^5$, $A^6$, $A^7$, $A^8$, $R^{12}$, n and Q are as defined in the detailed description. The present invention also relates to a process for preparing the compound of formula (I).

The compounds of formula (I) have been found to be advantageous over the compounds reported in the literature in either of improved fungicidal activity, broader spectrum of biological efficacy, lower application rates, more favourable biological, environmental properties or enhanced plant compatibility.

The present invention further relates to a combination comprising the compound of formula (I) of the present invention and at least one further pesticidally active substance for effectively controlling or preventing phytopathogenic fungi which are difficult to combat.

The present invention still further relates to anagrochemical composition comprising the compound of formula (I) as such or the compound of formula (I) in combination with a further pesticidally active substance.

The present invention still further relates to a method and use of the compound of formula (I) as such or the combination or the composition thereof for controlling and or preventing plant diseases, particularly phtopathogenic fungi.

DETAILED DESCRIPTION OF THE INVENTION

Definitions:

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e.

occurrences) of the element or component. Therefore “a” or “an” should be read to include one or at least one, and the singular word form of the element or component also includes the plural unless the number is obviously meant to be singular.

As referred to in this disclosure, the term “invertebrate pest” includes arthropods, gastropods and nematodes and helminths of economic importance as pests. The term “arthropod” includes insects, mites, spiders, scorpions, centipedes, millipedes, pill bugs and symphylans. The term “gastropod” includes snails, slugs and other Stylommatophora. The term “nematode” refers to a living organism of the Phylum Nematoda. The term “helminths” includes roundworms, heartworms, phytophagous nematodes (Nematoda), flukes (Tematoda), acanthocephala and tapeworms (Cestoda).

In the context of this disclosure “invertebrate pest control” means inhibition of invertebrate pest development (including mortality, feeding reduction, and/or mating disruption), and related expressions are defined analogously.

The term “agronomic” refers to the production of field crops such as for food, feed and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term “nonagronomic” refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the present invention, typically in the form of a composition formulated for veterinary use, to the animal to be protected. As referred to in the present disclosure and claims, the terms “parasiticidal” and “parasiticidally” refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

Compounds of the present disclosure may be present either in pure form or as mixtures of different possible isomeric forms such as stereoisomers or constitutional isomers. The various stereoisomers include enantiomers, diastereomers, chiral isomers, atropisomers, conformers, rotamers, tautomers, optical isomers, polymorphs, and geometric isomers. Any desired mixtures of these isomers fall within the scope of the claims of the present disclosure. One skilled in the art will appreciate that one stereoisomer may be more active and/or may exhibit beneficial effects when enriched relative to the other isomer(s) or when separated from the other isomer(s). Additionally, the person skilled in the art knows processes or methods or technology to separate, enrich, and/or to selectively prepare said isomers.

The meaning of various terms used in the description shall now be illustrated.

The term “alkyl”, used either alone or in compound words such as “alkylthio” or “haloalkyl” or —N(alkyl) or alkylcarbonylalkyl or alkylsuphonylamino includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Non-limiting examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxy, halogen, carbonyl, carbonyloxy and the like, are at the end.

The term “alkenyl”, used either alone or in compound words includes straight-chain or branched $C_2$ to $C_{24}$ alkenes, preferably $C_2$ to $C_{15}$ alkenes, more preferably $C_2$ to $C_{10}$ alkenes, most preferably $C_2$ to $C_6$ alkenes. Non-limiting examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. “Alkenyl” also includes polyenes such as 1,2-propadienyl and 2,4-hexadienyl. This definition also applies to alkenyl as a part of a composite substituent, for example haloalkenyl and the like, unless defined specifically elsewhere.

Non-limiting examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl and the different isomers. This definition also applies to alkynyl as a part of a composite substituent, for example haloalkynyl etc., unless specifically defined elsewhere. The term "alkynyl" can also include moieties comprised of multiple triple bonds such as 2,5-hexadiynyl.

The term "cycloalkyl" means alkyl closed to form a ring. Non-limiting examples include cyclopropyl, cyclopentyl and cyclohexyl. This definition also applies to cycloalkyl as a part of a composite substituent, for example cycloalkylalkyl etc., unless specifically defined elsewhere.

The term "cycloalkenyl" means alkenyl closed to form a ring including monocyclic, partially unsaturated hydrocarbyl groups. Non-limiting examples include cyclopropenyl, cyclopentenyl and cyclohexenyl. This definition also applies to cycloalkenyl as a part of a composite substituent, for example cycloalkenylalkyl etc., unless specifically defined elsewhere.

The term "cycloalkynyl" means alkynyl closed to form a ring including monocyclic, partially unsaturated groups. Non-limiting examples include cyclopropynyl, cyclopentynyl and cyclohexynyl. This definition also applies to cycloalkynyl as a part of a composite substituent, for example cycloalkynylalkyl etc., unless specifically defined elsewhere.

The term "cycloalkoxy", "cycloalkenyloxy" and the like are defined analogously. Non limiting examples of cycloalkoxy include cyclopropyloxy, cyclopentyloxy and cyclohexyloxy. This definition also applies to cycloalkoxy as a part of a composite substituent, for example cycloalkoxy alkyl etc., unless specifically defined elsewhere.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms "haloalkenyl", "haloalkynyl" are defined analogously except that, instead of alkyl groups, alkenyl and alkynyl groups are present as a part of the substituent.

The term "haloalkoxy" means straight-chain or branched alkoxy groups where some or all of the hydrogen atoms in these groups may be replaced by halogen atoms as specified above. Non-limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term "haloalkylthio" means straight-chain or branched alkylthio groups where some or all of the hydrogen atoms in these groups may be replaced by halogen atoms as specified above. Non-limiting examples of haloalkylthio include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as a part of a composite substituent, for example haloalkylthioalkyl etc., unless specifically defined elsewhere.

Non-limiting examples of "haloalkylsulfinyl" include $CF_3S(O)$, $CCl_3S(O)$, $CF_3CH_2S(O)$ and $CF_3CF_2S(O)$. Non-limiting examples of "haloalkylsulfonyl" include $CF_3S(O)_2$, $CCl_3S(O)_2$, $CF_3CH_2S(O)_2$ and $CF_3CF_2S(O)_2$.

The term "hydroxy" means —OH, Amino means —NRR, wherein R can be H or any possible substituent such as alkyl. Carbonyl means —C(=O)—, carbonyloxy means —OC(=O)—, sulfinyl means SO, sulfonyl means $S(O)_2$.

The term "alkoxy" used either alone or in compound words included $C_1$ to $C_{24}$ alkoxy, preferably $C_1$ to $C_{15}$ alkoxy, more preferably $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "alkoxyalkyl" denotes alkoxy substitution on alkyl. Non-limiting examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

The term "alkoxyalkoxy" denotes alkoxy substitution on alkoxy.

The term "alkylthio" includes branched or straight-chain alkylthio moieties such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio and the different isomers.

Halocycloalkyl, halocycloalkenyl, alkylcycloalkyl, cycloalkylalkyl, cycloalkoxyalkyl, alkylsulfinylalkyl, alkylsulfonylalkyl, haloalkylcarbonyl, cycloalkylcarbonyl, haloalkoxylalkyl, and the like, are defined analogously to the above examples.

The term "alkylthioalkyl" denotes alkylthio substitution on alkyl. Non-limiting examples of "alkylthioalkyl" include $—CH_2SCH_2$, $—CH_2SCH_2CH_2$, $CH_3CH_2SCH_2$, $CH_3CH_2CH_2CH_2SCH_2$ and $CH_3CH_2SCH_2CH_2$. "Alkylthioalkoxy" denotes alkylthio substitution on alkoxy. The term "cycloalkylalkylamino" denotes cycloalkyl substitution on alkyl amino.

The terms "alkoxyalkoxyalkyl", "alkylaminoalkyl", "dialkylaminoalkyl", "cycloalkylaminoalkyl", "cycloalkylaminocarbonyl" and the like, are defined analogously to "alkylthioalkyl" or "cycloalkylalkylamino".

The term "alkoxycarbonyl" is an alkoxy group bonded to a skeleton via a carbonyl group (—CO—). This definition also applies to alkoxycarbonyl as a part of a composite substituent, for example cycloalkylalkoxycarbonyl and the like, unless specifically defined elsewhere.

The term "alkoxycarbonylalkylamino" denotes alkoxy carbonyl substitution on alkyl amino. "Alkylcarbonylalkylamino" denotes alkyl carbonyl substitution on alkyl amino. The terms alkylthioalkoxycarbonyl, cycloalkylalkylaminoalkyl and the like are defined analogously.

Non-limiting examples of "alkylsulfinyl" include methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl and the different isomers. The term "arylsulfinyl" includes Ar—S(O), wherein Ar can be any carbocyle or heterocylcle. This definition also applies to alkylsulphinyl as a part of a composite substituent, for example haloalkylsulphinyl etc., unless specifically defined elsewhere.

Non-limiting examples of "alkylsulfonyl" include methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl and the different isomers. The term "arylsulfonyl" includes Ar—$S(O)_2$, wherein Ar can be any carbocyle or heterocylcle. This definition also applies to alkylsulphonyl as a part of a composite substituent, for example alkylsulphonylalkyl etc., unless defined elsewhere.

"Alkylamino", "dialkylamino", and the like, are defined analogously to the above examples.

The term "carbocycle or carbocyclic" includes "aromatic carbocyclic ring system" and "non-aromatic carbocylic ring system" or polycyclic or bicyclic (spiro, fused, bridged, nonfused) ring compounds in which ring may be aromatic or non-aromatic (where aromatic indicates that the Huckel rule is satisfied and non-aromatic indicates that the Huckel rule is not satisfied).

The term "heterocycle or heterocyclic" includes "aromatic heterocycle or heteroaryl ring system" and "non-aromatic heterocycle ring system" or polycyclic or bicyclic (spiro, fused, bridged, nonfused) ring compounds in which ring may be aromatic or non-aromatic, wherein the heterocycle ring contains at least one heteroatom selected from N, O, $S(O)_{0-2}$, and or C ring member of the heterocycle may be replaced by C(═O), C(═S), C(═CR*R*) and C═NR*, *indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; non-limiting examples oxetanyl, oxiranyl, aziridinyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-1-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, pyrrolinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidinyl, 2-piperidinyl, 3-piperidinyl, 4-piperidinyl, pyrazynyl, morpholinyl, thiomorphlinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, cycloserines, 2,3,4,5-tetrahydro[1H]azepin-1- or -2- or -3- or -4- or -5- or -6- or -7-yl, 3,4,5,6-tetra-hydro[2H]azepin-2- or -3- or -4- or -5- or -6- or -7-yl, 2,3,4,7-tetrahydro[1H]azepin-1- or -2- or -3- or -4- or -5- or -6- or -7-yl, 2,3,6,7-tetrahydro[1H]azepin-1- or -2- or -3- or -4- or -5- or -6- or -7-yl, hexahydroazepin-1- or -2- or -3- or -4-yl, tetra- and hexahydrooxepinyl such as 2,3,4,5-tetrahydro[1H]oxepin-2- or -3- or -4- or -5- or -6- or -7-yl, 2,3,4,7-tetrahydro[1H]oxepin-2- or -3- or -4- or -5- or -6- or -7-yl, 2,3,6,7-tetrahydro[1H]oxepin-2- or -3- or -4- or -5- or -6- or -7-yl, hexahydroazepin-1- or -2- or -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl. This definition also applies to heterocyclyl as a part of a composite substituent, for example heterocyclylalkyl etc., unless specifically defined elsewhere.

The term "heteroaryl" or "aromatic heterocyclic" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom; 5-membered heteroaryl groups which, in addition to carbon atoms, may contain one to four nitrogen atoms or one to three nitrogen atoms and one sulphur or oxygen atom as ring members, non-limiting examples furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, non-limiting examples 1-pyrrolyl, 1-pyrazolyl, 1,2,4-triazol-1-yl, 1-imidazolyl, 1,2,3-triazol-1-yl and 1,3,4-triazol-1-yl.

6-membered heteroaryl which contains one to four nitrogen atoms: 6-membered heteroaryl groups which, in addition to carbon atoms, may contain, respectively, one to three and one to four nitrogen atoms as ring members, non-limiting examples 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl; benzofused 5-membered heteroaryl containing one to three nitrogen atoms or one nitrogen atom and one oxygen or sulphur atom: non-limiting examples indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl; benzofused 6-membered heteroaryl which contains one to three nitrogen atoms: non-limiting examples quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

The term "trialkylsilyl" includes 3 branched and/or straight-chain alkyl radicals attached to and linked through a silicon atom such as trimethylsilyl, triethylsilyl and t-butyl-dimethylsilyl. "Halotrialkylsilyl" denotes at least one of the three alkyl radicals is partially or fully substituted with halogen atoms which may be the same or different. The term"alkoxytrialkylsilyl" denotes at least one of the three alkyl radicals is substituted with one or more alkoxy radicals which may be the same or different. The term "trialkylsilyloxy" denotes a trialkylsilyl moiety attached through oxygen.

Non-limiting examples of "alkylcarbonyl" include $C(=O)CH_3$, $C(=O)CH_2CH_2CH_3$ and $C(=O)CH(CH_3)_2$. Non-limiting examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Non-limiting examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Non-limiting examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH_3)C(=O)$. Non-limiting examples of "alkoxyalkylcarbonyl" include $CH_3OCH_2C(=O)$, $CH_3OCH_2CH_2C(=O)$, $CH_3CH_2OCH_2C(=O)$, $CH_3CH_2CH_2CH_2OCH_2C(=O)$ and $CH_3CH_2OCH_2CH_2C(=O)$. Non-limiting examples of "alkylthioalkylcarbonyl" include $CH_3SCH_2C(=O)$, $CH_3SCH_2CH_2C(=O)$, $CH_3CH_2SCH_2C(=O)$, $CH_3CH_2CH_2CH_2SCH_2C(=O)$ and $CH_3CH_2SCH_2CH_2C(=O)$. The term haloalkylsufonylaminocarbonyl, alkylsulfonylaminocarbonyl, alkylthioalkoxycarbonyl, alkoxycarbonylalkyl amino and the like are defined analogously Non-limiting examples of "alkylaminoalkylcarbonyl" include $CH_3NHCH_2C(=O)$, $CH_3NHCH_2CH_2C(=O)$, $CH_3CH_2NHCH_2C(=O)$, $CH_3CH_2CH_2CH_2NHCH_2C(=O)$ and $CH_3CH_2NHCH_2CH_2C(=O)$.

The term "amide" means A-R'C=ONR"—B, wherein R' and R" indicates substituents and A and B indicate any group.

The term "thioamide" means A-R'C=SNR"—B, wherein R' and R" indicates substituents and A and B indicate any group.

The total number of carbon atoms in a substituent group is indicated by the "$C_i$-$C_j$" prefix where i and j are numbers from 1 to 21. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula (I) is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript m in $(R)_m$ indicates an integer ranging from for example 0 to 4 then the number of substituents may be selected from the integers between 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the description/claims though might form a critical part of the present invention of the present invention, any deviation from such numerical values shall still fall within the scope of the present invention if that deviation follows the same scientific principle as that of the present invention disclosed in the present invention.

The inventive compound of the present invention may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

The term "pest" for the purpose of the present disclosure includes but is not limited to fungi, stramenopiles (oomycetes), bacteria, nematodes, mites, ticks, insects and rodents.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis.

Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; cucurbitaceae; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention includes but is not limited to cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground. For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxillary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which include but is not limited to spraying, coating, dipping, fumigating, impregnating, injecting and dusting.

The term “applied” means adhered to a plant or plant part either physically or chemically including impregnation.

Accordingly, the present invention provides a novel oxadiazole compound formula (I), Formula (I)

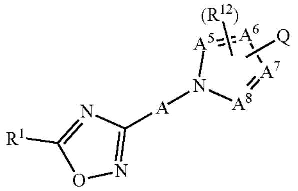

wherein, $R^1$ is $C_1$-$C_2$-haloalkyl;

A is

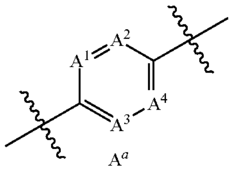

$A^a$ or

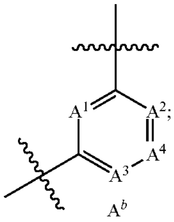

$A^b$ $A^1$, $A^2$, $A^3$ and $A^4$ are independently selected from $CR^9$ or N;

$A^5$, $A^6$, $A^7$ and $A^8$ are independently selected from C or N; provided that at least one of $A^5$, $A^6$, $A^7$ and $A^8$ is C;

$R^9$ and $R^{12}$ are independently selected from the group consisting of hydrogen, halogen, nitro, cyano, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ thioalkyl and $C_3$-$C_6$ cycloalkoxy;

two adjacent $R^9$ together with the C atom to which they are attached may form a 5- to 6-membered aromatic or non aromatic carbocyclic ring;

Q is selected from the group consisting of $Q_1$ to $Q_{12}$;

$Q_1$

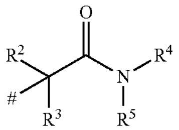

$Q_2$

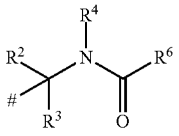

$Q_3$

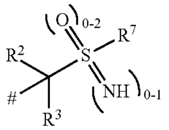

-continued $Q_4$

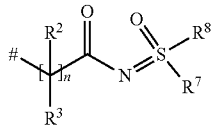

$Q_5$

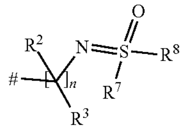

$Q_6$

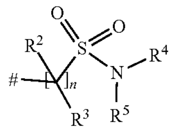

$Q_7$

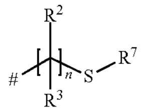

$Q_8$

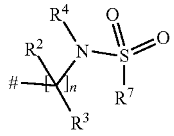

$Q_9$

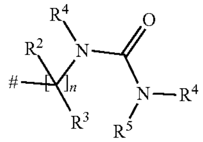

$Q_{10}$

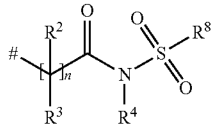

$Q_{11}$

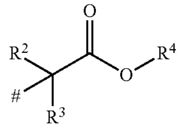

$Q_{12}$

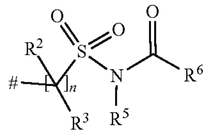

wherein, $R^2$ and $R^3$ are independently selected from the group consisting of hydrogen, halogen, $C_1$-$C_6$ alkyl, $C_1$-$C_6$ haloalkyl, $C_1$-$C_6$ alkoxy and $C_1$-$C_6$ haloalkoxy; or $R^2$ and $R^3$ together with the C atom to which they are attached may form a 3- to 6-membered nonaromatic carbocyclic ring or a 3- to 6-membered nonaromatic heterocyclic ring; wherein the hetero atom is selected from the group consisting of 0, S or N; C atom of said nonaromatic carbocyclic ring or said nonaromatic heterocyclic ring may be optionally substituted with C(═O) or C(═S); and said nonaromatic carbocyclic ring or said nonaromatic heterocyclic ring may be optionally substituted with halogen or $C_1$-$C_3$ alkyl or $C_1$-$C_3$-alkoxy;

$R^4$, $R^5$, $R^6$, $R^7$, and $R^8$ are independently selected from the group consisting of hydrogen, halogen, $C_1$-$C_6$alkyl, $C_2$-$C_6$-alkenyl, $C_2$-$C_6$-alkynyl, $C_3$-$C_6$cycloalkyl, $C_1$-$C_6$ alkoxy, $C_1$-$C_6$ haloalkyl, $C_3$-$C_6$cycloalkyl-$C_1$-$C_6$alkyl, $C_1$-$C_6$alkoxy-$C_1$-$C_6$alkyl, $C_1$-$C_6$ alkoxycarbonyl, $C_1$-$C_6$ alkylsulfinyl, $C_1$-$C_6$ alkylsulfonyl, —$(CR^{10}R^{11})_{0-4}C_3$-$C_6$ non-aromatic carbocyclyl ring, —$(CR^{10}R^{11})_{0-4}C_6$-$C_{10}$ aromatic carbocyclyl ring, —$(CR^{10}R^{11}))_{0-4}C_3$-$C_6$ non-aromatic heterocyclyl ring, —$(CR^{10}R^{11})_{0-4}C_6$-$C_{10}$ aromatic heterocyclyl ring, —$S(O)_{0-2}C_3$-$C_6$ non-aromatic carbocyclyl ring, —$S(O)_{0-2}C_6$-$C_{10}$ aromatic carbocyclyl ring, —$S(O)_{0-2}C_3$-$C_6$ non-aromatic heterocyclyl ring and —$S(O)_{0-2}C_6$-$C_{10}$ aromatic heterocyclyl ring; or $R^4$ and $R^5$, $R^8$ and $R^7$, $R^4$ and $R^6$, $R^5$ and $R^6$, $R^4$ and $R^7$ together the atom to which they are attached may represent 4- to 8-membered nonaromatic heterocyclic ring; wherein the hetero atom is selected from the group consisting of O, $S(=O)_{0-2}$ or $NR^{13}$; C atom of said nonaromatic heterocyclic ring may be optionally substituted with C(=O) or C(=S);

$R^4$, $R^5$, $R^6$, $R^7$, and $R^8$ are optionally and independently may be substituted with halogen, cyano, amino, $C_1$-$C_6$ alkyl, $C_1$-$C_6$ alkoxy, $C_1$-$C_6$haloalkoxy, $C_1$-$C_6$ haloalkyl, $C_3$-$C_6$ cycloalkyl, $C_3$-$C_6$cycloalkyloxy; $C_1$-$C_6$ alkylamino, $C_1$-$C_6$ dialkylamino and $C_1$-$C_6$ trialkylamino;

$R^{10}$, $R^{11}$, and $R^{13}$ are independently selected from the group consisting of hydrogen, halogen, $C_1$-$C_6$ alkyl, $C_3$-$C_6$ cycloalkyl, $C_1$-$C_6$ haloalkyl and $C_1$-$C_6$ alkoxy;

n is an integer selected from 0, 1, 2 or 3;

and/or N-oxides, metal complexes, isomers, polymorphs or the agriculturally acceptable salts thereof.

In preferred embodiment, the present invention provides compound of formula (I) wherein $R^1$ is selected from the group consisting of —$CF_3$, —$CHF_2$ and —$CF_2Cl$;

A is phenyl or pyridyl;

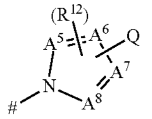

is selected from B1 to B5;

B1

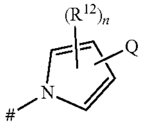

B2

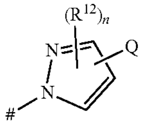

-continued

B3

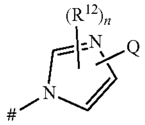

B4

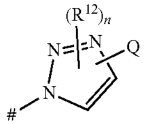

B5

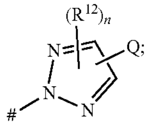

wherein, # represents attachment to A.

In one embodiment, the present invention provides a compound of formula (Ia),

Formla (Ia)

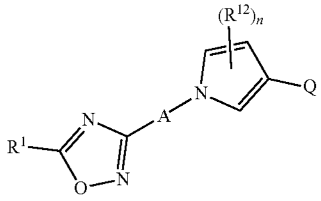

wherein, $R^1$ is $CF_3$; A, $R^{12}$, n and Q are as defined in the detailed description above.

In another embodiment, the present invention provides a compound of formula (Iaa), Formla (Iaa)

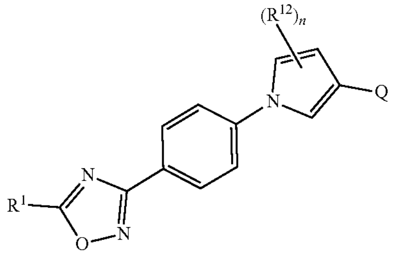

wherein, $R^1$ is $CF_3$; $R^{12}$, n and Q are as defined in the detailed description above.

In yet another embodiment, the present invention provides a compound of formula (Ib), Formla (Ib)

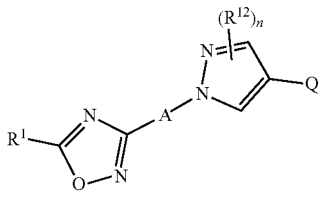

wherein, $R^1$ is $CF_3$; A, $R^{12}$, n and Q are as defined in the detailed description above.

In yet another embodiment, the present invention provides a compound of formula (Iba), Formla (Iba)

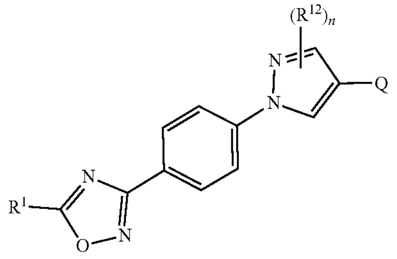

wherein, $R^1$ is $CF_3$; $R^{12}$, n and Q are as defined in the detailed description above.

In yet another embodiment, the present invention provides a compound of formula (Ic), Formla (Ic)

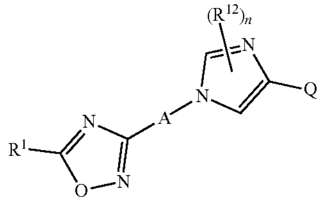

wherein, $R^1$ is $CF_3$; A, $R^{12}$, n and Q are as defined in the detailed description above.

In yet another embodiment, the present invention provides a compound of formula (Ica), Formla (Ica)

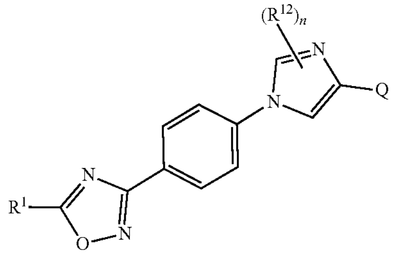

wherein, $R^1$ is $CF_3$; $R^{12}$, n and Q are as defined in the detailed description above.

In another preferred embodiment, the present invention provides compound of formula (I) is selected from ethyl 2-(1-(4-(5-(trifluoromethyl)-1,2,4-oxadiazol-3-yl)phenyl)-1H-imidazol-4-yl)acetate, N-(4-methoxyphenyl)-2-(1-(4-(5-(trifluoromethyl)-1,2,4-oxadiazol-3-yl)phenyl)-1H-imidazol-4-yl)acetamide, 1-(pyrrolidin-1-yl)-2-(1-(4-(5-(trifluoromethyl)-1,2,4-oxadiazol-3-yl)phenyl)-1H-imidazol-4-yl)ethan-1-one, N-benzyl-2-(1-(4-(5-(trifluoromethyl)-1,2,4-oxadiazol-3-yl)phenyl)-1H-imidazol-4-yl)acetamide, N-(4-methoxybenzyl)-2-(1-(4-(5-(trifluoromethyl)-1,2,4-oxadiazol-3-yl)phenyl)-1H-imidazol-4-yl)acetamide, N-(4-fluorobenzyl)-2-(1-(4-(5-(trifluoromethyl)-1,2,4-oxadiazol-3-yl)phenyl)-1H-imidazol-4-yl)acetamide, N-(2-fluorobenzyl)-2-(1-(4-(5-(trifluoromethyl)-1,2,4-oxadiazol-3-yl)phenyl)-1H-imidazol-4-yl)acetamide, N-(p-tolyl)-2-(1-(4-(5-(trifluoromethyl)-1,2,4-oxadiazol-3-yl)phenyl)-1H-imidazol-4-yl)acetamide, N-(4-chlorophenyl)-2-(1-(4-(5-(trifluoromethyl)-1,2,4-oxadiazol-3-yl)phenyl)-1H-imidazol-4-yl)acetamide, N-(3-fluorophenyl)-2-(1-(4-(5-(trifluoromethyl)-1,2,4-oxadiazol-3-yl)phenyl)-1H-imidazol-4-yl)acetamide, 1-(piperidin-1-yl)-2-(1-(4-(5-(trifluoromethyl)-1,2,4-oxadiazol-3-yl)phenyl)-1H-imidazol-4-yl)ethan-1-one, N-(3-methoxyphenyl)-2-(1-(4-(5-(trifluoromethyl)-1,2,4-oxadiazol-3-yl)phenyl)-1H-imidazol-4-yl)acetamide, N-(pyridin-3-yl)-2-(1-(4-(5-(trifluoromethyl)-1,2,4-oxadiazol-3-yl)phenyl)-1H-imidazol-4-yl)acetamide, N-(2-bromophenyl)-2-(1-(4-(5-(trifluoromethyl)-1,2,4-oxadiazol-3-yl)phenyl)-1H-imidazol-4-yl)acetamide, N-phenyl-2-(1-(4-(5-(trifluoromethyl)-1,2,4-oxadiazol-3-yl)phenyl)-1H-imidazol-4-yl)acetamide, N-(5-methoxy-2-methylphenyl)-2-(1-(4-(5-(trifluoromethyl)-1,2,4-oxadiazol-3-yl)phenyl)-1H-imidazol-4-yl)acetamide, N-(4-fluoro-2-methoxyphenyl)-2-(1-(4-(5-(trifluoromethyl)-1,2,4-oxadiazol-3-yl)phenyl)-1H-imidazol-4-yl)acetamide, N-(4-oxido-1,4-$\lambda^6$-oxathian-4-ylidene)-1-(4-(5-(trifluoromethyl)-1,2,4-oxadiazol-3-yl)phenyl)-1H-pyrazole-4-carboxamide, N-(methyl(oxo)(o-tolyl)-$\lambda^6$-sulfaneylidene)-1-(4-(5-(trifluoromethyl)-1,2,4-oxadiazol-3-yl)phenyl)-1H-pyrazole-4-carboxamide, N-((2-methoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-((4-methoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-(methyl(oxo)(phenyl)-$\lambda^6$-sulfaneylidene)-1-(4-(5-(trifluoromethyl)-1,2,4-oxadiazol-3-yl)phenyl)-1H-pyrazole-4-carboxamide, N-((3-fluorophenyl)(methyl)(oxo)-$\lambda^6$-sulfanylidene)-1-(4-(5-(trifluoromethyl)-1,2,4-oxadiazol-3-yl)phenyl)-1H-pyrazole-4-carboxamide, N-(methyl(oxo)(m-tolyl)-$\lambda^6$-sulfanylidene)-1-(4-(5-(trifluoromethyl)-1,2,4-oxadiazol-3-yl)phenyl)-1H-pyrrole-3-carboxamide, N-((2-methoxyethyl)(oxo)(pyridin-2-yl)-$\lambda^6$-sulfanylidene)-1-(4-(5-(trifluoromethyl)-1,2,4-oxadiazol-3-yl)phenyl)-1H-pyrrole-3-carboxamide, N-(methyl(oxo)(5-(trifluoromethyl)pyridin-2-yl)-$\lambda^6$-sulfanylidene)-1-(4-(5-(trifluoromethyl)-1,2,4-oxadiazol-3-yl)phenyl)-1H-pyrrole-3-carboxamide, N-((4-fluorophenyl)(methyl)(oxo)-$\lambda^6$-sulfanylidene)-1-(4-(5-(trifluoromethyl)-1,2,4-oxadiazol-3-yl)phenyl)-1H-pyrrole-3-carboxamid, N-((3-fluoropyridin-4-yl)(methyl)(oxo)-$\lambda^6$-sulfanylidene)-1-(4-(5-(trifluoromethyl)-1,2,4-oxadiazol-3-yl)phenyl)-1H-pyrrole-3-carboxamid, N-((4-methoxypyridin-2-yl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide, N-(dimethyl(oxo)-$\lambda^6$-sulfanylidene)-1-(4-(5-(trifluoromethyl)-1,2,4-oxadiazol-3-yl)phenyl)-1H-pyrrole-3-carboxamide, N-((4-methoxyphenyl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide, N-((2,4-dimethoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-((2,6-dichlorophenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-(methyl(oxo)(pyridin-4-yl)-$\lambda^6$-sulfaneylidene)-1-(4-(5-(trifluoromethyl)-1,2,4-oxadiazol-3-yl)phenyl)-1H-pyrazole-4-carboxamide, N-((2-methoxyethyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-(diethyl(oxo)-$\lambda^6$-sulfaneylidene)-1-(4-(5-(trifluoromethyl)-1,2,4-oxadiazol-3-yl)phenyl)-1H-pyrazole-4-carboxamide, N-(dimethyl(oxo)-$\lambda^6$-sulfaneylidene)-1-(4-(5-(trifluoromethyl)-1,2,4-oxadiazol-3-yl)phenyl)-1H-pyrazole-4-carboxamide, N-((4-chlorophenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-((3-bromophenyl)(isopropyl)(oxo)-$\lambda^6$-sulfanylidene)-1-(4-(5-(trifluoromethyl)-1,2,4-oxadiazol-3-yl)phenyl)-1H-pyrrole-3-carboxamide, N-(methyl(oxo)(thiazol-2-yl)-$\lambda^6$-sulfanylidene)-1-(4-(5-(trifluoromethyl)-1,2,4-oxadiazol-3-yl)phenyl)-1H-pyrrole-3-carboxamide, 3-(4-(4-(piperidin-1-ylsulfonyl)-1H-pyrazol-1-yl)phenyl)-5-(trifluoromethyl)-1,2,4-oxadiazole, 3-(4-(4-((phenylthio)methyl)-1H-imidazol-1-yl)phenyl)-5-(trifluoromethyl)-1,2,4-oxadiazole, tert-Butyl-2-(3,5-dimethyl-1-(4-(5-(trifluoromethyl)-1,2,4-oxadiazol-3-yl)phenyl)-1H-pyrazol-4-yl)acetate, N-(4-fluorophenyl)-1-(4-(5-(trifluoromethyl)-1,2,4-oxadiazol-3-yl)phenyl)-1H-pyrazole-4-sulfonamide, N-ethyl-1-(4-(5-(trifluoromethyl)-1,2,4-oxadiazol-3-yl)phenyl)-1H-pyrazole-4-sulfonamide, N-(2,4-difluorophenyl)-N-methyl-1-(4-(5-(trifluoromethyl)-1,2,4-oxadiazol-3-yl)phenyl)-1H-pyrazole-4-sulfonamide, N-(2-fluorophenyl)-N-methyl-1-(4-(5-(trifluoromethyl)-1,2,4-oxadiazol-3-yl)phenyl)-1H-pyrazole-4-sulfonamide, 3-(4-(4-(azetidin-1-ylsulfonyl)-1H-pyrazol-1-yl)phenyl)-5-(trifluoromethyl)-1,2,4-oxadiazole, N-methyl-N-phenyl-1-(4-(5-(trifluoromethyl)-1,2,4-oxadiazol-3-yl)phenyl)-1H-pyrazole-4-sulfonamide, N-(3-methoxyphenyl)-N-methyl-1-(4-(5-(trifluoromethyl)-1,2,4-oxadiazol-3-yl)phenyl)-1H-pyrazole-4-sulfonamide, N-methyl-N-(p-tolyl)-1-(4-(5-(trifluoromethyl)-1,2,4-oxadiazol-3-yl)phenyl)-1H-pyrazole-4-sulfonamide, N-(3-fluorophenyl)-N-methyl-1-(4-(5-(trifluoromethyl)-1,2,4-oxadiazol-3-yl)phenyl)-1H-pyrazole-4-sulfonamide, N-(3-chlorophenyl)-N-methyl-1-(4-(5-(trifluoromethyl)-1,2,4-oxadiazol-3-yl)phenyl)-1H-pyrazole-4-sulfonamide, 3-(4-(4-((3-fluoropyrrolidin-1-yl)sulfonyl)-1H-pyrazol-1-yl)phenyl)-5-(trifluoromethyl)-1,2,4-oxadiazole, N-methyl-N-(pyridin-2-yl)-1-(4-(5-(trifluoromethyl)-1,2,4-oxadiazol-3-yl)phenyl)-1H-pyrazole-4-sulfonamide, 4-((1-(4-(5-(trifluoromethyl)-1,2,4-oxadiazol-3-yl)phenyl)-1H-pyrazol-4-yl)sulfonyl)morpholine, N-cyclopropyl-1-(4-(5-(trifluoromethyl)-1,2,4-oxadiazol-3-yl)phenyl)-1H-pyrazole-4-sulfonamide, N-benzyl-1-(4-(5-(trifluoromethyl)-1,2,4-oxadiazol-3-yl)phenyl)-1H-pyrazole-4-sulfonamide, 3-(4-(4-(((4-methoxyphenyl)thio)methyl)-1H-imidazol-1-yl)phenyl)-5-(trifluoromethyl)-1,2,4-oxadiazole, 3-(4-(4-((isopropylthio)methyl)-1H-imidazol-1-yl)phenyl)-5-(trifluoromethyl)-1,2,4-oxadiazole, 3-(4-(4-(((2-fluorophenyl)thio)methyl)-1H-imidazol-1-yl)phenyl)-5-(trifluoromethyl)-1,2,4-oxadiazole, 3-(4-(4-(((4-fluorophenyl)thio)methyl)-1H-imidazol-1-yl)phenyl)-5-(trifluoromethyl)-1,2,4-oxadiazole, 3-(4-(4-(((3-chlorophenyl)thio)methyl)-1H-imidazol-1-yl)phenyl)-5-(trifluoromethyl)-1,2,4-oxadiazole, 3-(4-(4-(((4-methoxybenzyl)thio)methyl)-1H-imidazol-1-yl)phenyl)-5-(trifluoromethyl)-1,2,4-oxadiazole, 3-(4-(4-((pyridin-2-ylthio)methyl)-1H-imidazol-1-yl)phenyl)-5-(trifluoromethyl)-1,2,4-oxadiazole, 3-(4-(4-((phenylsulfonyl)methyl)-1H-imidazol-1-yl)phenyl)-5-(trifluoromethyl)-1,2,4-oxadiazole, 3-(4-(4-(((4-methoxyphenyl)sulfonyl)methyl)-1H-imidazol-1-yl)phenyl)-5-(trifluoromethyl)-1,2,4-oxadiazole, 3-(4-(4-((isopropylsulfonyl)methyl)-1H-imidazol-1-yl)phenyl)-5-(trifluoromethyl)-1,2,4-oxadiazole, 3-(4-(4-(((2-fluorophenyl)sulfonyl)methyl)-1H-imidazol-1-yl)phenyl)-5-(trifluoromethyl)-1,2,4-oxadiazole, 3-(4-(4-(((4-fluorophenyl)sulfonyl)methyl)-1H-imidazol-1-yl)phenyl)-5-(trifluoromethyl)-1,2,4-oxadiazole, 3-(4-(4-(((3-chlorophenyl)sulfonyl)methyl)-1H-imidazol-1-yl)phenyl)-5-(trifluoromethyl)-1,2,4-oxadiazole, 3-(4-(4-(((4-methoxybenzyl)sulfonyl)methyl)-1H-imidazol-1-yl)phenyl)-5-(trifluoromethyl)-1,2,4-oxadiazole, 3-(4-(4-((pyridin-2-ylsulfonyl)methyl)-1H-imidazol-1-yl)phenyl)-5-(trifluoromethyl)-1,2,4-oxadiazole, imino(phenyl)((1-(4-(5-(trifluoromethyl)-1,2,4-oxadiazol-3-yl)phenyl)-1H-imidazol-4-yl)methyl)-$\lambda^6$-sulfanone, (2-fluorophenyl)(imino)((1-(4-(5-(trifluoromethyl)-1,2,4-oxadiazol-3-yl)phenyl)-1H-imidazol-4-yl)methyl)-$\lambda^6$-sulfanone, 4-methyl-N-((1-(4-(5-(trifluoromethyl)-1,2,4-oxadiazol-3-yl)phenyl)-1H-imidazol-4-yl)methyl)benzenesulfonamide, N-((1-(4-(5-(trifluoromethyl)-1,2,4-oxadiazol-3-yl)phenyl)-1H-imidazol-4-yl)methyl)benzenesulfonamide, N-((1-(4-(5-(trifluoromethyl)-1,2,4-oxadiazol-3-yl)phenyl)-1H-imidazol-4-yl)methyl)acetamide, 4-fluoro-N-((1-(4-(5-(trifluoromethyl)-1,2,4-oxadiazol-3-yl)phenyl)-1H-imidazol-4-yl)methyl)benzenesulfonamide, N-((1-(4-(5-(trifluoromethyl)-1,2,4-oxadiazol-3-yl)phenyl)-1H-imidazol-4-yl)methyl)cyclopropanesulfonamide, 4-(trifluoromethyl)-N-((1-(4-(5-(trifluoromethyl)-1,2,4-oxadiazol-3-yl)phenyl)-1H-imidazol-4-yl)methyl)benzamide, N-((1-(4-(5-(trifluoromethyl)-1,2,4-oxadiazol-3-yl)phenyl)-1H-imidazol-4-yl)methyl)isobutyramide, N-((1-(4-(5-(trifluoromethyl)-1,2,4-oxadiazol-3-yl)phenyl)-1H-imidazol-4-yl)methyl)cyclobutanecarboxamide, N-((1-(4-(5-(trifluoromethyl)-1,2,4-oxadiazol-3-yl)phenyl)-1H-imidazol-4-yl)methyl)benzamide, 4-methoxy-N-((1-(4-(5-(trifluoromethyl)-1,2,4-oxadiazol-3-yl)phenyl)-1H-imidazol-4-yl)methyl)benzamide, 2-fluoro-N-((1-(4-(5-(trifluoromethyl)-1,2,4-oxadiazol-3-yl)phenyl)-1H-imidazol-4-yl)methyl)benzamide, N-((1-(4-(5-(trifluoromethyl)-1,2,4-oxadiazol-3-yl)phenyl)-1H-imidazol-4-yl)methyl)methanesulfonamide, N-((1-(4-(5-(trifluoromethyl)-1,2,4-oxadiazol-3-yl)phenyl)-1H-imidazol-4-yl)methyl)thiazole-2-carboxamide, 2-(3,5-dimethyl-1-(4-(5-(trifluoromethyl)-1,2,4-oxadiazol-3-yl)phenyl)-1H-pyrazol-4-yl)-N-phenylacetamide, N-(4-Chlorophenyl)-2-(3,5-dimethyl-1-(4-(5-(trifluoromethyl)-1,2,4-oxadiazol-3-yl)phenyl)-1H-pyrazol-4-yl)acetamide, 2-(3,5-Dimethyl-1-(4-(5-(trifluoromethyl)-1,2,4-oxadiazol-3-yl)phenyl)-1H-pyrazol-4-yl)-N-(4-fluoro-2-methoxyphenyl)acetamide, 2-(3,5-Dimethyl-1-(4-(5-(trifluoromethyl)-1,2,4-oxadiazol-3-yl)phenyl)-1H-pyrazol-4-yl)-N-(pyridin-2-yl)acetamide, 2-(3,5-Dimethyl-1-(4-(5-(trifluoromethyl)-1,2,4-oxadiazol-3-yl)phenyl)-1H-pyrazol-4-yl)-N-(thiazol-2-yl)acetamide, N-(4-Chloro-3-fluorophenyl)-2-(3,5-dimethyl-1-(4-(5-(trifluoromethyl)-1,2,4-oxadiazol-3-yl)phenyl)-1H-pyrazol-4-yl)acetamide, N-(4-Chlorobenzyl)-2-(3,5-dimethyl-1-(4-(5-(trifluoromethyl)-1,2,4-oxadiazol-3-yl)phenyl)-1H-pyrazol-4-yl)acetamide, 4-chloro-N-((1-(4-(5-(trifluoromethyl)-1,2,4-oxadiazol-3-yl)phenyl)-1H-pyrazol-4-yl)methyl)benzamide, N-((1-(4-(5-(trifluoromethyl)-1,2,4-oxadiazol-3-yl)phenyl)-1H-pyrazol-4-yl)methyl)acetamide, N-((1-(4-(5-(trifluoromethyl)-1,2,4-oxadiazol-3-yl)phenyl)-1H-pyrazol-4-yl)methyl)propionamide, 2-fluoro-N-((1-(4-(5-(trifluoromethyl)-1,2,4-oxadiazol-3-yl)phenyl)-1H-pyrazol-4-yl)methyl)benzamide, 4-fluoro-N-((1-(4-(5-(trifluoromethyl)-1,2,4-oxadiazol-3-yl)phenyl)-1H-pyrazol-4-yl)methyl)benzamide, 2-methyl-N-((1-(4-(5-(trifluoromethyl)-1,2,4-oxadiazol-3-yl)phenyl)-1H-pyrazol-4-yl)methyl)thiazole-5-carboxamide, N-((1-(4-(5-(trifluoromethyl)-1,2,4-oxadiazol-3-yl)phenyl)-1H-pyrazol-4-yl)methyl)

cyclobutanecarboxamide, N-((1-(4-(5-(trifluoromethyl)-1,2,4-oxadiazol-3-yl)phenyl)-1H-pyrazol-4-yl)methyl)nicotinamide, N-((1-(4-(5-(trifluoromethyl)-1,2,4-oxadiazol-3-yl)phenyl)-1H-pyrazol-4-yl)methyl)methanesulfonamide, N-((1-(4-(5-(trifluoromethyl)-1,2,4-oxadiazol-3-yl)phenyl)-1H-pyrazol-4-yl)methyl)ethanesulfonamide, N-((1-(4-(5-(trifluoromethyl)-1,2,4-oxadiazol-3-yl)phenyl)-1H-pyrazol-4-yl)methyl)cyclopropanesulfonamide, 2-fluoro-N-((1-(4-(5-(trifluoromethyl)-1,2,4-oxadiazol-3-yl)phenyl)-1H-pyrazol-4-yl)methyl)benzenesulfonamide, 5-chloro-N-((1-(4-(5-(trifluoromethyl)-1,2,4-oxadiazol-3-yl)phenyl)-1H-pyrazol-4-yl)methyl)thiophene-2-sulfonamide, 4-fluoro-N-((1-(4-(5-(trifluoromethyl)-1,2,4-oxadiazol-3-yl)phenyl)-1H-pyrazol-4-yl)methyl)benzenesulfonamide, N-((1-(4-(5-(trifluoromethyl)-1,2,4-oxadiazol-3-yl)phenyl)-1H-pyrazol-4-yl)methyl)pyridine-3-sulfonamide, 1-(pyridin-3-yl)-3-((1-(4-(5-(trifluoromethyl)-1,2,4-oxadiazol-3-yl)phenyl)-1H-pyrazol-4-yl)methyl)urea, 1-(2-fluorophenyl)-3-((1-(4-(5-(trifluoromethyl)-1,2,4-oxadiazol-3-yl)phenyl)-1H-pyrazol-4-yl)methyl)urea, (4-fluorophenyl)(imino)((1-(4-(5-(trifluoromethyl)-1,2,4-oxadiazol-3-yl)phenyl)-1H-imidazol-4-yl)methyl)-$\lambda^6$-sulfanone, (3-chlorophenyl)(imino)((1-(4-(5-(trifluoromethyl)-1,2,4-oxadiazol-3-yl)phenyl)-1H-imidazol-4-yl)methyl)-$\lambda^6$-sulfanone, 2-(3,5-dimethyl-1-(4-(5-(trifluoromethyl)-1,2,4-oxadiazol-3-yl)phenyl)-1H-pyrazol-4-yl)-N-(2-methoxyethyl)acetamide, N-(cyclopropylmethyl)-2-(3,5-dimethyl-1-(4-(5-(trifluoromethyl)-1,2,4-oxadiazol-3-yl)phenyl)-1H-pyrazol-4-yl)acetamide, N-cyclopropyl-2-(3,5-dimethyl-1-(4-(5-(trifluoromethyl)-1,2,4-oxadiazol-3-yl)phenyl)-1H-pyrazol-4-yl)acetamide, 3-(4-(4-(((4-fluorophenyl)sulfinyl)methyl)-1H-imidazol-1-yl)phenyl)-5-(trifluoromethyl)-1,2,4-oxadiazole, 3-(4-(4-((phenylsulfinyl)methyl)-1H-imidazol-1-yl)phenyl)-5-(trifluoromethyl)-1,2,4-oxadiazole, (2-fluorophenyl)(methyl)(((1-(4-(5-(trifluoromethyl)-1,2,4-oxadiazol-3-yl)phenyl)-1H-pyrazol-4-yl)methyl)imino)-$\lambda^6$-sulfanone, (4-methoxyphenyl)(methyl)(((1-(4-(5-(trifluoromethyl)-1,2,4-oxadiazol-3-yl)phenyl)-1H-pyrazol-4-yl)methyl)imino)-$\lambda^6$-sulfanone, methyl(thiazol-2-yl)(((1-(4-(5-(trifluoromethyl)-1,2,4-oxadiazol-3-yl)phenyl)-1H-pyrazol-4-yl)methyl)imino)-$\lambda^6$-sulfanone, methyl(pyridin-4-yl)(((1-(4-(5-(trifluoromethyl)-1,2,4-oxadiazol-3-yl)phenyl)-1H-pyrazol-4-yl)methyl)imino)-$\lambda^6$-sulfanone and methyl(phenyl)(((1-(4-(5-(trifluoromethyl)-1,2,4-oxadiazol-3-yl)phenyl)-1H-pyrazol-4-yl)methyl)imino)-$\lambda^6$-sulfanone.

In one embodiment, the present invention provides a compound of formula (II),

Formula (II)

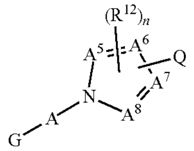

wherein,

G is —CN or —C($NH_2$)═N—OH;

A, $A^5$, $A^6$, $A^7$, $A^8$, $R^{12}$, n and Q are as defined in above.

In one embodiment, the present invention provides a compound of formula (III),

Formula (III)

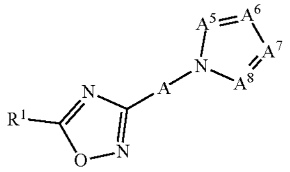

wherein, $R^1$ is $C_1$-$C_2$ haloalkyl;

$A^5$, $A^6$, $A^7$ and $A^8$ are independently selected from $CR^9$ or N; provided that at least one of $A^5$, $A^6$, $A^7$ and $A^8$ is $CR^9$;

$R^9$ is selected from the group consisting of hydrogen, halogen, nitro, cyano, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl and $C_3$-$C_6$ cycloalkoxy; —$S(O)_2C_1$, $C_1$-$C_6$ alkylamino, $C_1$-$C_6$ dialkylamino and $C_1$-$C_6$ trialkylamino.

The compound of the present invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compound of the present invention may be present as a mixture of stereoisomers, individual stereoisomers or as an optically active form.

An anion part of the salt in case the compound of formula (I) is a cationic or capable of forming a cation can be inorganic or organic. Alternatively, a cation part of the salt in case the compound of formula (I) is an anionic or capable of forming anion can be inorganic or organic. Examples of inorganic anion part of the salt include but are not limited to chloride, bromide, iodide, fluoride, sulphate, phosphate, nitrate, nitrite, hydrogen carbonates, hydrogensulphate. Examples of organic anion part of the salt include but are not limited to formate, alkanoates, carbonates, acetates, trifluoroacetate, trichloroacetate, propionate, glycolate, thiocyanate, lactate, succinate, malate, citrates, benzoates, cinnamates, oxalates, alkylsulphates, alkylsulphonates, arylsulphonates aryldisulphonates, alkylphosphonates, arylphosphonates, aryldiphosphonates, p-toluenesulphonate, and salicylate. Examples of inorganic cation part of the salt include but are not limited to alkali and alkaline earth metals. Examples of organic cation part of the salt include but are not limited to pyridine, methyl amine, imidazole, benzimidazole, hitidine, phosphazene, tetramethyl ammonium, tetrabutylammonium, choline and trimethylamine.

Metal ions in metal complexes of the compound of formula (I) are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period and the first to eighth transition groups. Here, the metals can be present in the various valencies that they can assume.

The compound selected from formula (I), (including all stereoisomers, N-oxides, and salts thereof), typically may exist in more than one form. Formula (I) thus includes all crystalline and non-crystalline forms of the compound that formula (I) represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by formula (I) can exhibit beneficial effects (e.g., suitability for preparation of useful formulations, improved biological performance) relative to another polymorph or a mixture of polymorphs of the same compound represented by formula (I). Preparation and isolation of a particular polymorph of a compound represented by formula (I) can be achieved by methods known to those skilled in the art including, for example, crystallization using selected solvents and temperatures.

In an embodiment, the present invention provides a process for the synthesis of compound of formula (I).

The process for the synthesis of compound of formula (I) comprising at least one of the following steps (a) to (m):

a) reacting a compound of formula 3 with a hydroxyl amine to afford a compound of formula 4;

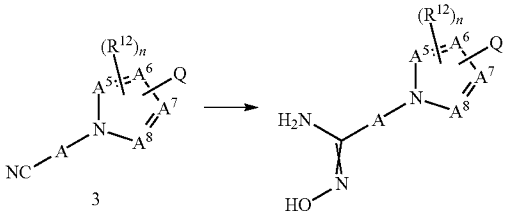

3 4 wherein, $R^{12}$, A, $A^5$, $A^6$, $A^7$ and $A^8$ are as defined in detailed description above; Q is $Q_3$, $Q_6$, $Q_7$, $Q_{11}$, H, $CR^2R^3N(Boc)_2$, or $CR^2R^3SR^7$ and provided that $R^{12}$ is not cyano;

b) reacting the compound of formula 4 with a suitable carboxylic acid anhydride of formula 5 to afford a compound of formula (I);

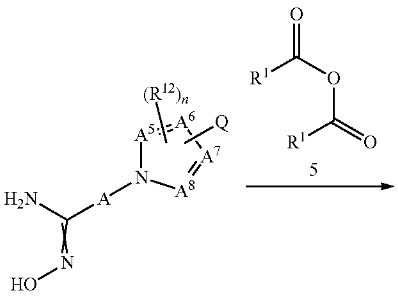

5

4

-continued

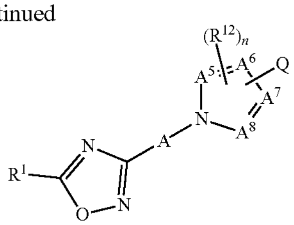

Formula (I)

wherein, $R^1$, $R^{12}$, A, $A^5$, $A^6$, $A^7$ and $A^8$ are as defined in detailed description above; Q is $Q_3$, $Q_6$, $Q_7$, $Q_{11}$, H, $CR^2R^3N(Boc)_2$, or $CR^2R^3SR^7$; provided that $R^{12}$ is not cyano;

c) reacting a compound of formula 6 with a compound of formula 7 to afford a compound of formula (I);

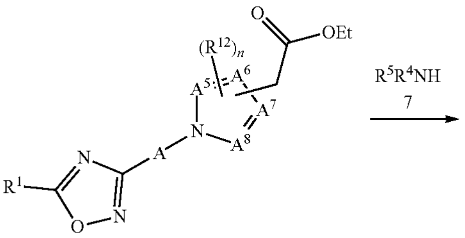

6

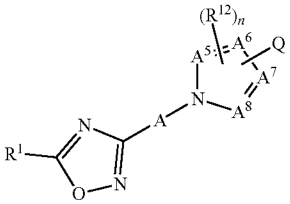

Formula (I)

wherein, $R^1$, $R^{12Z}$, A, $A^5$, $A^6$, $A^7$ and $A^8$ are as defined in detailed description above; Q is $Q_1$;

d) reacting a compound of formula 12 with a compound of formula $2^d$ to afford a compound of formula (I);

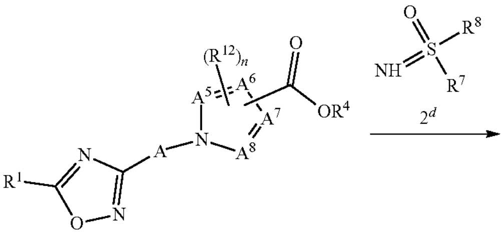

12

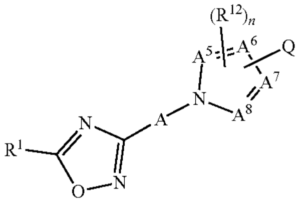

Formula (I)

wherein, $R^1$, $R^{12}$, A, $A^5$, $A^6$, $A^7$ and $A^8$ are as defined in detailed description; Q is $Q_4$;

e) reacting a compound of formula 16 with a chlorosulphonic acid to afford a compound of formula 17;

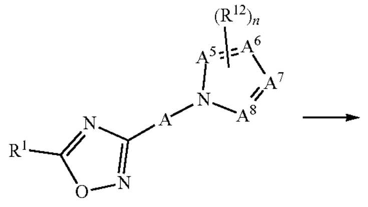

16

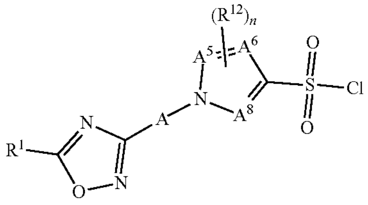

17 wherein, $R^1$, $R^{12}$, A, $A^5$, $A^6$, and $A^8$ are as defined in detailed description above; $A^7$ is CH; and $R^{12}$ is not cyano;

f) reacting a compound of formula 17 with a suitable amine of formula $NHR^4R^5$ to afford a compound of formula (I);

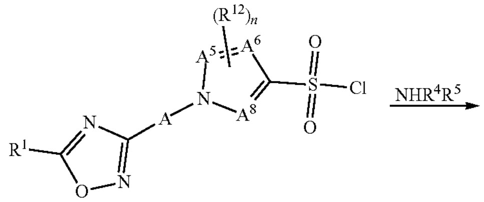

17

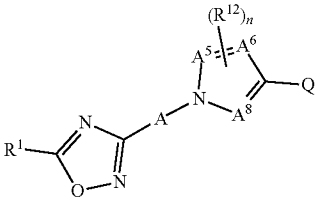

Formula (I)

wherein, $R^1$, $R^4$, $R^5$, $R^{12}$, A, $A^5$, $A^6$ and $A^8$ are as defined in detailed description above; Q is $Q_6$; $A^7$ is CH; and $R^{12}$ is not cyano;

g) reacting a compound of formula 21 with a compound of formula $2^h$ to afford a compound of formula 22;

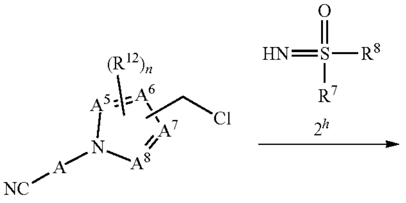

21

$2^h$

-continued

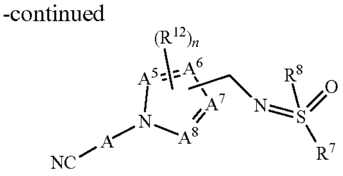

22 wherein, $R^7$, $R^8$, $R^{12}$, A, $A^5$, $A^6$, $A^7$ and $A^8$ are as defined in detailed description above;

h) reacting the compound of formula 22 with a hydroxyl amine to afford a compound of formula 23;

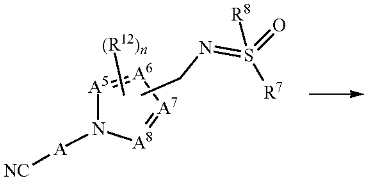

22

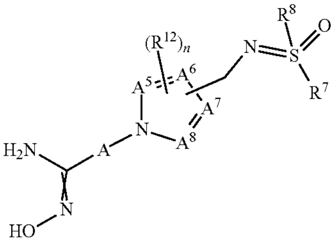

23 wherein, $R^7$, $R^8$, $R^{12}$, A, $A^5$, $A^6$, $A^7$ and $A^8$ are as defined in detailed description above;

i) reacting a compound of formula 23 with a compound of formula 5 to afford a compound of formula (I);

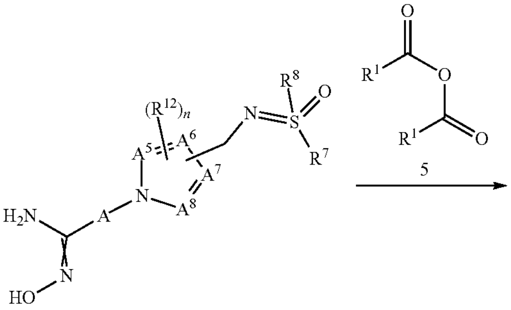

5

23

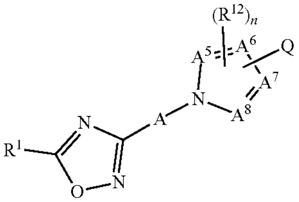

Formula (I)

wherein, $R^1$, $R^7$, $R^8$, $R^{12}$, A, $A^5$, $A^6$, $A^7$ and $A^8$ are as defined in detailed description above; Q is $Q_5$;

j) reacting a compound of formula 26 with a suitable acid to afford a compound of formula 27;

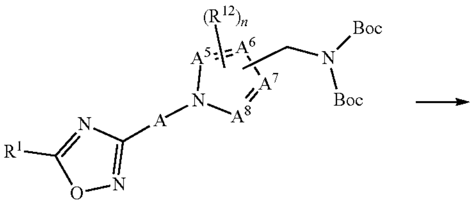

26

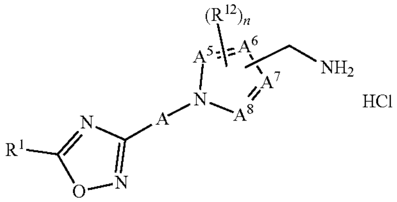

27 wherein, $R^1$, $R^{12}$, A, $A^5$, $A^6$, $A^7$ and $A^8$ are as defined in detailed description above;

k) reacting the compound of formula 27 with a compound of formula $2^e$ or $2^f$ to afford a compound of formula (I);

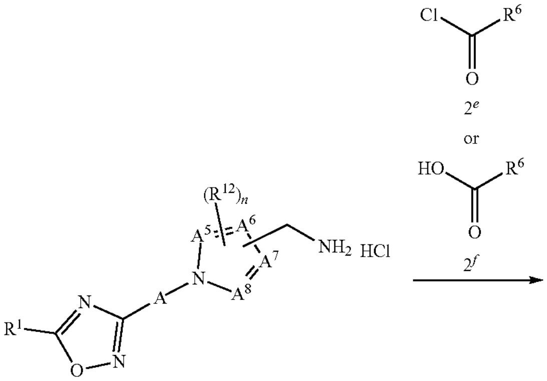

$2^e$ or $2^f$

27

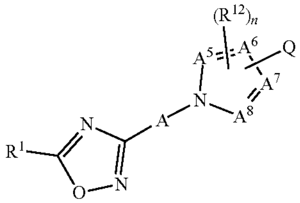

Formula (I)

wherein, $R^1$, $R^6$, $R^{12}$, A, $A^5$, $A^6$, $A^7$ and $A^8$ are as defined in detailed description above; Q is $Q_2$;

l) reacting the compound of formula 27 with a compound formula $2^h$ to afford a compound of formula I

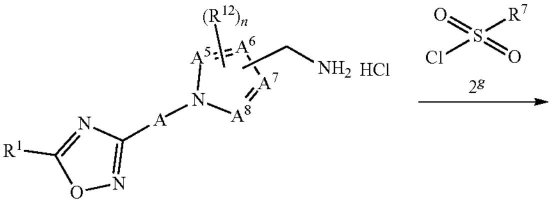

$2^g$

27

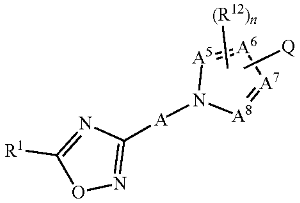

Formula (I)

wherein, $R^1$, $R^{12}$, A, $A^5$, $A^6$, $A^7$ and $A^8$ are as defined in detailed description above; Q is $Q_8$;

m) reacting a compound of formula 30 with a ammonia source reagent in the presence of suitable oxidizing agent to afford a compound of formula I;

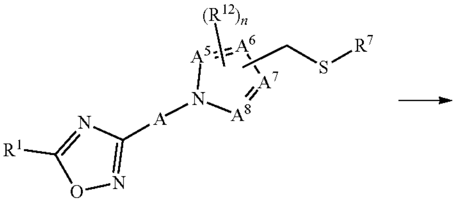

30

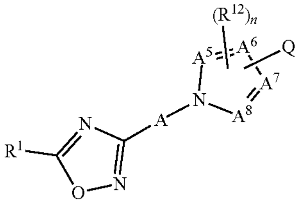

Formula (I)

wherein, $R^1$, $R^7$, $R^{12}$, A, $A^5$, $A^6$, $A^7$ and $A^8$ are as defined in detailed description above; Q is $Q_3$.

The compounds of the present invention as defined by formula (I) and/or in the tables 1 to 16 may be prepared, in known manner, in a variety of ways as described in the schemes 1-9.

General Scheme: 1

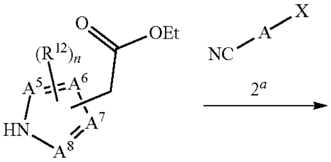

$2^a$

1

-continued

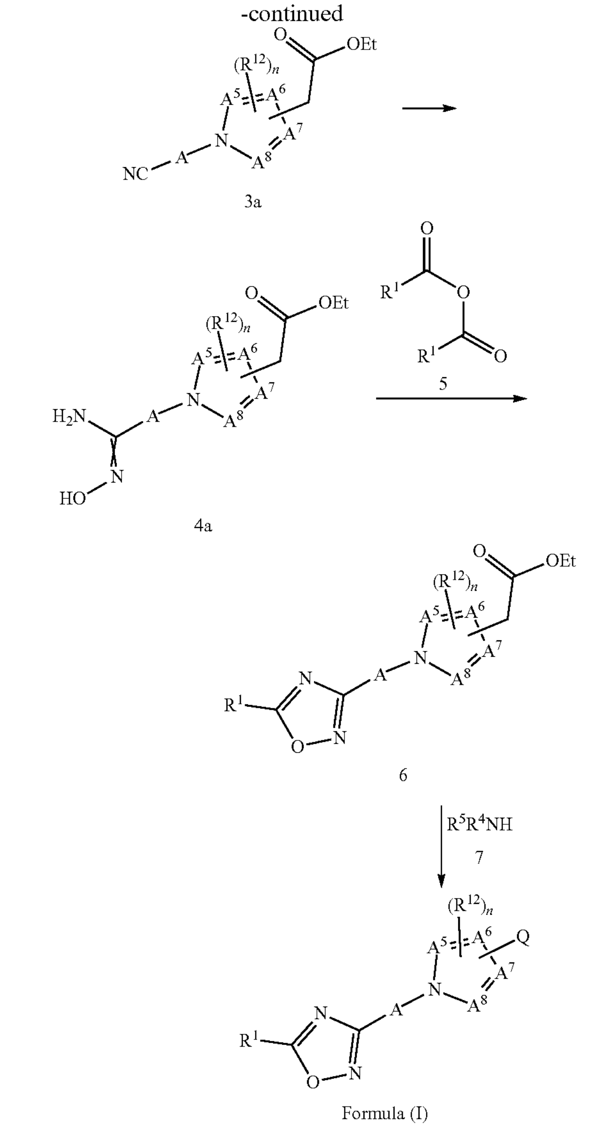

3a

5

4a

6

Formula (I)

wherein, $R^1$, $R^7$, $R^{12}$, A, $A^5$, $A^6$, $A^7$ and $A^8$ are as defined in detailed description above; Q is $Q_1$ and provided that $R^{12}$ is not cyano.

Step: 1

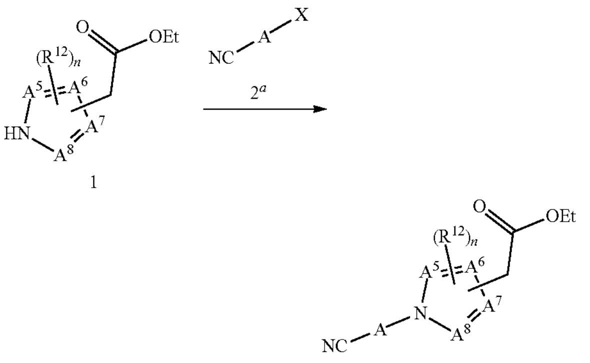

1

$2^a$

3a

The compound of formula 3a can be obtained by reacting the compound of formula 1 with a compound of formula $2^a$ wherein X is Cl, Br, or I in the presence of catalyst CuI and L-proline as ligand. This reaction is typically carried out in the presence of base such as potassium carbonate or cesium carbonate in polar aprotic solvent such as N,N-dimethylformamide or dimethyl sulfoxide at 50 to 120° C.

Alternatively, the compound of formula 3a can also be obtained by reacting the compound of formula 1 with the compound of formula $2^a$ wherein A is $A^a$ and X is F in the presence of base such as cesium carbonate, potassium carbonate, sodium hydride, etc. This reaction is typically carried out in polar aprotic solvents such as N,N-dimethylformamide or dimethyl sulfoxide at 50 to 120° C.

Step: 2

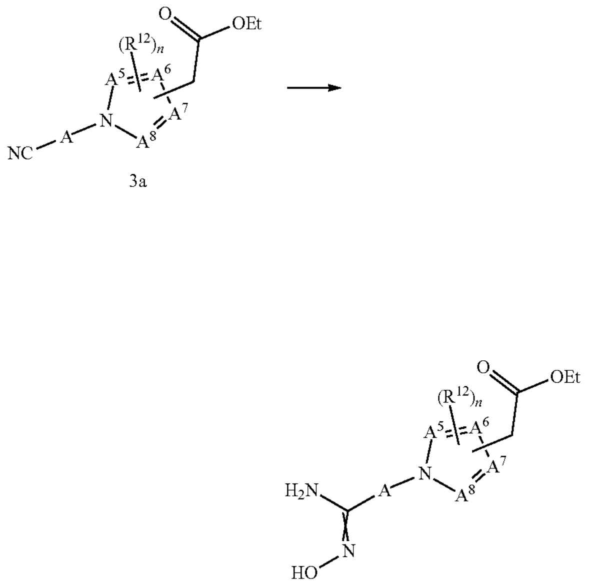

3a

4a

The compound of formula 4a can be prepared by reacting the nitrile compound of formula 3a with a hydroxyl amine in polar protic solvents such as ethanol, methanol, etc. Alternatively, this reaction can also be carried out by using hydroxylamine hydrochloride in the presence of organic and inorganic bases such as triethylamine, N,N-diisopropylethylamine, sodium bicarbonate, etc.

Step: 3

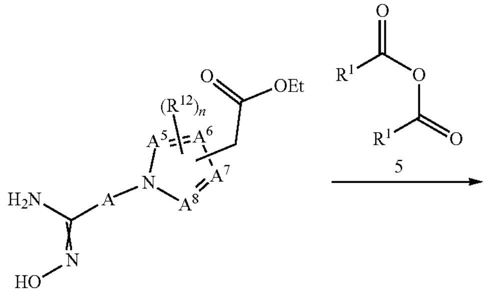

4a

5

-continued

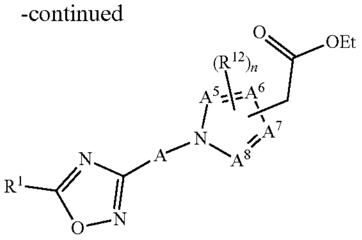

6

The compound of formula 6 can be obtained by reacting the compound of formula 4a and carboxylic acid anhydride of formula 5. These reactions are typically performed in -continued

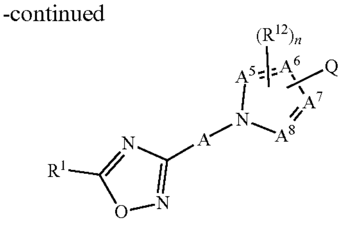

Formula (I)

The compound of formula (I) wherein Q is $Q_1$ can be obtained by reacting the compound of formula 6 with compound of formula 7 in the presence of trimethylaluminium. This reaction can be carried out in aprotic solvents such as toluene at 20-80° C.

General Scheme: 2

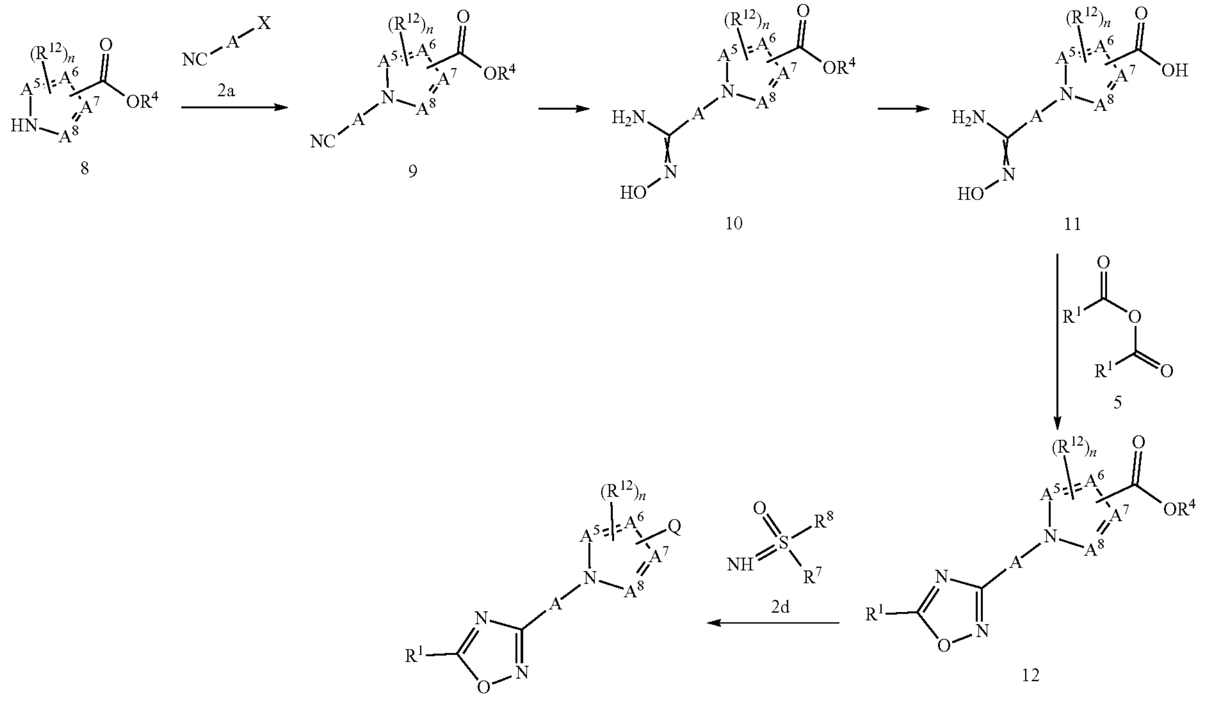

8 9 10 11 5 12 Formula (I)

aprotic solvents such as tetrahydrofuran, 1, 4-dioxane, dichloromethane, etc. optionally in the presence of bases such as triethylamine, N,N-diisopropylethylamine, etc. at 0-50° C.

Step: 4

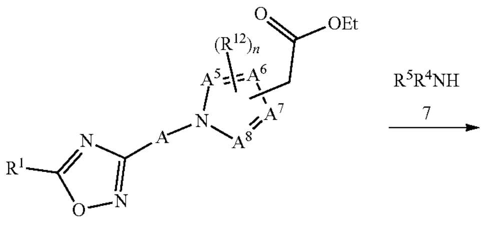

6 wherein, $R^1$, $R^7$, $R^{12}$, A, $A^5$, $A^6$, $A^7$ and $A^8$ are as defined in detailed description above; Q is $Q_4$; $R^{12}$ is not cyano.

Step: 1

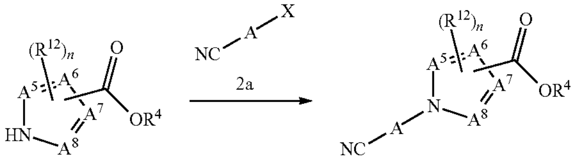

8 9

The compound of formula 9 can be obtained by reacting the compound of formula 8 with the compound of formula $2^a$ wherein X is Cl, Br, or I in the presence of catalyst CuI and L-proline as ligand. This reaction is typically carried out in the presence of base such as potassium carbonate or cesium carbonate in polar aprotic solvents such as N,N-dimethylformamide or dimethyl sulfoxide at 50 to 120° C.

Alternatively, the compound of formula 9 can also be accessed by reacting the compound of formula 8 with the compound of formula $2^a$ wherein A is $A^a$ and X is F in the presence of base such as cesium carbonate, potassium carbonate, sodium hydride, etc. This reaction is typically carried out in polar aprotic solvents such as N,N-dimethylformamide or dimethyl sulfoxide at 50 to 120° C.

Step: 2

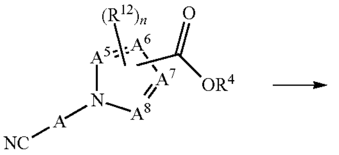

9

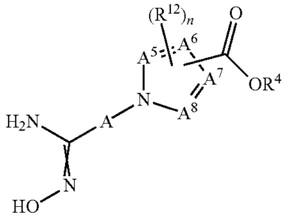

10

The compound of formula 10 can be prepared by reacting the nitrile compound of formula 9 with hydroxyl amine in polar protic solvents such as ethanol, methanol, etc. Alternatively, this reaction can also be carried out by using hydroxylamine hydrochloride in the presence of organic and inorganic bases such as triethylamine, N,N-diisopropylethylamine, sodium bicarbonate, etc.

Step: 3

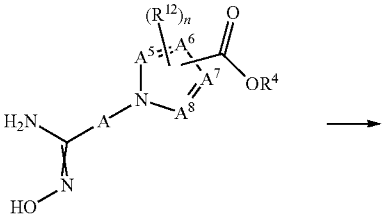

10

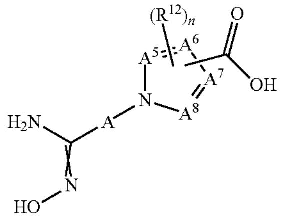

11

The compound of formula 11 can be obtained by hydrolyzing the compound of formula 10 in the presence of base such as sodium hydroxide, lithium hydroxide or potassium hydroxide in an aqueous mixture of solvents such as ethanol, methanol, tetrahydrofuran, etc. at 0-30° C.

Step: 4

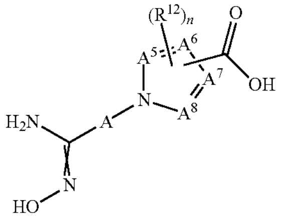

11

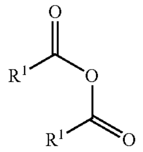

5

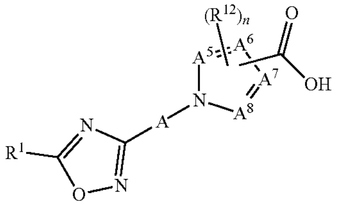

12

The compound of formula 12 can be obtained by reacting the compound of formula 11 and carboxylic acid anhydride of formula 5. This reaction is typically performed in aprotic solvents such as tetrahydrofuran, 1, 4-dioxane, dichloromethane, etc. optionally in the presence of bases such as triethylamine, N,N-diisopropylethylamine, etc. at 0-50° C.

Step: 5

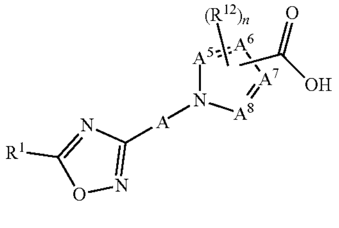

12

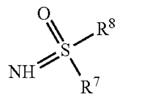

$2^d$

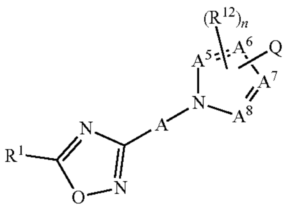

Formula (I)

The compound of formula (I) wherein Q is $Q_4$ in which n is 0; can be obtained by reaction compound of 12 with compound of formula $2^d$ in the presence of amide coupling reagents such as N-(3-Dimethylaminopropyl)-N'-ethylcarbodiimide hydrochloride and 4-dimethylaminopyridine. This reaction is typically carried out in solvents such as dichloromethane or dimethylformamide at 0-30° C.

General scheme: 3

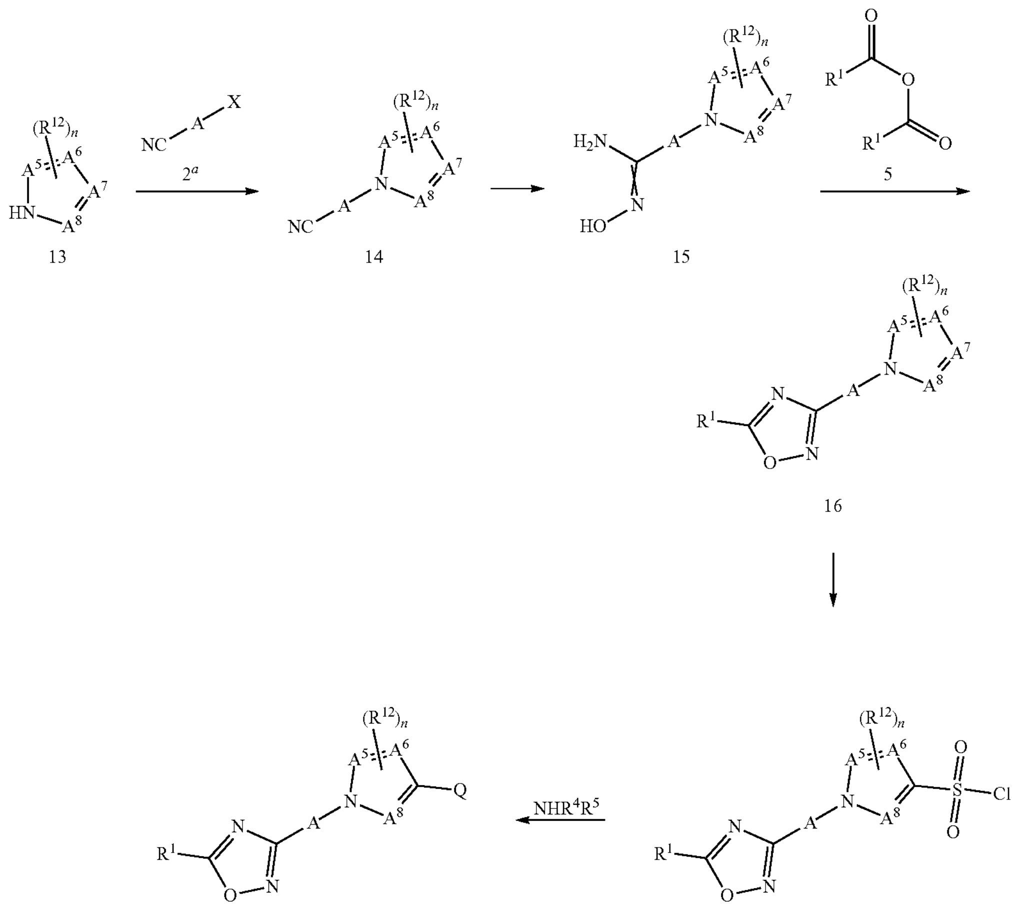

I 17 wherein, $R^1$, $R^4$, $R^5$, $R^{12}$, A, $A^5$, $A^6$ and $A^8$ are as defined in detailed description above; Q is $Q_6$; $A^7$ is CH; and $R^{12}$ is not cyano.

Step: 1

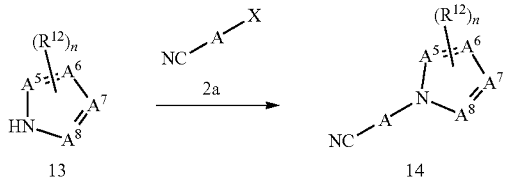

13 14

The compound of formula 14 can be obtained by reacting the compound of formula 13 with the compound of formula $2^a$ wherein X is Cl, Br, or I in the presence of catalyst CuI and L-proline as ligand. This reaction is typically carried out in the presence of base such as potassium carbonate or cesium carbonate in polar aprotic solvents such as N,N-dimethylformamide or dimethyl sulfoxide at 50 to 120° C.

Alternatively, the compound of formula 9 can also be accessed by reacting the compound of formula 8 with compound of formula $2^a$ wherein A is $A^a$ and X is F in the presence of base such as cesium carbonate, potassium carbonate, sodium hydride, etc. This reaction is typically carried out in polar aprotic solvents such as N,N-dimethylformamide or dimethyl sulfoxide at 50 to 120° C.

Step: 2

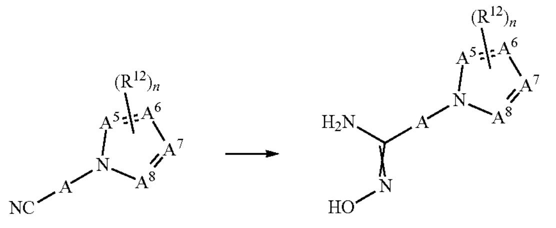

14 15

The compound of formula 15 can be prepared by reacting the nitrile compound of formula 14 with a hydroxyl amine in polar protic solvents such as ethanol, methanol, etc. at 20-60° C. Alternatively, this reaction can also be carried out by using hydroxylamine hydrochloride in the presence of organic and inorganic bases such as triethylamine, N,N-diisopropylethylamine or sodium bicarbonate, etc.

Step: 3

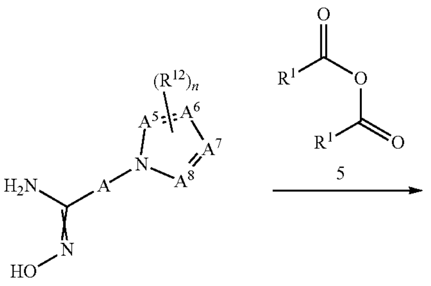

15

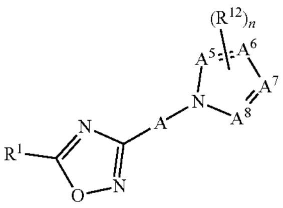

16

The compound of formula 16 can be obtained by reacting the compound of formula 15 and carboxylic acid anhydride of formula 5. This reaction is typically performed in aprotic solvents such as tetrahydrofuran, 1,4-dioxane, dichloromethane, etc. optionally in the presence of bases such as triethylamine, N,N-diisopropylethylamine, etc. at 0-50° C.

Step: 4

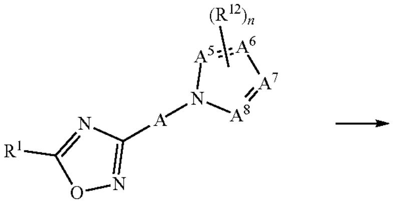

16

-continued

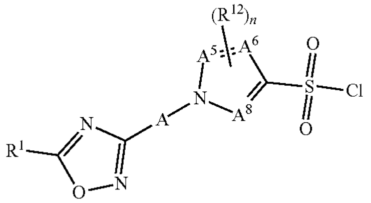

17

The compound of formula 17 can be obtained by reacting compound of formula 16 with chlorosulphonic acid at 50-110° C.

Step: 5

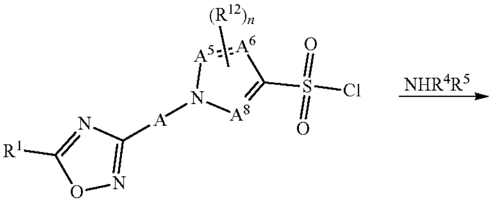

17

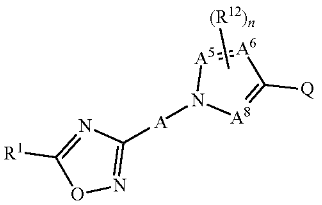

Formula (I)

The compound of formula (I) wherein Q is $Q_6$ can be obtained by reacting the compound of formula 17 with a compound of formula $NHR^4R^5$ in the presence of base such as triethylamine, N,N-diisopropylethylamine, etc. This reaction is typically carried out in aprotic solvents such as dichloromethane, tetrahydrofuran, etc. at 0-40° C.

General scheme: 4

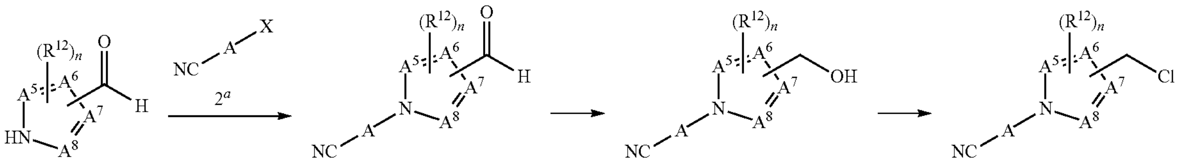

18 19 20 21

-continued

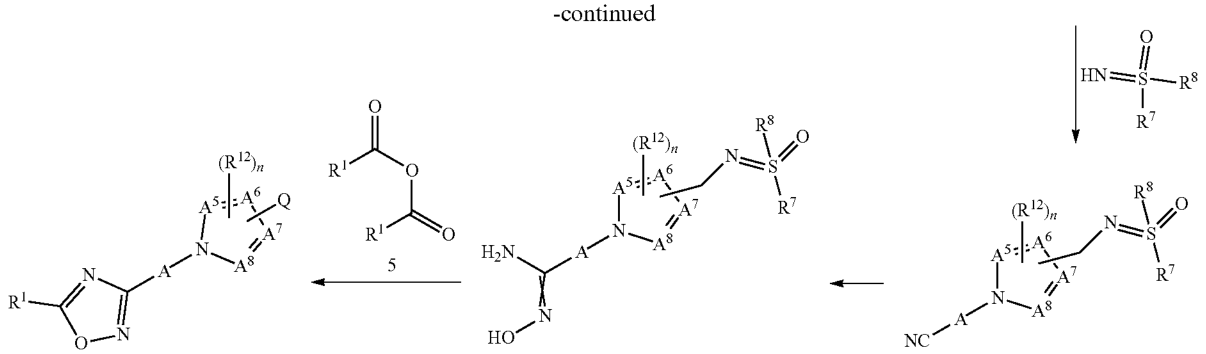

Formula (I) 23 22 wherein, $R^1$, $R^7$, $R^8$, $R^{12}$, A, $A^5$, $A^6$, $A^7$ and $A^8$ are as defined in detailed description above; Q is $Q_5$; provided that $R^{12}$ is not cyano.

Step: 1

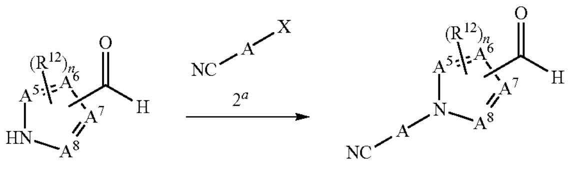

18 19

The compound of formula 19 can be obtained by reacting the compound of formula 18 with the compound of formula $2^a$ wherein X is Cl, Br, or I in the presence of catalyst CuI and L-proline as ligand. This reaction is typically carried out in the presence of base such as potassium carbonate or cesium carbonate in polar aprotic solvents such as N,N-dimethylformamide or dimethyl sulfoxide at 50 to 120° C.

Alternatively, the compound of formula 9 can also be obtained by reacting compound of formula 8 with compound of formula $2^a$ wherein A is $A^a$ and X is F in the presence of base such as cesium carbonate, potassium carbonate, sodium hydride etc. This reaction is typically carried out in polar aprotic solvents such as N,N-dimethylformamide or dimethyl sulfoxide at 50 to 120° C.

Step: 2

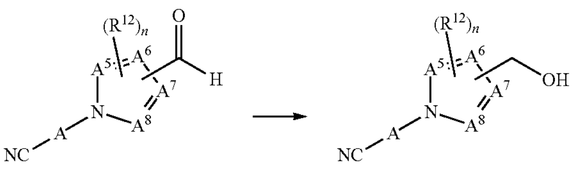

19 20

The compound of formula 20 can be obtained by reacting the compound of formula 19 with reducing agents such as sodium borohydride. This reaction is carried out in a mixture of solvents such as tetrahydrofuran and methanol at 0-30° C.

Step: 3

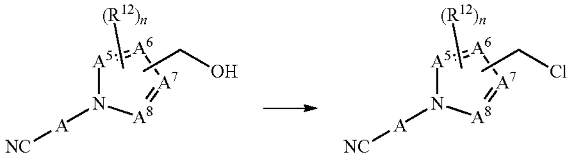

20 21

The compound of formula 21 can be obtained by reacting the compound of formula 20 with reagents such as thionyl chloride. This reaction is carried out in solvents such as chloroform at 40 to 70° C.

Step: 4

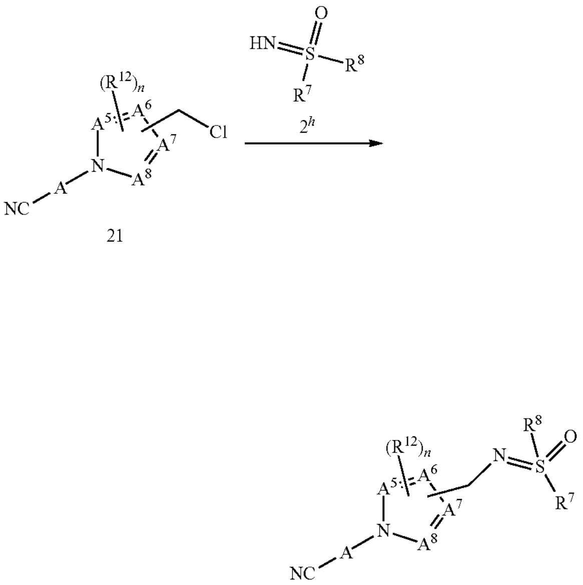

21

22

The compound of formula 22 can be obtained by reacting compound of formula 21 with compound of formula $2^h$ in the presence of base such as potassium tert-Butoxide. This reaction is typically carried out in solvents such as tetrahydrofuran or dimethylformamide at 0-30° C.

Step: 5

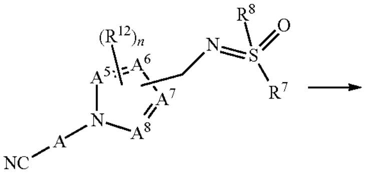

22

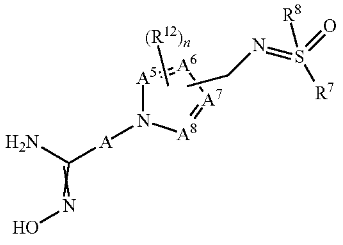

23

The compound of formula 23 can be prepared by reacting the nitrile compound of formula 22 with a hydroxyl amine in polar protic solvents such as ethanol, methanol, etc. at 20-60° C. Alternatively, this reaction can also be carried out by using hydroxylamine hydrochloride in the presence of organic and inorganic bases such as triethylamine, N,N-diisopropylethylamine, sodium bicarbonate, etc.

Step: 6

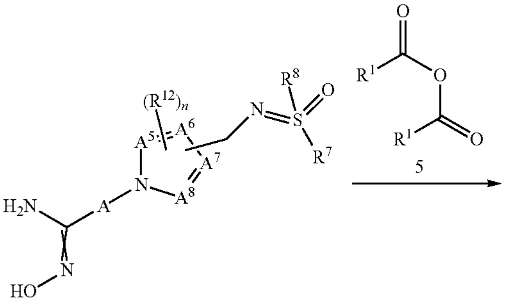

23

5

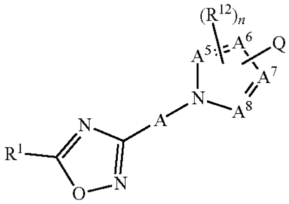

I

The compound of formula (I) wherein Q is $Q_5$ n is 1; can be obtained by reacting compound of formula 23 and carboxylic acid anhydride of formula 5. This reaction is typically performed in aprotic solvents such as tetrahydrofuran, 1,4-dioxane, dichloromethane, etc. optionally in the presence of bases such as triethylamine, N,N-diisopropylethylamine, etc. at 0-50° C.

General scheme: 5

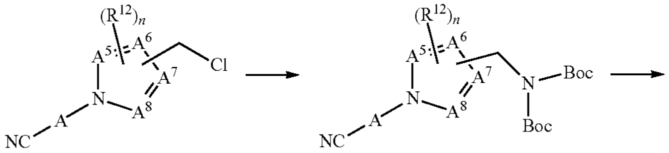

21

24

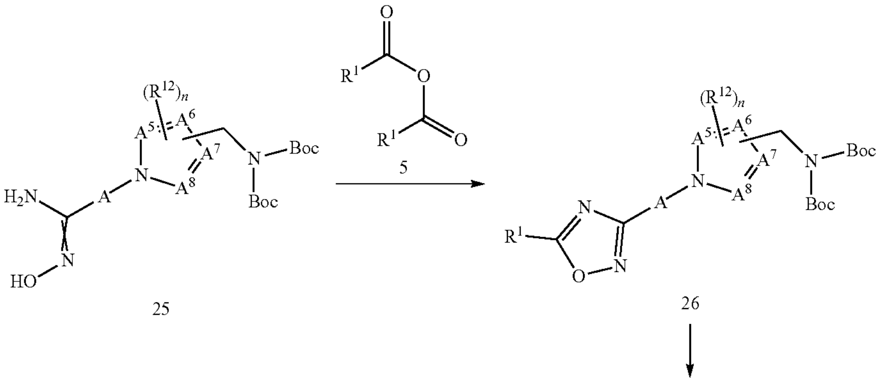

25

5

26

-continued

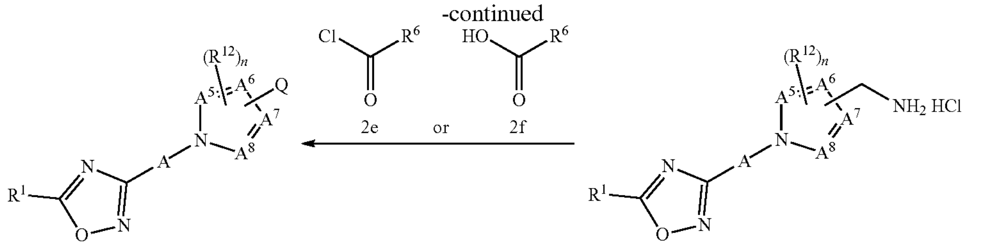

Formula (I) 27 wherein, $R^1$, $R^6$, $R^{12}$, A, $A^5$, $A^6$, $A^7$ and $A^8$ are as defined in detailed description above; Q is $Q_2$, $R^{12}$ is not cyano.

Step: 1

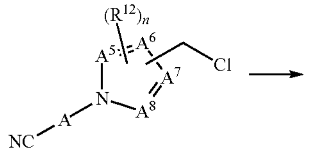

21

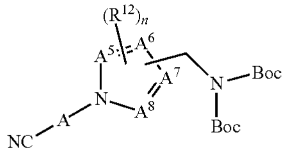

24

The compound of formula 24 can be prepared by reacting the compound of formula 21 with di-tert-butyl iminodicarboxylate in the presence of base such as potassium carbonate or cesium carbonate. This reaction is typically carried out in polar aprotic solvents such as N,N-dimethylformamide at 70 to 100° C.

Step: 2

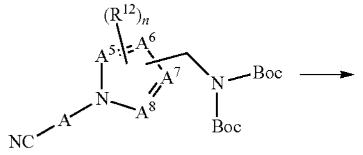

24

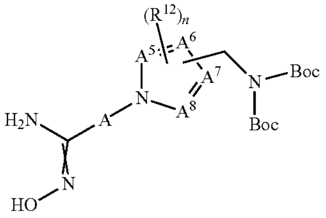

25

The compound of formula 25 can be prepared by reacting the nitrile compound of formula 24 with hydroxyl amine in polar protic solvents such as ethanol, methanol, etc. at 20-60° C. Alternatively, this reaction can also be carried out by using hydroxylamine hydrochloride in the presence of organic and inorganic bases such as triethylamine, N,N-diisopropylethylamine, sodium bicarbonate, etc.

Step: 3

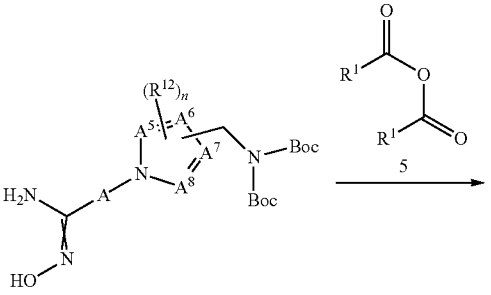

25

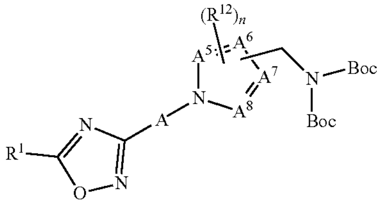

26

The compound of formula 26 can be obtained by reacting the compound of formula 25 and carboxylic acid anhydride of formula 5. This reaction is typically performed in aprotic solvents such as tetrahydrofuran, 1,4-dioxane, dichloromethane, etc. optionally in the presence of bases such as triethylamine, N,N-diisopropylethylamine, etc. at 0-50° C.

Step: 4

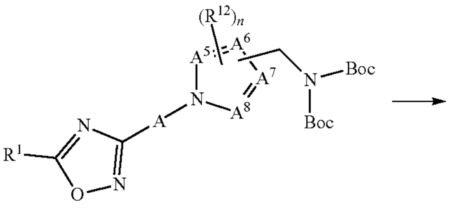

26

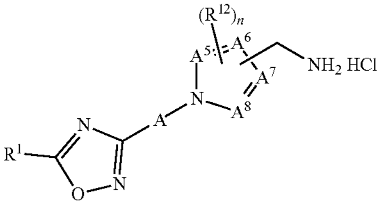

27

The compound of formula 27 can be obtained by deprotecting the compound of formula 26 in the presence of acid such as 4M hydrochloric acid in 1,4-dioxane. This reaction is carried out in solvents such as dichloromethane or tetrahydrofuran at 0-30° C.

Step: 5

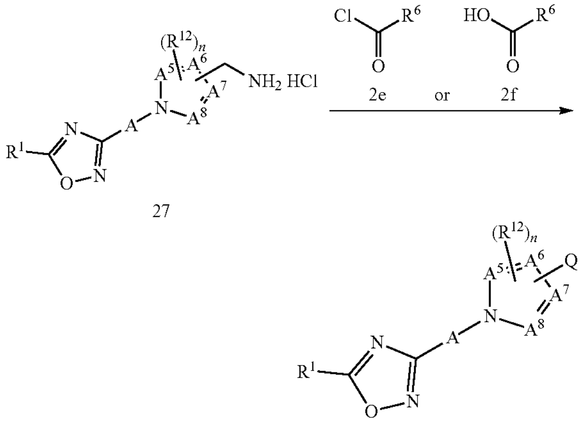

27

Formula (I)

The compound of formula (I) wherein Q is $Q_2$ can be obtained by reacting compound of formula 27 with compound of $2^e$ in the presence of base such as triethylamine or N,N-diisopropylethylamine. This reaction is carried out in aprotic solvents such as dichloromethane, tetrahydrofuran, etc. at 0-30° C.

Alternatively, the compound of formula (I) wherein Q is $Q_2$ can also be obtained by reacting compound of formula 27 with compound of formula $2^f$ in presence of amide coupling reagents such as 1-[Bis(dimethylamino)methylene]-1H-1,2,3-triazolo[4,5-b]pyridinium 3-oxide hexafluorophosphate (HATU), N-(3-dimethylaminopropyl)-N'-ethylcarbodiimide hydrochloride and 4-dimethylaminopyridine, etc. This reaction is carried out in the presence of base such as triethylamine or N,N-diisopropylethylamine in solvents such as dichloromethane or dimethylformamide at 0-40° C.

General scheme: 6

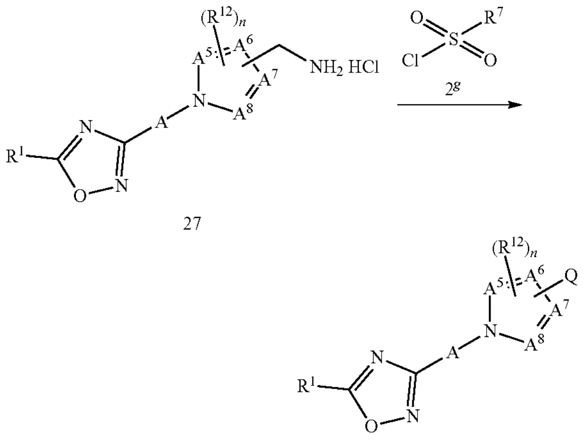

27

Formula (I)

wherein, $R^1$, $R^{12}$, A, $A^5$, $A^6$, $A^7$ and $A^8$ are as defined in detailed description above; Q is $Q_8$; provided that $R^{12}$ is not cyano.

The compound of formula (I) wherein Q is $Q_8$ can be obtained by reacting the compound of formula 27 with a sulphonyl chloride of formula $2^g$ in the presence of base such as triethylamine or N,N-diisopropylethylamine in solvents such as dichloromethane at 0-30° C.

General scheme: 7

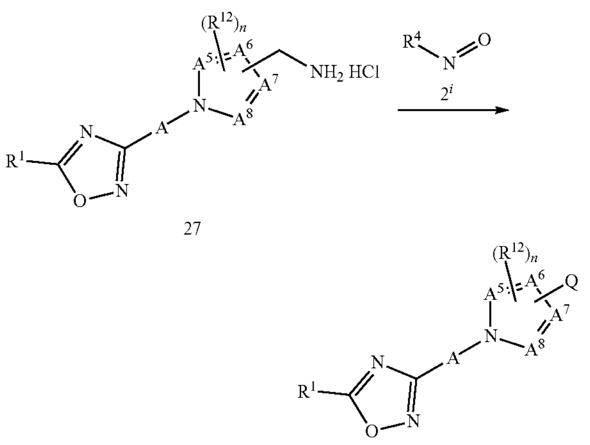

27

Formula (I)

wherein, $R^1$, $R^{12}$, A, $A^5$, $A^6$, $A^7$ and $A^8$ are as defined in detailed description above; Q is $Q_9$; provided that $R^{12}$ is not cyano.

The compound of formula (I) wherein Q is $Q_9$ can be obtained by reacting the compound of formula 27 with isocyantes of formula 2' in the presence of base such as triethylamine or N,N-diisopropylethylamine in solvents such as acetonitrile, dichloromethane or tetrahydrofuran at 0-30° C.

General Scheme: 8

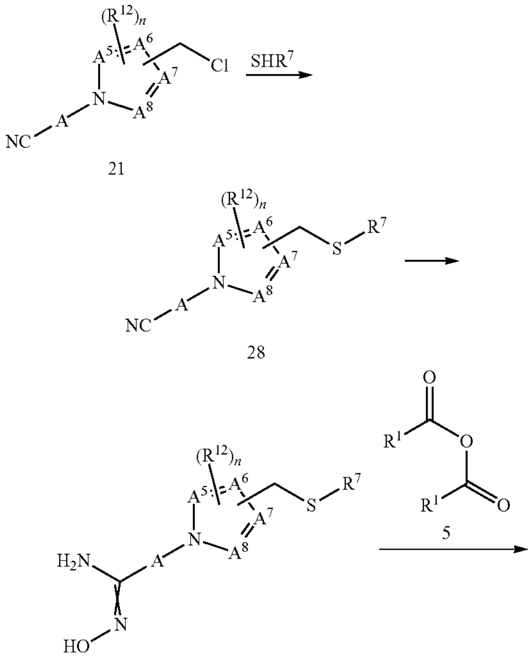

21

28

29

-continued

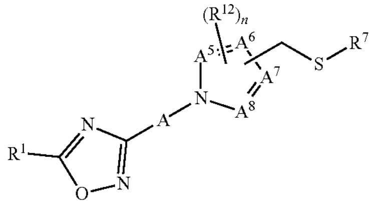

30

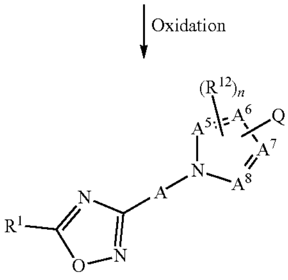

Formula (I)

wherein, $R^1$, $R^{12}$, A, $A^5$, $A^6$, $A^7$ and $A^8$ are as defined in detailed description above; Q is $Q_3$; provided that $R^{12}$ is not cyano.

Step: 1

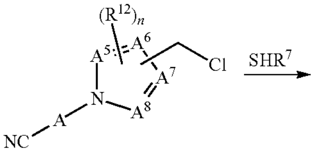

21

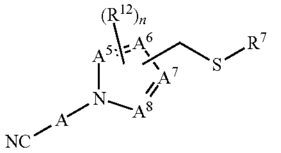

28

The compound of formula 28 can be prepared by reacting the compound of formula 21 with thiol compound of formula $R^7SH$ in the presence of base such as potassium carbonate, cesium carbonate, sodium hydride or potassium tert-butoxide in solvents such as dimethylformamide or dimethyl sulfoxide at 0-80° C.

Step: 2

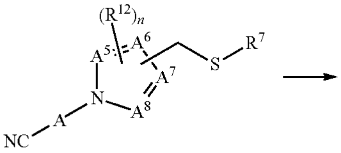

28

-continued

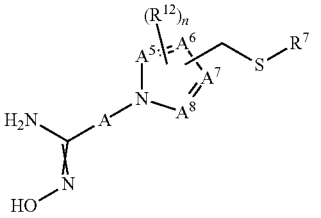

29

The compound of formula 29 can be prepared by reacting the nitrile compound of formula 28 with hydroxyl amine in polar protic solvents such as ethanol, methanol, etc. at 20-60° C. Alternatively, this reaction can also be carried out by using hydroxylamine hydrochloride in the presence of organic and inorganic bases such as triethylamine, N,N-diisopropylethylamine, sodium bicarbonate, etc.

Step: 3

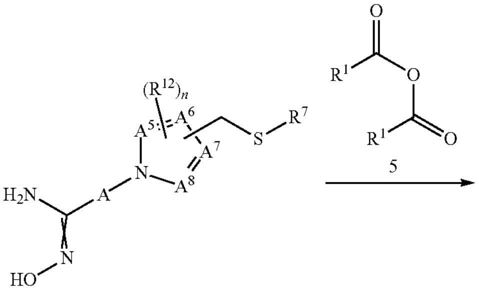

5

29

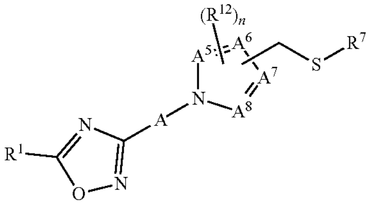

30

The compound of formula 30 can be obtained by reacting the compound of formula 29 and carboxylic acid anhydride of formula 5. This reaction is typically performed in aprotic solvents such as tetrahydrofuran, 1,4-dioxane, dichloromethane, etc. optionally in the presence of bases such as triethylamine, N,N'-diisopropylethylamine, etc. at 0-50° C.

Step: 4

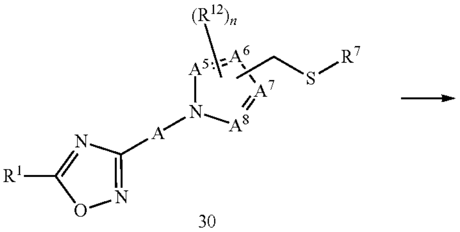

30

-continued

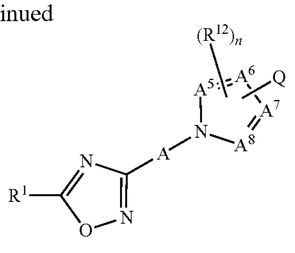

Formula (I)

The compound of formula (I) can be obtained by reacting compound of formula 30 with a suitable oxidizing reagent such as oxonein a suitable solvent such as methanol at 0-30° C.

General scheme: 9

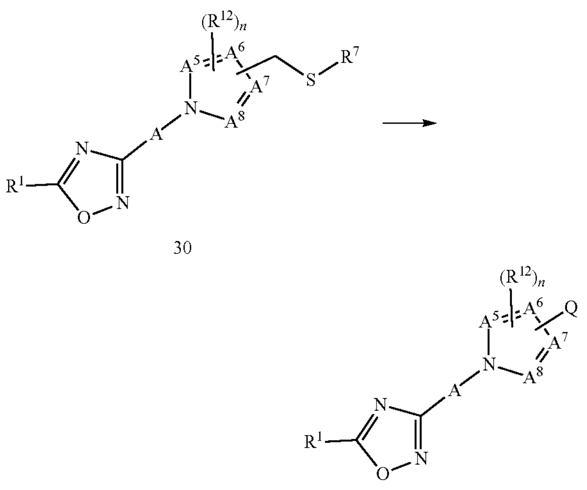

30

Formula (I)

wherein, $R^1$, $R^7$, $R^{12}$, A, $A^5$, $A^6$, $A^7$ and $A^8$ are as defined in detailed description above; Q is

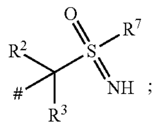

provided that $R^2$ is not cyano.

The compound of formula (I) wherein Q is

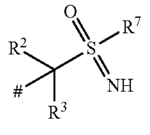

$R^3$ can be prepared by reacting the compound of formula 30 with ammonia source reagents such ammonium carbamate in the presence of suitable oxidizing reagent such as iodoxy benzene diacetate. This reaction is typically carried out in solvents such as methanol at 0-40° C.

In another embodiment the present invention relates to a agrochemical composition comprising the compound of formula (I), agriculturally acceptable salts, metal complexes, constitutional isomers, stereo-isomers, diastereoisomers, enantiomers, chiral isomers, atropisomers, conformers, rotamers, tautomers, optical isomers, polymorphs, geometric isomers, or N-oxides thereof optionally with one or more additional active ingredient with the auxiliary such as inert carrier or any other essential ingredient such as surfactants, additives, solid diluents and liquid diluents.

The compound of formula (I) and the composition according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compound of formula (I) and the composition according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants. Particularly, the compound of formula (I) and the composition according to the invention are important in the control of phytopathogenic fungi on soybeans and on the plant propagation material, such as seeds, and the crop material of soybeans. Accordingly, the present invention also includes a composition comprising at least one compound of formula (I) and seed. The amount of the compound of formula (I) in the composition ranges from 0.1 gai (gram per active ingredient) to 10 kgai (kilogram per active ingredient) per 100 kg of seeds.

Preferably, the compound of formula (I) and composition thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative or reproductive parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts, twigs, flowers, and other parts of plants, including seedlings and young plants, which are to be transplanted after germination or after emergence from soil.

These young plants may also be protected before transplantation by a total or partial treatment by immersion or pouring.

Preferably, treatment of plant propagation materials with the compound of formula (I), the combination and or the composition thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1 185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants capable to synthesize one or more insecticidal proteins, especially those known from the bacterial genus (*Bacillus*), by the use of recombinant DNA techniques are within the scope of the present invention. The *Bacillus* are particularly from *Bacillus thuringiensis*, such as 6-endotoxins, e. g. Cry1A(b), Cry1A(c), Cry1F, Cry1F(a2), Cry11A(b), Cry111A, Cry111B(bl) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO02/015701). Further examples of such toxins or genetically modified plants capable of synthesizing such toxins are disclosed, e. g., in EP374753, WO93/007278, WO95/34656, EP427 529, EP451 878, WO03/18810 und WO03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Abl and the enzyme phosphinothricin-N-acetyltransferase [PAT]); NuCOTN® 33B (cotton cultivars producing the Cry1Ac toxin), Bollgard® I (cotton cultivars producing the Cry1 Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Btl 1 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bbl toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1 F toxin and PAT enzyme).

Furthermore, plants capable to synthesize one or more proteins to increase the resistance or tolerance of those plants to bacterial, viral or fungal pathogens by the use of recombinant DNA techniques are also within the scope of the present invention. Examples of such proteins are the so-called "pathogenesis-related proteins" (PR proteins, see, e. g. EP392225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants capable to synthesize one or more proteins, by the use of recombinant DNA techniques, to increase the productivity (e. g. bio mass production, grain yield, starch content, oil content or protein content), tolerance to drought, salinity or other growth-limiting environmental factors or tolerance to pests and fungal, bacterial or viral pathogens of those plants are within the scope of the present invention.

Furthermore, plants that contain a modified amount of substances of content or new substances of content, by the use of recombinant DNA techniques, to improve human or animal nutrition, e. g. oil crops that produce health-promoting long-chain omega-3 fatty acids or unsaturated omega-9 fatty acids (e. g. Nexera® rape, DOW Agro Sciences, Canada) are also within the scope of the present invention.

Furthermore, plants that contain a modified amount of substances of content or new substances of content, by the use of recombinant DNA techniques, to improve raw material production, e. g. potatoes that produce increased amounts of amylopectin (e. g. Amflora® potato, BASF SE, Germany) are also within the scope of the present invention.

The present invention also relates to a method for controlling or preventing infestation of plants by phytopathogenic micro-organisms in agricultural crops and/or horticultural crops wherein an effective amount of at least one compound of formula (I) or the combination of the present invention or the composition of the present invention, is applied to the seeds of plants. The compound, the combination and the composition of the present invention can be used for controlling or preventing plant diseases.

The compound of formula (I), the combination and/or the composition thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*C. sorokiniana*) on cereals and e. g. *B. oryzae* on rice and turfs; Blumeria (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum on* olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (£. pyri), soft fruits (£. *veneta*: anthracnose) and vines (£. *ampelina*: anthracnose); *Entyloma oryzae* (leaf smut) on rice; *Epicoccum* spp. (black mold) on wheat; *Erysiphe* spp. (powdery mildew) on sugar beets (£. *betae*), vegetables (e. g. *E. pisi*), such as cucurbits (e. g. *E. cichoracearum*), cabbages, rape (e. g. *E. cruciferarum*); *Eutypa lata* (*Eutypa canker* or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans, and *F. verticilioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; Microdochium (syn. *Fusarium*) *nivale* (pink snow mold) on cereals (e. g. wheat or barley); *Microsphaera diffusa* (powdery mildew) on soybeans; Monilinia spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), soybeans, potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or .rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) necator (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [lsyn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compound of formula (I), the combination or the composition thereof may be used to treat several fungal pathogens. Non-limiting examples of pathogens of fungal diseases which can be treated in accordance with the invention include:

- Ustilaginales such as *Ustilaginoidea virens, Ustilago nuda, Ustilago tritici, Ustilago zeae*, rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f. sp. *Hordei, Puccinia striiformis* f. sp. *Secalis, Pucciniastrum coryli*, or *Uredinales* such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries*. Blastocladiomycetes, such as *Physoderma maydis*. Mucoromycetes, such as *Choanephora cucurbitarum; Mucor* spp.; and *Rhizopus arrhizus,*
- In another embodiment diseases caused by rust disease pathogens, for example *Gymnosporangium* species, for example *Gymnosporangium* sabinae; *Hemileia* species, for example *Hemileia vastatrix; Phakopsora* species, for example *Phakopsorapachyrhizi* or *Phakopsora meibomiae; Puccinia* species, for example *Puccinia recondita, Puccinia graminis* oder *Puccinia striiformis; Uromyces* species, for example *Uromyces appendiculatus;*
- In particular, *Cronartium ribicola* (White pine blister rust); *Gymnosporangium juniperi-virginianae* (Cedar-apple rust); *Hemileia vastatrix* (Coffee rust); *Phakopsora meibomiae* and *P. pachyrhizi* (Soybean rust); *Puccinia coronata* (Crown Rust of Oats and Ryegrass); *Puccinia graminis* (Stem rust of wheat and Kentucky bluegrass, or black rust of cereals); *Puccinia hemero-*

*callidis* (Daylily rust); *Puccinia persistens* subsp. triticina (wheat rust or 'brown or red rust'); *Puccinia sorghi* (rust in corn); *Puccinia striiformis* ('Yellow rust' in cereals); *Uromyces appendiculatus* (rust of beans); *Uromyces phaseoli* (Bean rust); *Puccinia melanocephala* ('Brown rust' in sugarcane); *Puccinia kuehnii* ('Orange rust' in sugarcane).

Plants which can be treated in accordance with the invention include the following: cotton, flax, grapevine, fruits, vegetables, such as Rosaceae sp (for example pome fruits such as apples, pears, apricots, cherries, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), Rubiaceae sp. (for example coffee), *Theaceae* sp., *Sterculiceae* sp., *Rutaceae* sp. (for example lemons, oranges and grapefruit); *Vitaceae* sp. (for example grapes); *Solanaceae* sp. (for example tomatoes, peppers), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Poaceae/Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); Malvaceae (for example cotton); useful plants and ornamental plants for gardens and wooded areas; and genetically modified varieties of each of these plants.

More preference is given to controlling the following diseases of soya beans: Fungal diseases on leaves, stems, pods and seeds caused, for example, by *Altemaria* leaf spot (*Altemaria* spec. atrans *tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downymildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectiia crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthephaseolorum*), stem canker (*Diaporthe phaseolorum* var. *caulivora*), phytophthora rot (*Phytophthora megasperma*), brown stem rot (*Phialophora gregata*), pythium rot (*Pythium aphanidennatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The present invention also relates to the use of the compound of formula (I), the combination or the composition thereof for controlling or preventing the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye and *Phakopsoraceae* spp. on various plants, in particular *Phakopsorapachyrhizi* and *P. meibomiae* (soybean rust) on soybeans, *Hemileia vastatrix* (Coffee rust), *Uromyces appendiculatus, Uromyces fabae* and *Uromyces phaseoli* (rust of beans).

The present invention further relates to the use of the compound of formula (I), the combination or the composition thereof for controlling or preventing against phytopathogenic fungi such as *Phakopsora pachyrhizi, Phakopsora meibomiae*, of agricultural crops and or horticultural crops.

The compound of formula (I), the combination and the composition thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria.

As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; *Basidiomycetes* such as *Coniophora* spp., *Coriolus* spp., *Gloeophyllum* spp., *Lentinus* spp., *Pleurotus* spp., *Pora* spp., *Serpula* spp. and *Tyromyces* spp., Deuteromycetes such as *Aspergillus* spp., *Cladosporium* spp., *Penicillium* spp., *Trichoderma* spp., *Altemaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae.*

In one embodiment the compound of formula (I), the combination and the composition thereof, respectively, are particularly suitable for controlling the following plant diseases: *Phakopsora pachyrhizi* and *P. meibomiae* (soybean rust) on soybeans.

The present invention further relates to a method for controlling or preventing phytopathogenic fungi. The method comprises treating the fungi or the materials, plants, plant parts, locus thereof, soil or seeds to be protected against fungal attack, with an effective amount of at least one compound of formula (I) or the combination or the composition comprising at least one compound of formula (I).

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combination according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compound of formula (I), the combination and the composition thereof, respectively, may be used for improving the health of a plant. The invention also relates to a method for improving plant health by treating a plant, its propagation material and/or the locus where the plant is growing or is to grow with an effective amount of compound I and the composition thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compound of formula (I) can be present in different crystal modifications or polymorphs whose biological activity may differ. They are likewise subject matter of the present invention.

The compound of formula (I) are employed as such or in the form of composition for treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with a compound of formula (I), the combination and the composition thereof protectively either at or before planting or transplanting.

The invention also relates to agrochemical composition comprising an auxiliary and at least one compound of formula (I).

An agrochemical composition comprises a fungicidally effective amount of a compound of formula (I). The term "effective amount" denotes an amount of the composition or of the compound of Formula (I), which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound of formula (I) used.

The compound of formula (I), their -oxides, metal complexes, isomers, polymorphs or the agriculturally acceptable salts thereof can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel Formulations for the treatment of plant propagation materials such as seeds (e. g. GF). These and further compositions types are defined in the "Catalogue of pesticide Formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product Formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof. Suitable solid carriers or fillers are mineral earths, e. g. silicates, silica gels, talc, kaolins, limestone, lime, chalk, clays, dolomite, diatomaceous earth, bentonite, calcium sulphate, magnesium sulphate, magnesium oxide; polysaccharides, e. g. cellulose, starch; fertilizers, e. g. ammonium sulphate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulphates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulphates are sulphates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide.

Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound of Formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-soluble concentrates (SL, LS)

10-60 wt % of a compound of formula (I) and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible concentrates (DC)

5-25 wt % of a compound of formula (I) and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable concentrates (EC)

15-70 wt % of a compound of formula (I) and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound of formula (I) and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound of formula (I) are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-dispersible granules and water-soluble granules (WG, SG)

50-80 wt % of a compound of formula (I) are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance. vii) Water-dispersible powders and water-soluble powders (WP, SP, WS) 50-80 wt % of a compound of Formula (I) are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound of formula (I) are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound of formula (I) are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound of formula (I), 0-40 wt % water insoluble organic solvent (e.g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound of Formula (I) according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable powders (DP, DS)

1-10 wt % of a compound of formula (I) are ground finely and mixed intimately with solid carrier (e. g. finely divided kaolin) ad 100 wt %.

xii) Granules (GR, FG)

0.5-30 wt % of a compound of formula (I) are ground finely and associated with solid carrier (e. g. silicate) ad 100 wt %. Granulation is achieved by extrusion, spray-drying or fluidized bed.

xiii) Ultra-low volume liquids (UL)

1-50 wt % of a compound of formula (I) are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active ingredient (ai). The active ingredients (ai) are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations from 0.01 to 60% by weight, preferably from 0.1 to 40%, in the ready-to-use preparations.

Application can be carried out before or during sowing. Methods for applying the compound of formula (I), the combination and the composition thereof, respectively, are application onto plant propagation material, especially seeds, include dressing, coating, pelleting, dusting, and soaking as well as in-furrow application methods. Preferably, the compound of Formula (I), the combination and the composition thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 1.0 kg per ha, and in particular from 0.1 to 1.0 kg per ha.

In the treatment of plant propagation materials such as seeds, e. g. by dusting, coating or drenching seed, amounts of active substance from 0.1 to 1000 g, preferably from 1 to 1000 g, more preferably from 1 to 100 g and most preferably from 5 to 100 g, per 100 kg of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be mixed with the composition according to the invention in a weight ratio of 1:100 to 100:1, preferably 1:20 to 20:1.

A pesticide is generally a chemical or biological agent (such as pesticidally active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term “pesticide” includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

The compound of formula (I), the combination and the composition thereof comprising them in the use as fungicides with other fungicides may result in an expansion of the fungicidal spectrum of activity being obtained or in a prevention of fungicide resistance development. Furthermore, in many cases, extraordinary and unexpected effects are obtained.

The present invention also relates to the combination comprising at least one compound of formula (I) and at least one further pesticidally active substance selected from the group of fungicides, insecticides, nematicides, acaricides, biopesticides, herbicides, safeners, plant growth regulators, antibiotics, fertiliers and nutrients. The pesticidally active substances reported in WO2015185485 pages 36-43 and WO2017093019 pages 42-56 can be used in conjunction with the compound of Formula (I).

The active substances referred to as component 2, their preparation and their activity e. g. against harmful fungi is known; these substances are commercially available. The compounds described by IU PAC nomenclature, their preparation and their pesticidal activity are also known (cf. Can. J. Plant Sci. 48 (6), 587-94, 1968; EP141317; EP152031; EP226917; EP243970; EP256503; EP428941 EP532022; EP1028125; EP1035122; EP1201648; EP1122244, JP2002316902; DE19650197; DE10021412; DE102005009458; U.S. Pat. Nos. 3,296,272; 3,325,503; WO9846608; WO9914187; WO9924413; WO9927783; WO0029404; WO0046148; WO0065913; WO0154501; WO 0156358; WO0222583; WO0240431; WO0310149; WO0311853; WO0314103; WO0316286; WO0353145; WO0361388; WO0366609; WO0374491; WO0449804; WO0483193; WO05120234; WO05123689; WO05123690; WO0563721; WO0587772; WO0587773; WO0615866; WO0687325; WO0687343; WO0782098; WO0790624; WO11028657; WO2012168188; WO2007006670; WO201177514; WO13047749; WO10069882; WO13047441; WO0316303; WO0990181; WO13007767; WO1310862; WO13127704; WO13024009; WO13024010; WO13047441; WO13162072; WO13092224 and WO11135833.

The present invention furthermore relates to agrochemical mixtures comprising at least one compound of formula (I) (component 1) and at least one further active substance useful for plant protection.

By applying the compound of formula (I) together with at least one pesticidally active compound an additional effect can be obtained.

This can be obtained by applying the compound of formula (I) and at least one further pesticidally active substance simultaneously, either jointly (e. g. as tank-mix) or separately, or in succession, wherein the time interval between the individual applications is selected to ensure that the active substance applied first still occurs at the site of action in a sufficient amount at the time of application of the further pesticidally active substance(s). The order of application is not essential for working of the present invention.

When applying the compound of formula (I) and a pesticidally active substance sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In the binary mixtures and the composition according to the invention the weight ratio of the component 1) and the component 2) generally depends on the properties of the active components used, usually it is in the range of 1:1000 to 1000:1, often in the range of 1:100 to 100:1, regularly in the range of 1:50 to 50:1, preferably in the range of 1:20 to 20:1, more preferably in the range of 1:10 to 10:1, even more preferably in the range of 1:4 to 4:1 and in particular in the range of 1:2 to 2:1.

According to a further embodiment of the binary mixtures and the composition thereof, the weight ratio of the component 1) and the component 2) usually is in the range of 1000:1 to 1:1000, often in the range of 100:1 to 1:100, regularly in the range of 50:1 to 1:50, preferably in the range of 20:1 to 1:20, more preferably in the range of 10:1 to 1:10, even more preferably in the range of 4:1 to 1:4 and in particular in the range of 2:1 to 1:2.

In the ternary mixtures, i.e. the composition according to the invention comprising the component 1) and component 2) and a compound III (component 3), the weight ratio of component 1) and component 2) depends from the properties of the active substances used, usually it is in the range of 1:100 to 100:1, regularly in the range of 1:50 to 50:1, preferably in the range of 1:20 to 20:1, more preferably in the range of 1:10 to 10:1 and in particular in the range of 1:4 to 4:1, and the weight ratio of component 1) and component 3) usually it is in the range of 1:100 to 100:1, regularly in the range of 1:50 to 50:1, preferably in the range of 1:20 to 20:1, more preferably in the range of 1:10 to 10:1 and in particular in the range of 1:4 to 4:1.

Any further active components are, if desired, added in a ratio of 20:1 to 1:20 to the component 1).

These ratios are also suitable for inventive mixtures applied by seed treatment.

The invention disclosed in the present disclosure shall now be elaborated with the help of non-limiting examples.

CHEMISTRY EXAMPLES

Example 1: Preparation of N-(4-methoxyphenyl)-2-(1-(4-(5-(trifluoromethyl)-1,2,4-oxadiazol-3-yl)phenyl)-1H-imidazol-4-yl)acetamide (Compound No. 2)

Step 1: Ethyl 2-(1H-imidazol-4-yl)acetate

To a stirred solution of 2-(1H-imidazol-4-yl)acetic acid (7 g, 55 mmol) in ethanol (50 mL), sulfuric acid (0.27 mL, 5.1 mmol) was added, and the reaction mass was refluxed for 2 h. The resulting reaction mixture was cooled to 25° C. and neutralized by aqueous saturated sodium bicarbonate solution (20 mL). The reaction mixture was extracted using the mixture of dichloromethane (80 mL) and methanol (15 mL). The organic layer containing product was dried over anhydrous sodium sulphate and concentrated under reduced pressure to obtain ethyl 2-(1H-imidazol-4-yl)acetate (7.7 g, 90% yield).

Step 2: Ethyl 2-(1-(4-cyanophenyl)-1H-imidazol-4-yl)acetate

To a stirred mixture of potassium carbonate (0.15 g, 1.1 mmol) and ethyl 2-(1H-imidazol-4-yl)acetate (80 mg, 0.5 mmol) in degassed dimethyl sulphoxide (2 mL), 4-iodobenzonitrile (0.1 g, 0.44 mmol), L-proline (30 mg, 0.36 mmol) and copper (I) iodide (0.025 g, 0.1 mmol) were added. The resulting reaction mixture was heated to 80° C. and stirred for 24 h. The reaction mixture was cooled to 25° C. and filtered through celite bed. The celite bed was washed with ethyl acetate (10 mL). The combined ethyl acetate filtrate was washed with water (5 mL), dried over anhydrous sodium sulphate and concentrated under reduced pressure to obtain the crude product. The obtained crude product purified by column chromatography on silica gel using ethyl acetate in hexane as an eluent to obtain ethyl 2-(1-(4-cyanophenyl)-1H-imidazol-4-yl)acetate (56 mg, 50% yield).

Step 3: Ethyl 2-(1-(4-(N'-hydroxycarbamimidoyl)phenyl)-1H-imidazol-4-yl)acetate A stirred suspension of ethyl 2-(1-(4-cyanophenyl)-1H-imidazol-4-yl)acetate (7.5 g, 29 mmol), hydroxylamine hydrochloride (4.1 g, 59 mmol) and sodium bicarbonate (4.9 g, 59 mmol) in ethanol (100 mL) was refluxed for 16 h. The resulting reaction mixture was concentrated under reduced pressure. The obtained residue was diluted with cold water (200 mL). The resulting precipitate was filtered off, washed with cold water (50 mL) and dried under reduced pressure to obtain ethyl 2-(1-(4-(N'-hydroxycarbamimidoyl)phenyl)-1H-imidazol-4-yl)acetate (6.2 g, 73% yield).

Step 4: Ethyl 2-(1-(4-(5-(trifluoromethyl)-1,2,4-oxadiazol-3-yl)phenyl)-1H-imidazol-4-yl)acetate (Compound No. 1)

To a stirred solution of ethyl 2-(1-(4-(N'-hydroxycarbamimidoyl)phenyl)-1H-imidazol-4-yl)acetate (7.5 g, 26 mmol) in tetrahydrofuran (40 mL), trifluoroacetic anhydride (4.04 mL, 27 mmol) was added drop wise at 0-5° C. under nitrogen atmosphere. The resulting reaction mixture was stirred for 16 h at 25° C. After completion of the reaction, the reaction mixture was slowly poured into ice-cold aqueous saturated solution of sodium bicarbonate (100 mL) and extracted with ethyl acetate (350 mL). The ethyl acetate layer was dried over anhydrous sodium sulphate and concentrated under reduced pressure to obtain the crude product. The crude product was purified by column chromatography on silica gel using 30% ethyl acetate in hexane as eluent to obtain ethyl 2-(1-(4-(5-(trifluoromethyl)-1,2,4-oxadiazol-3-yl)phenyl)-1H-imidazol-4-yl)acetate (3.5 g, 37% yield). $^{1}$H-NMR (400 MHz, DMSO-d6) δ 8.36 (d, 1H), 8.16 (dt, 2H), 7.91 (dt, 2H), 7.73 (t, 1H), 4.10 (q, 2H), 3.61 (s, 2H), 1.20 (t, 3H); LCMS (M+H): 367.35.

Step-5: N-(4-methoxyphenyl)-2-(1-(4-(5-(trifluoromethyl)-1,2,4-oxadiazol-3-yl)phenyl)-1H-imidazol-4-yl)acetamide (Compound No. 2)

To a stirred solution of 4-methoxyaniline (0.1 g, 0.8 mmol) in dichloromethane (4 mL), trimethylaluminium (25% w/w in hexane) (0.18 mL, 2.56 mmol) was added drop wise at 0-5° C. under nitrogen atmosphere. The obtained reaction mixture was stirred at 0-5° C. for 1.5 h followed by drop wise addition of ethyl 2-(1-(4-(5-(trifluoromethyl)-1,2,4-oxadiazol-3-yl)phenyl)-1H-imidazol-4-yl)acetate (0.3 g, 0.82 mmol) in dichloromethane (4 mL) at 0-5° C. The resulting reaction mixture was stirred at 25° C. for 16 h. The reaction mixture was quenched by methanol (5 mL) at 0-5° C. and extracted into ethyl acetate (20 mL) and further washed with saturated sodium bicarbonate solution (20 mL). The ethyl acetate layer was concentrated to obtain a crude product. The obtained crude product was purified using preparative HPLC to obtain N-(4-methoxyphenyl)-2-(1-(4-(5-(trifluoromethyl)-1,2,4-oxadiazol-3-yl)phenyl)-1H-imidazol-4-yl)acetamide (122 mg, 34% yield). H-NMR (400 MHz, DMSO-d6) δ 9.96 (s, 1H), 8.38 (d, 1H), 8.17 (dt, 2H), 7.92 (dt, 2H), 7.73 (s, 1H), 7.54-7.50 (i, 2H), 6.89-6.85 (mi, 2H), 3.71 (s, 3H), 3.59 (s, 2H); LCMS (M+H): 444.15.

The following compounds in table 1 were prepared by using the analogous procedure as described in example 1.

TABLE 1

| Compd no. | IUPAC name | Analytical data | Yield |
|---|---|---|---|
| 3 | 1-(pyrrolidin-1-yl)-2-(1-(4-(5-(trifluoromethyl)-1,2,4-oxadiazol-3-yl)phenyl)-1H-imidazol-4-yl)ethan-1-one | $^{1}$H-NMR (400 MHz, DMSO-d6) δ 8.35 (d, 1H), 8.15-8.17 (m, 2H), 7.91 (dd, 2H), 7.69 (s, 1H), 3.55-3.59 (m, 4H), 3.28 (d, 2H), 1.85-1.91 (m, 2H), 1.74-1.81 (m, 2H); LCMS(M + H) − 392.25 | 120 mg, 32% |
| 4 | N-benzyl-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 8.38-8.42 (m, 2H), 8.15-8.18 (m, 2H), 7.90 (dd, 2H), 7.68 (s, 1H), 7.21-7.33 (m, 5H), 4.29 (d, 2H), 3.46 (d, 2H); LCMS(M + H) − 427.75 | 0.115 g, 28% |
| 5 | N-(4-methoxybenzyl)-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 8.32-8.37 (m, 2H), 8.17 (dt, 2H), 7.88-7.91 (m, 2H), 7.66 (d, 1H), 7.19 (d, 2H), 6.87 (dt, 2H), 4.22 (d, 2H), 3.71 (s, 3H), 3.45 (s, 2H) ; LCMS(M + H) − 457.75 | 0.132 g, 30% |
| 6 | N-(4-fluorobenzyl)-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 8.37-8.44 (m, 2H), 8.17 (dt, 2H), 7.90 (dt, 2H), 7.68 (d, 1H), 7.29-7.32 (m, 2H), 7.13 (tt, 2H), 4.27 (d, 2H), 3.46 (s, 2H); LCMS(M + H) − 445.75 | 0.117 g, 27% |
| 7 | N-(2-fluorobenzyl)-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 8.38-8.44 (m, 2H), 8.15-8.18 (m, 2H), 7.90 (dd,, 2H), 7.68 (s, 1H), 7.27-7.37 (m, 2H), 7.14-7.18 (m, 2H), 4.33 (d, 2H), 3.48 (s, 2H); LCMS(M + H) − 445.80 | 0.151 g, 35% |
| 8 | N-(p-tolyl)-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 10.01 (s, 1H), 8.38 (d, 1H), 8.16-8.20 (m, 2H), 7.91-7.95 (m, 2H), 7.73 (s, 1H), 7.45 (dd, 2H), 7.09 (d, 2H), 3.60 (d, 2H), 2.53 (s, 1H), 2.23 (d, 3H); LCMS(M + H) − 428 | 0.225 g, 64% |
| 9 | N-(4-chlorophenyl)-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 10.26 (s, 1H), 8.38 (d, 1H), 8.15-8.18 (m, 2H), 7.91-7.93 (m, 2H), 7.75 (s, 1H), 7.63-7.66 (m, 2H), 7.35 (dt, 2H), 3.63 (s, 2H); | 0.210 g, 57% |
| 10 | N-(3-fluorophenyl)-2-(1-(4-(5-(trifluoromethyl)-1,2,4-oxadiazol-3-yl)phenyl)-1H-imidazol-4-yl)acetamide | $^{1}$H-NMR (400 MHz, DMSO-d6) δ 10.34 (s, 1H), 8.39 (d, 1H), 8.15-8.18 (m, 2H), 7.91-7.94 (m, 2H), 7.75 (s, 1H), 7.61-7.64 (m, 1H), 7.30-7.36 (m, 2H), 6.84-6.89 (m, 1H), 3.64 (s, 2H); LCMS(M + H) − 432 | 0.140 g, 40% |

TABLE 1-continued

| Compd no. | IUPAC name | Analytical data | Yield |
| --- | --- | --- | --- |
| 11 | 1-(piperidin-1-yl)-2-(1-(4-(5-(trifluoromethyl)-1,2,4-oxadiazol-3-yl)phenyl)-1H-imidazol-4-yl)ethan-1-one | $^1$H-NMR (400 MHz, DMSO-d6) δ 8.36 (d, 1H), 8.16 (dt, 2H), 7.91 (dt, 2H), 7.68 (d, 1H), 3.62 (d, 2H), 3.52 (t, 2H), 3.42-3.45 (m, 2H), 1.55 (q, 2H), 1.41-1.47 (m, 4H); LCMS(M + H) − 406.10 | 0.110 g, 33% |
| 12 | N-(3-methoxyphenyl)-2-(1-(4-(5-(trifluoromethyl)-1,2,4-oxadiazol-3-yl)phenyl)-1H-imidazol-4-yl)acetamide | $^1$H-NMR (400 MHz, DMSO-d6) δ 10.10 (s, 1H), 8.38 (d, 1H), 8.15-8.18 (m, 2H), 7.93 (dd, 2H), 7.74 (s, 1H), 7.33 (t, 1H), 7.19 (t, 1H), 7.13 (d, 1H), 6.62 (dt, 1H), 3.71 (s, 3H), 3.62 (s, 2H); LCMS(M + H) − 444.05 | 0.105 g, 29% |
| 13 | N-(pyridin-3-yl)-2-(1-(4-(5-(trifluoromethyl)-1,2,4-oxadiazol-3-yl)phenyl)-1H-imidazol-4-yl)acetamide | $^1$H-NMR (400 MHz, DMSO-d6) δ 10.34 (s, 1H), 8.76 (d, 1H), 8.39 (d, 1H), 8.25 (dd, 1H), 8.16-8.18 (m, 2H), 8.04-8.07 (m, 1H), 7.93 (d, 2H), 7.76 (s, 1H), 7.34 (dd, 1H), 3.67 (s, 2H), 2.53 (s, 1H); LCMS(M + H) − 414.95 | 0.185 g, 55% |
| 14 | N-(2-bromophenyl)-2-(1-(4-(5-(trifluoromethyl)-1,2,4-oxadiazol-3-yl)phenyl)-1H-imidazol-4-yl)acetamide | $^1$H-NMR (400 MHz, DMSO-d6) δ 9.66 (s, 1H), 8.48 (d, 1H), 8.18 (dd, 2H), 7.93 (dd, 2H), 7.87 (d, 1H), 7.81 (s, 1H), 7.64 (dd, 1H), 7.34-7.38 (m, 1H), 7.07-7.11 (m, 1H), 3.72 (s, 2H); LCMS(M + H) − 491.95 | 0.115 g, 29% |
| 15 | N-phenyl-2-(1-(4-(5-(trifluoromethyl)-1,2,4-oxadiazol-3-yl)phenyl)-1H-imidazol-4-yl)acetamide | $^1$H-NMR (400 MHz, DMSO-d6) δ 10.11 (s, 1H), 8.39 (s, 1H), 8.17 (dt, 2H), 7.92-7.94 (m, 2H), 7.75 (s, 1H), 7.61 (dd, 2H), 7.27-7.31 (m, 2H), 7.03 (t, 1H), 3.62 (d, 2H); LCMS(M + H) − 414.051 | 0.169 g, 50% |
| 16 | N-(5-methoxy-2-methylphenyl)-2-(1-(4-(5-(trifluoromethyl)-1,2,4-oxadiazol-3-yl)phenyl)-1H-imidazol-4-yl)acetamide | $^1$H-NMR (400 MHz, DMSO-d6) δ 9.45 (s, 1H), 8.46 (d, 1H), 8.18 (dt, 2H), 7.93 (dd, 2H), 7.78 (s, 1H), 7.26 (d, 1H), 7.09 (d, 1H), 6.63 (dd, 1H), 3.68 (d, 5H), 2.15 (s, 3H); LCMS(M + H) − 458.10 | 0.115 g, 31% |
| 17 | N-(4-fluoro-2-methoxyphenyl)-2-(1-(4-(5-(trifluoromethyl)-1,2,4-oxadiazol-3-yl)phenyl)-1H-imidazol-4-yl)acetamide | $^1$H-NMR (400 MHz, DMSO-d6) δ 9.51 (s, 1H), 8.47 (d, 1H), 8.16-8.19 (m, 2H), 8 (dd, 1H), 7.93 (dd, 2H), 7.77 (s, 1H), 6.96 (dd, 1H), 6.72 (td, 1H), 3.84 (s, 3H), 3.69 (s, 2H); LCMS(M + H) − 462.10 | 0.205 g, 55% |

Example 2: Preparation of N-((3-fluorophenyl)(methyl)(oxo)-$\lambda^6$-sulfanylidene)-1-(4-(5-(trifluoromethyl)-1,2,4-oxadiazol-3-yl)phenyl)-1H-pyrazole-4-carboxamide (Compound No. 23)

Step 1: ethyl 1-(4-cyanophenyl)-1H-pyrazole-4-carboxylate

To a stirred solution of 4-fluorobenzonitrile (1 g, 8.3 mmol) in N,N-dimethylformamide (15 mL), ethyl 1H-pyrazole-4-carboxylate (1.157 g, 8.3 mmol) and cesium carbonate (4.04 g, 12.38 mmol) were added at 25° C. The resulting reaction mixture was stirred at 70° C. for 16 h. The reaction mixture was cooled to 25° C. and filtered. The filtrate was poured on crushed ice (30 g). The obtained precipitate was filtered and washed with ice cold water (40 mL) and dried under reduced pressure to obtain ethyl 1-(4-cyanophenyl)-1H-pyrazole-4-carboxylate (1.4 g, 70% yield).

Step 2: ethyl 1-(4-(N'-hydroxycarbamimidoyl)phenyl)-1H-pyrazole-4-carboxylate A stirred suspension of ethyl 1-(4-cyanophenyl)-1H-pyrazole-4-carboxylate (0.5 g, 2.1 mmol) in ethanol (10 mL) was cooled to 5° C. 50% aqueous solution of hydroxylamine (0.137 g, 2.1 mmol) was added drop wise and stirred at 55° C. for 12 h. The reaction mixture was concentrated under reduced pressure to remove volatiles to obtain ethyl 1-(4-(N'-hydroxycarbamimidoyl)phenyl)-1H-pyrazole-4-carboxylate (0.57 g, 100% yield).

Step 3: 1-(4-(N'-hydroxycarbamimidoyl)phenyl)-1H-pyrazole-4-carboxylic acid

To a stirred suspension of ethyl 1-(4-(N'-hydroxycarbamimidoyl)phenyl)-1H-pyrazole-4-carboxylate (8 g, 29.2 mmol) in methanol (80 mL), a solution of sodium hydroxide (2.92 g, 72.9 mmol) in water (8 mL) was added at 25° C. and the resulting suspension was stirred at 55° C. for 5 h. The reaction mixture was concentrated under reduced pressure to remove volatiles and the obtained residue was dissolved in water (50 mL), acidified by 10% aqueous hydrochloride acid at 10° C. to pH 5 and obtained precipitate was filtered. The obtained solid was washed by water (30 mL) and dried under reduced pressure to obtain 1-(4-(N'-hydroxycarbamimidoyl)phenyl)-1H-pyrazole-4-carboxylic acid (7.2 g, 100% yield).

Step 4: 1-(4-(5-(trifluoromethyl)-1,2,4-oxadiazol-3-yl)phenyl)-1H-pyrazole-4-carboxylic acid To a stirred suspension of 1-(4-(N'-hydroxycarbamimidoyl)phenyl)-1H-pyrazole-4-carboxylic acid (7.1 g, 28.8 mmol) and dichloromethane (10 mL), trifluoroacetic anhydride (6.11 mL, 43.3 mmol) was added at 0° C. under nitrogen atmosphere and the resulting reaction mixture was stirred at 25° C. for 14 h. The reaction mixture was concentrated under reduced pressure to remove volatiles completely. The obtained residue was stirred in a 1:1 mixture of dichloromethane and hexane (40 mL) for 30 min at 25° C. The obtained precipitate was filtered and dried under reduced pressure. The solid product was stirred in water (40 mL) for 1 h and to this solution, a solution of sodium bicarbonate (1.696 g, 20.2 mmol) and water (10 mL) was added at 25° C. The precipitate was filtered and dried under reduced pressure to obtain 1-(4-(5-(trifluoromethyl)-1,2,4-oxadiazol-3-yl)phenyl)-1H-pyrazole-4-carboxylic acid (9 g, 96% yield).

Step 5: N-((3-fluorophenyl)(methyl)(oxo)-$\lambda^6$-sulfanylidene)-1-(4-(5-(trifluoromethyl)-1,2,4-oxadiazol-3-yl)phenyl)-1H-pyrazole-4-carboxamide To a stirred solution of (3-fluorophenyl)(imino)(methyl)-$\lambda^6$-sulfanone (0.107 g, 0.6 mmol), 1-(4-(5-(trifluoromethyl)-1,2,4-oxadiazol-3-yl)phenyl)-1H-pyrazole-4-carboxylic acid (0.20 g, 0.6 mmol), N,N-diisopropylethylamine (0.269 mL, 1.5 mmol) and N,N-dimethylformamide (5 mL), 1-[Bis(dimethylamino)methylene]-1H-1,2,3-triazolo[4,5-b]pyridinium 3-oxide hexafluorophosphate (HATU) (0.352 g, 0.9 mmol) was added at 5-10° C. and the resulting reaction mixture was stirred at 25° C. for 16 h. To this reaction mixture, ice cold aqueous saturated sodium bicarbonate solution (10 mL) was added and stirred for 30 min at 25° C. The obtained precipitate was filtered, washed with water (5 mL) and dried. The crude product was purified by prep HPLC to obtain N-((3-fluorophenyl)(methyl)(oxo)-$\lambda^6$-sulfanylidene)-1-(4-(5-(trifluoromethyl)-1,2,4-oxadiazol-3-yl)phenyl)-1H-pyrazole-4-carboxamide (0.096 g, 33% yield). $^1$H-NMR (400 MHz, DMSO-d6) δ 9.07 (d, s,), 8.19 (s, 4H), 8.13 (d, 1H), 7.91-7.93 (n 2H), 7.74-7.79 (m, 1H), 7.63-7.68 (m, 1H), 3.65 (s, 3H); LCMS (M+H): 479.75.

The following compounds in table 2 were prepared by using the analogous procedure as described in example 2.

TABLE 2

| Compd no. | IUPAC name | Analytical data | Yield |
|---|---|---|---|
| 18 | N-(4-oxido-1,4-$\lambda^6$-oxathian-4-ylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.06 (s, 1H), 8.19 (s, 4H), 8.11 (s, 1H), 4.16 (td, 2H), 3.93-3.98 (m, 2H), 3.78-3.82 (m, 2H), 3.57-3.63 (m, 2H); LCMS (M + H): 442.05 | 0.21 g, 62% |
| 19 | N-(methyl(oxo)(o-tolyl)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.04 (s, 1H), 8.19 (s, 4H), 8.12 (d, 1H), 8.04 (d, 1H), 7.64 (t, 1H), 7.47-7.54 (m, 2H), 3.57 (s, 3H), 2.63 (s, 3H); LCMS (M + H): 476.05 | 0.11 g, 30% |
| 20 | N-((2-methoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9 (s, 1H), 8.16-8.21 (m, 4H), 8.07 (d, 1H), 8 (dd, 1H), 7.71-7.75 (m, 1H), 7.32 (d, 1H), 7.22-7.26 (m, 1H), 3.90 (s, 3H), 3.59 (s, 3H); LCMS (M + H): 492.05 | 0.1 g, 26% |
| 21 | N-((4-methoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.05 (s, 1H), 8.19 (s, 4H), 8.12 (s, 1H), 8 (dd, 2H), 7.21 (dd, 2H), 3.87 (s, 3H), 3.57 (s, 3H); LCMS (M + H): 492 | 0.11 g, 29% |
| 22 | N-(methyl(oxo)(phenyl)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.06 (s, 1H), 8.18 (d, 4H), 8.12 (s, 1H), 8.07 (d, 2H), 7.78 (t, 1H), 7.70 (t, 2H), 3.60 (s, 3H), 2.88 (s, 1H); LCMS (M + H): 462.05 | 0.12 g, 34% |
| 32 | N-((2,4-dimethoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 8.98 (s, 1H), 8.18 (s, 4H), 8.07 (d, 1H), 7.91 (d, 1H), 6.76-6.80 (m, 2H), 3.86-3.90 (m, 6H), 3.55 (s, 3H); LCMS (M + H): 522 | 0.09 g, 18% |
| 33 | N-((2,6-dichlorophenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.03 (d, 1H), 8.18 (s, 4H), 8.09 (s, 1H), 7.69-7.71 (m, 2H), 7.59-7.65 (m, 1H), 3.73 (s, 3H); LCMS (M + H): 529.85 | 0.09 g, 18% |
| 34 | N-(methyl(oxo)(pyridin-4-yl)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.07 (d, 1H), 8.95 (dd, 2H), 8.19 (s, 4H), 8.13 (d, 1H), 8.02 (dd, 2H), 3.67 (s, 3H); LCMS (M + H): 462.9 | 0.1 g, 30% |
| 35 | N-((2-methoxyethyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.02 (d, 1H), 8.19 (t, 4H), 8.08 (d, 1H), 3.81-3.94 (m, 4H), 3.42 (d, 3H), 3.30 (s, 3H); LCMS (M + H): 443.95 | 0.18 g, 44% |
| 36 | N-(diethyl(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9 (d, 1H), 8.16-8.21 (m, 4H), 8.07 (d, 1H), 3.51-3.62 (m, 4H), 1.33 (t, 6H); LCMS (M + H): 428 | 0.22 g, 54% |

TABLE 2-continued

| Compd no. | IUPAC name | Analytical data | Yield |
|---|---|---|---|
| 37 | N-(dimethyl(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9 (s. 1H), 8.19 (s, 4H), 8.06 (s, 1H), 3.44 (s, 6H); LCMS (M + H): 399 | 0.17 g, 45% |
| 38 | N-((4-chlorophenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide | $^1$H-NMR (400 MHz, DMSO-d6) δ 9.06 (d, 1H), 8.20 (d, H), 8.12 (s, 1H), 8.07 (dt, 2H), 7.78 (dt, 2H), 3.62 (s, 3H); LCMS (M + H): 496 | 0.12 g, 26% |

Example 3: Preparation of 4-chloro-N-((1-(4-(5-(trifluoromethyl)-1,2,4-oxadiazol-3-yl)phenyl)-1H-pyrazol-4-yl)methyl)benzamide (Compound No. 104)

Step 1: 4-(1H-pyrazol-1-yl)benzonitrile

To a stirred solution of 1H-pyrazole (10 g, 147 mmol) in N,N-dimethylformamide (100 mL) cooled to 0° C., sodium hydride (5.87 g, 147 mmol) was added in portions under nitrogen atmosphere. The formed suspension was stirred at 0° C. for 30 minutes. 4-fluorobenzonitrile (17.8 g, 147 mmol) was added to the reaction mixture at 0° C. The resulting reaction mixture was brought to 25° C. and stirred for 16 h. After completion of the reaction, the reaction mixture was poured on ice cold water (500 mL). The solid obtained was filtered and dried under reduced pressure to obtain 4-(1H-pyrazol-1-yl)benzonitrile (22 g, 130 mmol, 89% yield) as white solid.

Step 2: 4-(4-formyl-1H-pyrazol-1-yl)benzonitrile

To a stirred solution of 4-(1H-pyrazol-1-yl)benzonitrile (19 g, 112 mmol) in trifluoroacetic acid (147 mL, 1909 mmol), hexamethylenetetramine (47.2 g, 337 mmol) was added in portions under nitrogen atmosphere. The reaction mixture was heated to 75° C. for 48 h under nitrogen atmosphere. After completion of the reaction, the reaction mixture was poured over ice cold solution of aqueous saturated sodium bicarbonate (300 mL) and product was extracted thrice with ethyl acetate (225 mL). The combined ethyl acetate layer was washed with water (100 mL). The ethyl acetate layer was dried over anhydrous sodium sulphate and evaporated under reduced pressure. The crude compound was purified by flash column chromatography using 30% ethyl acetate in hexane as an eluent to obtain 4-(4-formyl-1H-pyrazol-1-yl)benzonitrile (12.86 g, 65.2 mmol, 58% yield) as white solid.

Step 3: 4-(4-(hydroxymethyl)-1H-pyrazol-1-yl)benzonitrile

To a stirred solution of 4-(4-formyl-1H-pyrazol-1-yl)benzonitrile (12.9 g, 65.2 mmol) in tetrahydrofuran (60 mL) and methanol (60 mL), lithium chloride (0.276 g, 6.5 mmol) was added under nitrogen atmosphere at 25° C. The reaction mixture was cooled to 0° C. and sodium borohydride (3.7 g, 98 mmol) was added in portions. The reaction mixture was brought to 25° C. and stirred for 8 h. After completion of the reaction, the reaction mixture was cooled to 0° C. and water (50 mL) was added drop wise to the reaction mixture. The product was extracted thrice in dichloromethane (225 mL). The combined dichloromethane layer was dried over anhydrous sodium sulphate and evaporated under reduced pressure. The crude compound was purified by flash column chromatography using 75% ethyl acetate in hexane as an eluent to obtain 4-(4-(hydroxymethyl)-1H-pyrazol-1-yl)benzonitrile (10 g, 77% yield).

Step 4: 4-(4-(chloromethyl)-1H-pyrazol-1-yl)benzonitrile

To a stirred solution of 4-(4-(hydroxymethyl)-1H-pyrazol-1-yl)benzonitrile (7 g, 35 mmol) in chloroform (70 mL), thionyl chloride (3.1 mL, 42 mmol) was added drop wise at 25° C. under nitrogen atmosphere. The resulting reaction mixture was refluxed for 2-3 h at 68° C. The reaction mixture was brought to 25° C. and diluted with water (100 mL). The product was extracted thrice with dichloromethane (150 mL). The combined dichloromethane layer was washed with water (50 mL) and dried over anhydrous sodium sulphate. The dichloromethane layer was evaporated under reduced pressure to obtain 4-(4-(chloromethyl)-1H-pyrazol-1-yl)benzonitrile (7.48 g, 34.4 mmol, 98% yield) as cream solid. The crude compound obtained was taken to the next step as such.

Step 5: tert-butyl (tert-butoxycarbonyl)((1-(4-cyanophenyl)-1H-pyrazol-4-yl)methyl)carbamate To a stirred solution of di-tert-butyl iminodicarboxylate (7.5 g, 34 mmol) in N,N-dimethylformamide (70 mL), potassium carbonate (5.7 g, 41 mmol) was added in portions under nitrogen atmosphere. 4-(4-(chloromethyl)-1H-pyrazol-1-yl)benzonitrile (7.5 g, 34 mmol) was dissolved in N,N-dimethylformamide (5 mL) and added drop wise to the reaction mixture at 25° C. under nitrogen atmosphere. The reaction mixture was heated to 100° C. for 16 h under nitrogen atmosphere. The reaction mixture was diluted with water (100 mL). The product was extracted thrice with ethyl acetate (300 mL). The combined ethyl acetate layer was washed twice with ice cold water (400 mL). The ethyl acetate layer was dried over anhydrous sodium sulphate and evaporated under reduced pressure. The crude compound was purified by flash column chromatography using 65% ethyl acetate in hexane as an eluent to obtain tert-butyl (tert-butoxycarbonyl)((1-(4-cyanophenyl)-1H-pyrazol-4-yl)methyl)carbamate (12 g, 30 mmol, 88% yield) as colorless gum.

Step 6: tert-butyl (tert-butoxycarbonyl)((1-(4-(N'-hydroxycarbamimidoyl)phenyl)-1H-pyrazol-4-yl)methyl)carbamate To a stirred solution of tert-butyl (tert-butoxycarbonyl)((1-(4-cyanophenyl)-1H-pyrazol-4-yl)methyl)carbamate (12 g, 30.1 mmol) in ethanol (130 mL), 50% aqueous solution of hydroxylamine (3.7 mL, 60 mmol) was added at 25° C. and the resulting reaction mixture was heated to 80° C. for 16 h under nitrogen atmosphere. The reaction mixture was evaporated under reduced pressure to remove volatiles to obtain tert-butyl (tert-butoxycarbonyl)((1-(4-(N'-hydroxycarbamimidoyl)phenyl)-1H-pyrazol-4-yl)methyl)carbamate (12.5 g, 29 mmol, 96% yield) as cream solid.

Step 7: tert-butyl (tert-butoxycarbonyl)((1-(4-(5-(trifluoromethyl)-1,2,4-oxadiazol-3-yl)phenyl)-1H-pyrazol-4-yl)methyl)carbamate To a stirred solution of tert-butyl (tert-butoxycarbonyl)((1-(4-(N'-hydroxycarbamimidoyl)phenyl)-1H-pyrazol-4-yl)methyl)carbamate (12.5 g, 29.0 mmol) in tetrahydrofuran (130 mL), triethylamine (6 mL, 43 mmol) was added at 25° C. The reaction mixture was cooled to 0° C. To this reaction mixture, trifluoroacetic anhydride (6.1 mL, 43 mmol) was added drop wise and allowed to come to 25° C. followed by stirring at 25° C. for 16 h under nitrogen atmosphere. After completion of the reaction, the reaction mixture was diluted with water (100 mL) and product was extracted thrice with ethyl acetate (300 mL). The combined ethyl acetate layer was dried over anhydrous sodium sulphate and evaporated under reduced pressure. The crude compound was purified by flash column chromatography using 18% ethyl acetate in hexane as an eluent to obtain tert-butyl (tert-butoxycarbonyl)((1-(4-(5-(trifluoromethyl)-1,2,4-oxadiazol-3-yl)phenyl)-1H-pyrazol-4-yl)methyl)carbamate (10.5 g, 20.6 mmol, 71% yield) as white solid.

Step 8: (1-(4-(5-(trifluoromethyl)-1,2,4-oxadiazol-3-yl)phenyl)-1H-pyrazol-4-yl)methanamine hydrochloride To a stirred solution of tert-butyl (tert-butoxycarbonyl)((1-(4-(5-(trifluoromethyl)-1,2,4-oxadiazol-3-yl)phenyl)-1H-pyrazol-4-yl)methyl)carbamate (10.5 g, 20.6 mmol) in dichloromethane (100 mL) cooled at 0° C., 4M hydrochloric acid in dioxane (70 mL, 280 mmol) was added drop wise and the resulting reaction mixture was stirred at 25° C. for 12 h under nitrogen atmosphere. After completion of the reaction, the solid formed in the reaction mixture was filtered. The solid was washed thrice with n-hexane (150 mL) and dried under reduced pressure to obtain (1-(4-(5-(trifluoromethyl)-1,2,4-oxadiazol-3-yl)phenyl)-1H-pyrazol-4-yl)methanamine hydrochloride (6.5 g, 18.7 mmol, 91% yield) as white solid.

Step 9: 4-chloro-N-((1-(4-(5-(trifluoromethyl)-1,2,4-oxadiazol-3-yl)phenyl)-1H-pyrazol-4-yl)methyl) benzamide (Compound No. 104)

To a stirred solution of (1-(4-(5-(trifluoromethyl)-1,2,4-oxadiazol-3-yl)phenyl)-1H-pyrazol-4-yl)methanamine hydrochloride (0.11 g, 0.32 mmol) and 4-chlorobenzoic acid (0.05 g, 0.3 mmol) in N,N-dimethyl formamide (10 mL), N,N-diisopropylethylamine (0.22 mL, 1.28 mmol) was added at 25° C. followed by 1-[Bis(dimethylamino)methylene]-1H-1,2,3-triazolo[4,5-b]pyridinium 3-oxide hexafluorophosphate (HATU) (0.24 g, 0.6 mmol). The resulting reaction mixture was stirred at 25° C. under nitrogen atmosphere for 16 h. After completion of the reaction, the reaction mixture was diluted with water (20 mL). The product was extracted thrice by ethyl acetate (60 mL). The combined ethyl acetate layer was washed thrice with ice cold water (60 mL), dried over anhydrous sodium sulphate and evaporated under reduced pressure. The crude compound was purified by flash column chromatography using 51% ethyl acetate in hexane as an eluent to obtain 4-chloro-N-((1-(4-(5-(trifluoromethyl)-1,2,4-oxadiazol-3-yl)phenyl)-1H-pyrazol-4-yl)methyl)benzamide (0.065 g, 0.15 mmol, 46% yield) as white solid. H-NMR (400 MHz, DMSO-d6) δ 9 (t, H), 8.57 (s, H), 8.17-8.14 (m, 2H), 8.08-8.02 (m, 2H), 7.92-7.86 ((2H), 7.79 (s, 1H), 7.56-7.51 (q, 2H), 4.43 (dd, 2H); LCMS: m/e 448 (M+H).

The following compounds in table 3 were prepared by using the analogous procedure as described in example 3.

TABLE 3

| Compd. No. | IUPAC Name | Analytical Data | Yield |
|---|---|---|---|
| 105 | N-((1-(4-(5-(trifluoromethyl)-1,2,4-oxadiazol-3-yl)phenyl)-1H-pyrazol-4-yl)methyl)acetamide | $^1$H-NMR (400 MHz, DMSO-d6) δ 8.51 (d, 1H), 8.23 (t, 1H), 8.16 (dt, 2H), 8.06 (dt, 2H), 7.73 (s, 1H), 4.18 (d, 2H), 1.84 (s, 3H); LCMS: m/e 352 (M + H) | 135 mg, 66% |
| 106 | N-((1-(4-(5-(trifluoromethyl)-1,2,4-oxadiazol-3-yl)phenyl)-1H-pyrazol-4-yl)methyl)propionamide | $^1$H-NMR (400 MHz, DMSO-d6) δ 8.50 (d, 1H), 8.18-8.13 (m, 3H), 8.05 (dt, 2H), 7.72 (s, 1H), 4.18 (d, 2H), 2.12 (q, 2H), 1.01 (t, 3H); LCMS: m/e 366 (M + H) | 200 mg, 95% |
| 107 | 2-fluoro-N-((1-(4-(5-(trifluoromethyl)-1,2,4-oxadiazol-3-yl)phenyl)-1H-pyrazol-4-yl)methyl)benzamide | $^1$H-NMR (400 MHz, DMSO-d6) δ 8.77 (t, 1H), 8.56 (s, 1H), 8.17 (dt, 2H), 8.07 (dt, 2H), 7.79 (s, 1H), 7.66 (td, 1H), 7.55-7.49 (m, 1H), 7.32-7.25 (m, 2H), 4.41 (d, 2H); LCMS: m/e 432 (M + H) | 180 mg, 72% |
| 108 | 4-fluoro-N-((1-(4-(5-(trifluoromethyl)-1,2,4-oxadiazol-3-yl)phenyl)-1H-pyrazol-4-yl)methyl)benzamide | $^1$H-NMR (400 MHz, DMSO-d6) δ 8.94 (t, 1H), 8.57 (s, 1H), 8.16 (dt, 2H), 8.07 (dt, 2H), 7.98-7.92 (m, 2H), 7.79 (s, 1H), 7.33-7.24 (m, 2H), 4.41 (d, 2H); LCMS: m/e 432 (M + H) | 160 mg, 64% |
| 109 | 2-methyl-N-((1-(4-(5-(trifluoromethyl)-1,2,4-oxadiazol-3-yl)phenyl)-1H-pyrazol-4-yl)methyl)thiazole-5-carboxamide | $^1$H-NMR (400 MHz, DMSO-d6) δ 9.01 (t, 1H), 8.57 (s, 1H), 8.22 (s, 1H), 8.16 (dd, 2H), 8.07 (dd, 2H), 7.79 (s, 1H), 4.38 (d, 2H), 2.65 (s, 3H); LCMS: m/e 435 (M + H) | 210 mg, 84% |

TABLE 3-continued

| Compd. No. | IUPAC Name | Analytical Data | Yield |
|---|---|---|---|
| 110 | N-((1-(4-(5-(trifluoromethyl)-1,2,4-oxadiazol-3-yl)phenyl)-1H-pyrazol-4-yl)methyl)cyclobutanecarboxamide | $^1$H-NMR (400 MHz, DMSO-d6) δ 8.49 (d, 1H), 8.16 (dt, 2H), 8.07-8.03 (m, 3H), 7.71 (s, 1H), 4.18 (d, 2H), 3.06-2.98 (m, 1H), 2.19-2.09 (m, 2H), 2.05-1.97 (m, 2H), 1.93-1.83 (m, 1H), 1.81-1.71 (m, 1H); LCMS: m/e 392 (M + H) | 175 mg, 77% |
| 111 | N-((1-(4-(5-(trifluoromethyl)-1,2,4-oxadiazol-3-yl)phenyl)-1H-pyrazol-4-yl)methyl)nicotinamide | $^1$H-NMR (400 MHz, DMSO-d6) δ 9.12 (t, 1H), 9.04 (q, 1H), 8.70 (dd, 1H), 8.59 (d, 1H), 8.23-8.20 (m, 1H), 8.16 (dt, 2H), 8.08 (dt, 2H), 7.81 (s, 1H), 7.51 (ddd, 1H), 4.44 (d, 2H) | 170 mg, 71% |

Example 4: Preparation of N-((1-(4-(5-(trifluoromethyl)-1,2,4-oxadiazol-3-yl)phenyl)-1H-pyrazol-4-yl)methyl)methanesulfonamide (Compound No. 112)

To a stirred solution of (1-(4-(5-(trifluoromethyl)-1,2,4-oxadiazol-3-yl)phenyl)-1H-pyrazol-4-yl)methanamine hydrochloride (0.2 g, 0.58 mmol) in dichloromethane (10 mL), triethylamine (0.24 mL, 1.7 mmol) was added at 25 TC. The reaction mixture was cooled to 0° C. Methanesulfonyl chloride (0.045 mL, 0.6 mmol) was added drop wise at 0 TC. The resulting reaction mixture was brought to 25° C. and stirred for 16 h under nitrogen atmosphere. After completion of the reaction, the reaction mixture was diluted with water (20 mL). The product was extracted thrice with dichloromethane (60 mL). The combined dichloromethane layer was washed with water (20 mL), dried over anhydrous sodium sulphate and evaporated under reduced pressure. The crude compound was purified by flash column chromatography using 60% ethyl acetate in hexane as an eluent to obtain N-((1-(4-(5-(trifluoromethyl)-1,2,4-oxadiazol-3-yl)phenyl)-1H-pyrazol-4-yl)methyl)methanesulfonamide (0.14 g, 0.4 mmol, 62% yield) as white solid. $^1$H-NMR (400 MHz, DMSO-d6) δ 8.59 (s, 1H), 8.17 (dt, 9.2, 2.1, 2H), 8.07 (dt, 9.1, 2.1, 2H), 7.81 (s, 1H), 7.43 (t, 6.0, 1H), 4.13 (d, 6.1, 2H), 2.91 (s, 3H); LCMS: m/e 388 (M+H).

The following compounds in table 4 were prepared by using the analogous procedure as described in example 4.

TABLE 4

| Compd. No. | IUPAC Name | Analytical Data | Yield |
|---|---|---|---|
| 113 | N-((1-(4-(5-(trifluoromethyl)-1,2,4-oxadiazol-3-yl)phenyl)-1H-pyrazol-4-yl)methyl)ethanesulfonamide | $^1$H-NMR (400 MHz, DMSO-d6) δ 8.58 (s, 1H), 8.18 (dt, 2H), 8.08-8.05 (m, 2H), 7.80 (s, 1H), 7.48 (t, 1H), 4.10 (d, 2H), 2.99 (q, 2H), 1.17 (t, 3H); LCMS: m/e 402 (M + H) | 70 mg, 30% |
| 114 | N-((1-(4-(5-(trifluoromethyl)-1,2,4-oxadiazol-3-yl)phenyl)-1H-pyrazol-4-yl)methyl)cyclopropanesulfonamide | $^1$H-NMR (400 MHz, DMSO-d6) δ 8.58 (s, 1H), 8.17 (dd, 2H), 8.06 (dd,2H), 7.81 (s, 1H), 7.50 (t, 1H), 4.16 (d, 2H), 2.57-2.52 (m, 1H), 0.92-0.89 (m, 4H); LCMS: m/e 414 (M + H) | 210 mg, 88% |
| 115 | 2-fluoro-N-((1-(4-(5-(trifluoromethyl)-1,2,4-oxadiazol-3-yl)phenyl)-1H-pyrazol-4-yl)methyl)benzenesulfonamide | $^1$H-NMR (400 MHz, DMSO-d6) δ 8.35 (t,lH), 8.31 (s, 1H), 8.17-8.14 (m, 2H), 7.94 (d, 2H), 7.78 (td, 1H), 7.64-7.56 (m, 2H), 7.35-7.29 (m, 2H), 4.08 (d, 2H); LCMS: m/e 468 (M + H) | 250 mg, 92% |
| 116 | 5-chloro-N-((1-(4-(5-(trifluoromethyl)-1,2,4-oxadiazol-3-yl)phenyl)-1H-pyrazol-4-yl)methyl)thiophene-2-sulfonamide | $^1$H-NMR (400 MHz, DMSO-d6) δ 8.45 (s, 1H), 8.41 (s, 1H), 8.18-8.16 (m, 2H), 8.02-8 (m, 2H), 7.67 (s, 1H), 7.48 (d, 1H), 7.21 (d, 1H), 4.07 (d, 2H); LCMS: m/e 490 (M + H) | 220 mg, 78% |
| 117 | 4-fluoro-N-((1-(4-(5-(trifluoromethyl)-1,2,4-oxadiazol-3-yl)phenyl)-1H-pyrazol-4-yl)methyl)benzenesulfonamide | $^1$H-NMR (400 MHz, DMSO-d6) δ 8.38 (d, 1H), 8.16 (dt, 2H), 8.08 (t, 1H), 7.98 (dt, 2H), 7.87-7.82 (m, 2H), 7.59 (s, 1H), 7.41-7.35 (m, 2H), 3.97 (d, 2H); LCMS: m/e 468 (M + H) | 260 mg, 96% |
| 118 | N-((1-(4-(5-(trifluoromethyl)-1,2,4-oxadiazol-3-yl)phenyl)-1H-pyrazol-4-yl)methyl)pyridine-3-sulfonamide | $^1$H-NMR (400 MHz, DMSO-d6) δ 8.93 (dd, 1H), 8.74 (dd, 1H), 8.41 (s, 1H), 8.30 (t, 1H), 8.13-8.17 (m, 3H), 7.97 (dd, 2H), 7.59-7.55(m, 2H), 4.04 (d, 2H); LCMS: m/e 451 (M + H) | 130 mg, 50% |

Example 5: Preparation of 1-(pyridin-3-yl)-3-((1-(4-(5-(trifluoromethyl)-1,2,4-oxadiazol-3-yl)phenyl)-1H-pyrazol-4-yl)methyl)urea (Compound no 119)

To a stirred solution of (1-(4-(5-(trifluoromethyl)-1,2,4-oxadiazol-3-yl)phenyl)-1H-pyrazol-4-yl)methanamine hydrochloride (0.2 g, 0.6 mmol) in dichloromethane (10 mL), triethylamine (0.12 mL, 0.9 mmol) was added. The obtained mixture was cooled to 0° C. and 3-isocyanatopyridine (0.069 g, 0.6 mmol) was added. The resulting reaction mixture was brought to 25° C. and stirred for 16 h under nitrogen atmosphere. After completion of the reaction, the reaction mixture was evaporated under reduced pressure to dryness. The crude compound was purified by preparative HPLC to obtain 1-(pyridin-3-yl)-3-((1-(4-(5-(trifluoromethyl)-1,2,4-oxadiazol-3-yl)phenyl)-1H-pyrazol-4-yl) methyl)urea (0.15 g, 0.3 mmol, 58% yield) as cream solid. $^1$H-NMR (400 MHz, DMSO-d6) δ 8.71 (d, 1H), 8.54 (s, 2H), 8.16 (dt, 2H), 8.11 (dd, 1H), 8.07 (dt, 2H), 7.90 (dq, 1H), 7.78 (s, 1H), 7.25 (q, 1H), 6.68 (t, 1H), 4.25 (d, 2H); LCMS: m/e 430 (M+H).

The following compounds in table 5 were prepared by using the analogous procedure as described in example 5.

TABLE 5

| Compd. No. | IUPAC Name | Analytical Data | Yield |
|---|---|---|---|
| 120 | 1-(2-fluorophenyl)-3-((1-(4-(5-(trifluoromethyl)-1,2,4-oxadiazol-3-yl-phenyl)-1H-pyrazol-4-yl)methyl)urea | $^1$H-NMR (400 MHz, DMSO-d6) δ 8.56 (s, 1H), 8.32 (d, 1H), 8.18-8.12 (m, 3H), 8.08-8.06 (m, 2H), 7.79 (s, 1H), 7.17 (ddd, 1H), 7.08 (t, 1H), 6.97-6.89 (m, 2H), 4.25 (d, 2H); LCMS: m/e 447 (M + H) | 130 mg, 50% |

Example 6: Preparation of N-(methyl(oxo)(m-tolyl)-λ$^6$-sulfanylidene)-1-(4-(5-(trifluoromethyl)-1,2,4-oxadiazol-3-yl)phenyl)-1H-pyrrole-3-carboxamide (Compound No. 24)

Step 1: methyl 1H-pyrrole-3-carboxylate

To a stirred solution of 1H-pyrrole-3-carboxylic acid (6 g, 54 mmol) in N,N-dimethylformamide (60 mL), potassium carbonate (8.96 g, 64.8 mmol) was added followed by the addition of methyl iodide (3.4 mL, 54 mmol) and the resulting reaction mixture was stirred at 25° C. for 2 h under nitrogen atmosphere. After completion of the reaction, water (50 mL) was added to the reaction mixture and extracted thrice with ethyl acetate (150 mL). The combined ethyl acetate layer was washed thrice by ice cold water (225 mL). The ethyl acetate layer was dried over anhydrous sodium sulphate and evaporated under reduced pressure to obtain methyl 1H-pyrrole-3-carboxylate (6.5 g, 52 mmol, 96% yield).

Step 2: methyl 1-(4-cyanophenyl)-1H-pyrrole-3-carboxylate

To a stirred solution of 4-fluorobenzonitrile (6.5 g, 53.7 mmol) in N,N-dimethylformamide (60 mL), methyl 1H-pyrrole-3-carboxylate (6.7 g, 54 mmol) and cesium carbonate (44 g, 134 mmol) were added. The resulting reaction mixture was heated for 12 h at 80° C. under nitrogen atmosphere. After completion of the reaction, the reaction mixture was diluted by water (60 mL) and product was extracted thrice by ethyl acetate (150 mL). The combined ethyl acetate layer was washed thrice with ice cold water (150 mL). The ethyl acetate layer was dried over anhydrous sodium sulphate and evaporated under reduced pressure to obtain methyl 1-(4-cyanophenyl)-1H-pyrrole-3-carboxylate (8.8 g, 38.9 mmol, 72% yield) as light brown solid.

Step 3: 1-(4-cyanophenyl)-1H-pyrrole-3-carboxylic acid

To a stirred solution of methyl 1-(4-cyanophenyl)-1H-pyrrole-3-carboxylate (8.8 g, 39 mmol) in mixture of tetrahydrofuran (120 mL) and methanol (26 mL), cooled at 0° C., lithium hydroxide (2.8 g, 117 mmol) dissolved in water (26 mL) was added drop wise. The resulting reaction mixture was heated to 50° C. for 5 h under nitrogen atmosphere. After completion of the reaction, the reaction mixture was acidified to pH 4 using 10% aqueous hydrochloric acid solution. The solid precipitated out was filtered and dried under reduced pressure to obtain 1-(4-cyanophenyl)-1H-pyrrole-3-carboxylic acid (7.2 g, 34 mmol, 87% yield) as white solid. The crude compound was taken as such for next step without purification.

Step 4: 1-(4-(N'-hydroxycarbamimidoyl)phenyl)-1H-pyrrole-3-carboxylic acid

To a stirred solution of 1-(4-cyanophenyl)-1H-pyrrole-3-carboxylic acid (3.5 g, 16.5 mmol) in ethanol (30 mL), 50% aqueous solution of hydroxylamine (1.52 mL, 24.7 mmol) was added at 25° C. The reaction mixture was stirred at 80° C. for 12 h under nitrogen atmosphere. After completion of the reaction, the reaction mixture was brought to 25° C. and evaporated to dryness under reduced pressure to obtain 1-(4-(N'-hydroxycarbamimidoyl)phenyl)-1H-pyrrole-3-carboxylic acid (4 g, 16.3 mmol, 99% yield) as white solid.

Step 5: 1-(4-(5-(trifluoromethyl)-1,2,4-oxadiazol-3-yl)phenyl)-1H-pyrrole-3-carboxylic acid To a stirred solution of 1-(4-(N'-hydroxycarbamimidoyl) phenyl)-1H-pyrrole-3-carboxylic acid (4 g, 16 mmol) in tetrahydrofuran (50 mL), trifluoroacetic anhydride (3.5 mL, 24.5 mmol) was added drop wise at 0° C. The resulting reaction mixture was brought to 25° C. and stirred for 12 h under nitrogen atmosphere. After completion of the reaction, the reaction mixture was diluted by water and product was extracted thrice by ethyl acetate (180 mL). The combined ethyl acetate layer was dried over anhydrous sodium sulphate and evaporated under reduced pressure. The crude compound was purified by flash column chromatography using 75% ethyl acetate in hexane as an eluent to obtain 1-(4-(5-(trifluoromethyl)-1,2,4-oxadiazol-3-yl)phenyl)-1H-pyrrole-3-carboxylic acid (5 g, 15.5 mmol, 95% yield) as cream solid.

Step 6: N-(methyl(oxo)(m-tolyl)-λ$^6$-sulfanylidene)-1-(4-(5-(trifluoromethyl)-1,2,4-oxadiazol-3-yl)phenyl)-1H-pyrrole-3-carboxamide (Compound No. 24)

To a stirred solution of 1-(4-(5-(trifluoromethyl)-1,2,4-oxadiazol-3-yl)phenyl)-1H-pyrrole-3-carboxylic acid (0.4 g, 1.24 mmol) in dichloromethane (10 mL), imino(methyl)(m-tolyl)-λ$^6$-sulfanone (0.21 g, 1.2 mmol) and 4-dimethylaminopyridine (0.23 g, 1.9 mmol) were added at 25° C. The reaction mixture was cooled to 0° C. and 1-(3-Dimethylaminopropyl)-3-ethylcarbodiimide hydrochloride (0.36 g, 1.9 mmol) was added to reaction mixture. The reaction mixture was stirred at 25° C. for 12 h under nitrogen atmosphere. After completion of the reaction, the reaction mixture was quenched by water (10 mL). The product was extracted thrice with ethyl acetate (60 mL). The combined ethyl acetate layer was washed thrice with ice cold water (60 mL). The ethyl acetate layer was dried over anhydrous sodium sulphate and evaporated under reduced pressure. The crude compound was purified by flash column chromatography using 80% ethyl acetate in hexane as an eluent to obtain N-(methyl(oxo)(m-tolyl)-$\lambda^6$-sulfanylidene)-1-(4-(5-(trifluoromethyl)-1,2,4-oxadiazol-3-yl)phenyl)-1H-pyrrole-3-carboxamide (0.1 g, 0.2 mmol, 18% yield) as colorless gum. $^1$H-NMR (400 MHz, DMSO-d6) δ 8.17-8.13 (m, 2H), 8 (dd, 1H), 7.94 (dd, 2H), 7.83-7.81 (m, 2H), 7.59-7.53 (m, 3H), 6.64 (q, 1H), 3.52 (s, 3H), 2.43 (s, 3H); LCMS: m/e 475 (M+H).

The following compounds in table 6 were prepared by using the analogous procedure as described in example 6.

TABLE 6

| Compd. No. | IUPAC Name | Analytical Data | Yield |
|---|---|---|---|
| 25 | N-((2-methoxyethyl)(oxo)(pyridin-2-yl)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.73 (dq, 1H), 8.22 (dt, 1H), 8.19-8.11 (m, 3H), 8 (dd, 1H), 7.96-7.93 (m, 2H), 7.75-7.68 (m, 1H), 7.53 (dd, 1H), 6.61 (q, 1H), 4.09-3.99 (m, 1H), 3.97-3.90 (m, 1H), 3.86-3.77 (m, 1H), 3.75-3.67 (m, 1H), 3.03-3 (m, 3H); LCMS: m/e 506 (M + H) | 120 mg, 15% |
| 27 | N-((4-fluorophenyl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.19-8.05 (m, 4H), 8.02 (s, 1H), 7.94 (d, 2H), 7.55-7.51 (m, 3H), 6.65 (t, 1H), 3.40 (s, 3H); LCMS: m/e 479 (M + H) | 103 mg, 14% |

Example 7: Preparation of N-(methyl(oxo)(5-(trifluoromethyl)pyridin-2-yl)-$\lambda^6$-sulfanylidene)-1-(4-(5-(trifluoromethyl)-1,2,4-oxadiazol-3-yl)phenyl)-1H-pyrrole-3-carboxamide (compound no. 26)

To a stirred solution of 1-(4-(5-(trifluoromethyl)-1,2,4-oxadiazol-3-yl)phenyl)-1H-pyrrole-3-carboxylic acid (0.3 g, 0.93 mmol) in dichloromethane (10 mL) at 0° C., N,N-dimethylformamide (3.6 µL, 0.05 mmol) and oxalyl chloride (0.09 mL, 1.0 mmol) were added under nitrogen atmosphere. The reaction mixture was heated to 48° C. for 30 minutes. The reaction mixture was brought to 25° C. This mixture was added drop wise to the previously stirred solution of imino(methyl)(5-(trifluoromethyl)pyridin-2-yl)-$\lambda^6$-sulfanone (0.21 g, 0.9 mmol), N,N-diisopropylethylamine (0.24 mL, 1.3 mmol) and 4-dimethylaminopyridine (0.01 g, 0.09 mmol) in dichloromethane (5 mL) under nitrogen atmosphere and reaction mixture was stirred at 25° C. for 2 h. After completion of the reaction, the reaction mixture was quenched by water (10 mL). The compound was extracted thrice with dichloromethane (60 mL). The combined dichloromethane layer was washed twice ice cold water (40 mL). The dichloromethane layer was dried over anhydrous sodium sulphate and evaporated under reduced pressure. The crude compound was purified by flash column chromatography using 70% ethyl acetate in hexane as an eluent to obtain N-(methyl(oxo)(5-(trifluoromethyl)pyridin-2-yl)-$\lambda^6$-sulfanylidene)-1-(4-(5-(trifluoromethyl)-1,2,4-oxadiazol-3-yl)phenyl)-1H-pyrrole-3-carboxamide (0.1 g, 0.2 mmol, 21% yield) as white solid. $^1$H-NMR (400 MHz, DMSO-d6) δ 9.22 (q, 1H), 8.64 (dd, 1H), 8.48-8.44 (m, 1H), 8.14 (dt, 2H), 8.01-7.99 (m, 1H), 7.95-7.92 (m, 2H), 7.53 (dd, 1H), 6.60 (q, 1H), 3.57 (s, 3H); LCMS: m/e 530 (M+H).

The following compounds in table 7 were prepared by using the analogous procedure as described in example 7.

TABLE 7

| Compd. No. | IUPAC name | Analytical Data | Yield |
|---|---|---|---|
| 28 | N-((3-fluoropyridin-4-yl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.90 (d, 1H), 8.79 (d, 1H), 8.16-8.13 (m, 3H), 8.02-7.93 (m, 5H), 7.55 (dd, 1H), 6.62 (q, 1H), 3.65 (s, 3H); LCMS: m/e 480 (M + H) | 90 mg, 12% |
| 29 | N-((4-methoxypyridin-2-yl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.57 (d, 1H), 8.13 (dt, 2H), 7.97 (dd, 1H), 7.93 (dt, 2H), 7.70 (d, 1H), 7.52 (dd, 1H), 7.30 (q, 1H), 6.60 (q, 1H), 4 (q, 3H), 3.50 (s, 3H); LCMS: m/e 492 (M + H) | 140 mg, 18% |
| 30 | N-(dimethyl(oxo)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.13 (dt, 2H), 7.97-7.91 (m, 3H), 7.52 (dd, 1H), 6.62 (q, 1H), 3.40 (s, 6H); LCMS: m/e 399 (M + H) | 250 mg, 41% |

TABLE 7-continued

| Compd. No. | IUPAC name | Analytical Data | Yield |
|---|---|---|---|
| 31 | N-((4-methoxyphenyl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.15-8.12 (m, 2H), 8 (dd, 1H), 7.95 (td, 4H), 7.54 (dd, 1H), 7.20 (dd, 2H), 6.65 (q, 1H), 3.87 (s, 3H), 3.51 (s, 3H); LCMS: m/e 491 | 105 mg, 14% |
| 39 | N-((3-bromophenyl)(isopropyl)(oxo)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.19-8.13 (m, 2H), 8.05 (t, 1H), 7.98-7.94 (m, 4H), 7.86 (dq, 1H), 7.66-7.62 (m, 1H), 7.54 (dd, 1H), 6.64 (q, 1H), 3.85-3.78 (m, 1H), 1.39 (d, 3H), 1.20-1.15 (m, 3H); LCMS: m/e 568 (M + H) | 400 mg, 45% |
| 40 | N-(methyl(oxo)(thiazol-2-yl)-$\lambda^6$-sulfanylidene)-1-(4-(5-(trifluoromethyl)-1,2,4-oxadiazol-3-yl)phenyl)-1H-pyrrole-3-carboxamide | $^1$H-NMR (400 MHz, DMSO-d6) δ 8.31 (d, 1H), 8.17-8.14 (m, 3H), 8.02 (dd, 1H), 7.95 (dd, 2H), 7.56 (dd, 1H), 6.65 (q, 1H), 3.71 (s, 3H); LCMS: m/e 468 (M + H) | 62 mg, 9% |

Example 8: Preparation of N-(4-fluorophenyl)-1-(4-(5-(trifluoromethyl)-1,2,4-oxadiazol-3-yl)phenyl)-1H-pyrazole-4-sulfonamide (Compound No. 47)

Step-1: 4-(1H-pyrazol-1-yl)benzonitrile

To a stirred solution of 1H-pyrazole (10 g, 147 mmol) in N,N-dimethylformamide (100 mL), sodium hydride (5.90 g, 147 mmol) was added in portions under nitrogen atmosphere at 0 TC. After 30 min. of stirring, 4-fluorobenzonitrile (17.80 g, 147 mmol) was added to the reaction mixture at 0° C. and the resulting reaction mixture was allowed to stir at 25° C. for 16 h. After completion of the reaction, the reaction mixture was poured into ice cold water (500 mL). The solid precipitated out was filtered and dried under reduced pressure to obtain 4-(1H-pyrazol-1-yl)benzonitrile (22 g, 130 mmol, 89% yield) as a white solid.

Step-2: N'-hydroxy-4-(1H-pyrazol-1-yl)benzimidamide

To a stirred solution of 4-(1H-pyrazol-1-yl)benzonitrile (13 g, 77 mmol) in ethanol (130 mL), 50% aqueous solution of hydroxylamine (9.40 mL, 154 mmol) was added at 25° C. and the resulting reaction mixture was stirred at 80° C. for 16 h. After completion of the reaction, the reaction mixture was evaporated to dryness under reduced pressure to obtain N'-hydroxy-4-(1H-pyrazol-1-yl)benzimidamide (15 g, 74.2 mmol, 97% yield) which was used as it is in the next step.

Step-3: 3-(4-(1H-pyrazol-1-yl)phenyl)-5-(trifluoromethyl)-1,2,4-oxadiazole

To a stirred solution of N'-hydroxy-4-(1H-pyrazol-1-yl) benzimidamide (15 g, 74.2 mmol) in tetrahydrofuran (100 mL), trifluoroacetic anhydride (18.90 mL, 134 mmol) was added at 0° C. The resulting reaction mixture was stirred for at 25° C. for 12 h. After completion of the reaction, ethyl acetate (100 mL) was added to the reaction mixture followed by saturated sodium bicarbonate solution (100 mL). The ethyl acetate layer was separated, washed with brine solution (25 mL) and dried over anhydrous sodium sulphate. The ethyl acetate was evaporated under reduced pressure to obtain crude compound which was purified by column chromatography to obtain 3-(4-(1H-pyrazol-1-yl)phenyl)-5-(trifluoromethyl)-1,2,4-oxadiazole (17 g, 60.7 mmol, 82% yield).

Step-4: 1-(4-(5-(trifluoromethyl)-1,2,4-oxadiazol-3-yl)phenyl)-1H-pyrazole-4-sulfonyl chloride To a stirred solution of chlorosulfonic acid (14.30 mL, 214 mmol), 3-(4-(1H-pyrazol-1-yl)phenyl)-5-(trifluoromethyl)-1,2,4-oxadiazole (2 g, 7.1 mmol) was added portion wise at 0° C. for 15 min. The resulting reaction mixture was stirred for 24 h at 100° C. The reaction mixture was allowed to cool at 25° C. and reaction mixture poured drop wise into crushed ice containing ethyl acetate (100 mL). The resulting mixture obtained was extracted thrice in ethyl acetate (60 mL). The ethyl acetate layer was separated, dried over anhydrous sodium sulphate and evaporated under reduced pressure to obtain crude 1-(4-(5-(trifluoromethyl)-1,2,4-oxadiazol-3-yl)phenyl)-1H-pyrazole-4-sulfonyl chloride (2 g, 5.28 mmol, 74% yield).

Step-5: N-(4-fluorophenyl)-1-(4-(5-(trifluoromethyl)-1,2,4-oxadiazol-3-yl)phenyl)-1H-pyrazole-4-sulfonamide (Compound No. 47)

To a stirred solution of 4-fluoroaniline (0.2 g, 1.80 mmol) in dichloromethane (10 mL), triethylamine (0.30 mL, 2.0 mmol) was added followed by the addition of 1-(4-(5-(trifluoromethyl)-1,2,4-oxadiazol-3-yl)phenyl)-1H-pyrazole-4-sulfonyl chloride (0.25 g, 0.7 mmol) at 0° C. The resulting reaction mixture was stirred at 25° C. for 8 h. Aqueous saturated sodium bicarbonate solution (10 mL) was added to the reaction mixture and the crude was extracted in dichloromethane (20 mL). The dichloromethane layer was separated, dried over anhydrous sodium sulfate and evaporated under reduced pressure to obtain crude product which was purified by flash chromatography using 10% ethyl acetate in hexane as an eluent to obtain N-(4-fluorophenyl)-1-(4-(5-(trifluoromethyl)-1,2,4-oxadiazol-3-yl)phenyl)-1H-pyrazole-4-sulfonamide (160 mg, 0.35 mmol, 53.5% yield). $^1$H-NMR (400 MHz, DMSO-d6) δ 10.25 (s, 1H), 9.16 (d, 1H), 8.20-8.16 (m, 2H), 8.13 (dt, 2H), 8.02 (d, 1H), 7.20-7.16 (m, 2H), 7.15-7.10 (i, 2H); LCMS (M−H)=452.2.

The following compounds in table 8 were prepared by using the analogous procedure as described in example 8.

TABLE 8

| Compd no. | IUPAC name | Analytical data | Yield |
|---|---|---|---|
| 48 | N-ethyl-1-(4-(5-(trifluoromethyl)-1,2,4-oxadiazol-3-yl)phenyl)-1H-pyrazole-4-sulfonamide | $^1$H-NMR (400 MHz, DMSO-d6) δ 9.19 (d, 1H), 8.23-8.18 (m, 4H), 8.10 (d, 1H), 7.52 (t, 1H), 2.91 (qd, 2H), 1.05 (t, 3H); LCMS (M − H) = 385.7. | 80 mg, 49% |
| 49 | N-(2,4-difluorophenyl)-N-methyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.31 (s, 1H), 8.28 (dt, 2H), 7.93-7.86 (m, 3H), 7.39 (td, 1H), 6.95-6.83 (m, 2H), 3.28-3.26 (m, 3H); LCMS (M + H) = 486.0. | 85 mg, 44% |
| 50 | N-(2-fluorophenyl)-N-methyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.30-8.26 (m, 3H), 7.89-7.86 (m, 3H), 7.41 (td, 1H), 7.37-7.32 (m, 1H), 7.22-7.17 (m, 1H), 7.13-7.08 (m, 1H), 4.80 (d, 1H), 3.30-3.24 (m, 3H); LCMS (M + H) = 467.9. | 55 mg, 30% |
| 51 | 3-(4-(4-(azetidin-1-ylsulfonyl)-1H-pyrazol-1-yl)phenyl)-5-(trifluoromethyl)-1,2,4-oxadiazole | $^1$H-NMR (400 MHz, DMSO-d6) δ 9.39 (s, 1H), 8.29-8.22 (m, 5H), 3.74 (t, 4H), 2.07-2 (m, 2H); LCMS (M + H) = 400.1 | 50 mg, 36% |
| 52 | N-methyl-N-phenyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.27-8.25 (m, 2H), 8.14 (s, 1H), 7.83 (dd, H), 7.74 (s, 1H), 7.40-7.30 (m, 3H), 7.24-7.20 (m, 2H), 3.26 (s, 3H); LCMS (M + H) = 450.0. | 80 mg, 45% |
| 53 | N-(3-methoxyphenyl)-N-methyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.26 (dt, 2H), 8.17 (s, 1H), 7.84 (dt, 2H), 7.78 (s, 1H), 7.27 (s, 1H), 7.24 (d, 1H), 6.87 (ddd, 1H), 6.84 (t, 1H), 6.74 (dq, 1H), 3.80 (d, 3H), 3.26 (d, 3H); LCMS (M + H) = 480.0. | 100 mg, 53% |
| 54 | N-methyl-N-(p-tolyl)-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.27 (dt, 2H), 8.16 (d, 1H), 7.84 (dt, 2H), 7.75 (d, 1H), 7.16 (d, 2H), 7.11-7.08 (m, 2H), 3.23 (s, 3H), 2.36 (s, 3H); LCMS (M + H) = 464.0. | 55 mg, 30% |
| 55 | N-(3-fluorophenyl)-N-methyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.28-8.25 (m, 2H), 8.18 (d, 1H), 7.84 (dt, 2H), 7.76 (d, 1H), 7.33 (td, 1H), 7.03 (d, 1H), 7.02 (t, 1H), 6.99 (t, 1H), 3.25 (s, 3H); LCMS (M + H) = 467.9. | 100 mg, 55% |
| 56 | N-(3-chlorophenyl)-N-methyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.27 (dt, 2H), 8.17 (s, 1H), 7.85 (dt, 2H), 7.78 (s, 1H), 7.33-7.28 (m, 2H), 7.24-7.23 (m, 1H), 7.17-7.13 (m, 1H), 3.24 (s, 3H); LCMS (M + H) = 483.9. | 100 mg, 43% |
| 57 | 3-(4-(4-((3-fluoropyrrolidin-1-yl)sulfonyl)-1H-pyrazol-1-yl)phenyl)-5-(trifluoromethyl)-1,2,4-oxadiazole | $^1$H-NMR (400 MHz, CHLOROFORM-D) δ 8.42 (s, 1H), 8.28 (dt, 2H), 8.02 (s, 1H), 7.90 (dt, 2H), 5.28-5.24 (m, 1H), 3.65-3.52 (m, 3H), 3.37-3.30 (m, 1H), 2.29-2.19 (m, 1H), 2.15-1.99 (m, 1H); LCMS (M + H) = 433.0. | 85 mg, 41% |
| 58 | N-methyl-N-(pyridin-2-yl)-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.37 (dt, 1H), 8.32-8.21 (m, 3H), 7.84 (dt, 2H), 7.77 (td, 2H), 7.65 (d, 1H), 7.20 (ddd, 1H), 3.34 (s, 3H); LCMS (M + H) = 451.0. | 42 mg, 20% |
| 59 | 4-((1-(4-(5-(trifluoromethyl)-1,2,4-oxadiazol-3-yl)phenyl)-1H-pyrazol-4-yl)sulfonyl)morpholine | $^1$H-NMR (400 MHz, CHLOROFORM-D) δ 8.37 (d, 1H), 8.29 (dt, 2H), 7.97 (d, 1H), 7.91 (dt, 2H), 3.81 (t, 4H), 3.12-3.07 (m, 4H); LCMS (M + H) = 430.0. | 85 mg, 42% |
| 60 | N-cyclopropyl-1-(4-(5-(trifluoromethyl)-1,2,4-oxadiazol-3-yl)phenyl)-1H-pyrazole-4-sulfonamide | $^1$H-NMR (400 MHz, CHLOROFORM-D) δ 8.47 (d, 0.5, 1H), 8.28 (dt, 2H), 8.05 (s, 1H), 7.90 (dt, 2H), 4.94 (s, 1H), 2.44-2.39 (m, 1H), 0.76-0.67 (m, 4H); LCMS (M − H) = 397.9. | 55 mg, 29% |
| 42 | 3-(4-(4-(piperidin-1-ylsulfonyl)-1H-pyrazol-1-yl)phenyl)-5-(trifluoromethyl)-1,2,4-oxadiazole | $^1$H-NMR (400 MHz, DMSO-d6) δ 9.27 (d, 1H), 8.22 (s, 4H), 8.16 (d, 1H), 2.93 (t, 4H), 1.62-1.56 (m, 4H), 1.42-1.39 (m, 2H); LCMS (M + H) = 428.0 | 150 mg, 53% |
| 62 | N-benzyl-1-(4-(5-(trifluoromethyl)-1,2,4-oxadiazol-3-yl)phenyl)-1H-pyrazole-4-sulfonamide | $^1$H-NMR (400 MHz, DMSO-d6) δ 9.12 (s, 1H), 8.23-8.20 (m, 2H), 8.17-8.13 (m, 3H), 8.07 (s, 1H), 7.31-7.26 (m, 4H), 7.20 (dt, 1H), 4.12 (d, 2H); LCMS (M − H) = 447.8. | 100 mg, 58% |

Example 9: Preparation of 3-(4-(4-((phenylthio)methyl)-1H-imidazol-1-yl)phenyl)-5-(trifluoromethyl)-1,2,4-oxadiazole (Compound No. 43)

Step 1: 4-(4-formyl-1H-imidazol-1-yl)benzonitrile

To a stirred solution of 1H-imidazole-4-carbaldehyde (9.52 g, 99 mmol) and N,N-dimethylformamide (120 mL), 4-fluorobenzonitrile (12 g, 99 mmol) was added followed by the addition of potassium carbonate (2.282 g, 16.5 mmol) at 25° C. and the resulted mixture was heated at 100° C. for 16 h. The reaction mixture was quenched with water (50 mL), obtained solid was filtered, further washed twice with water (20 mL) and ethyl acetate (25 mL). Then solid obtained was dried under reduced pressure to obtain 4-(4-formyl-1H-imidazol-1-yl)benzonitrile (18 g, 91 mmol, 92% yield).

Step 2: 4-(4-(hydroxymethyl)-1H-imidazol-1-yl)benzonitrile

To a stirred solution of 4-(4-formyl-1H-imidazol-1-yl)benzonitrile (15 g, 76 mmol) in a mixture of tetrahydrofuran (75 mL) and methanol (75 mL), sodium borohydride (5.76 g, 152 mmol) was added portion wise at 0° C., then resulted mixture was stirred at 25° C. for 16 h. After completion of the reaction, the reaction mixture was concentrated and extracted twice with dichloromethane (20 mL). The dichloromethane layer was washed twice with water (25 mL). The water layer was again extracted with 10% methanol in dichloromethane. The combined organic layer was washed twice with brine solution (100 mL), dried over anhydrous sodium sulfate and evaporated under reduced pressure to obtain 4-(4-(hydroxymethyl)-1H-imidazol-1-yl)benzonitrile (13 g, 65.3 mmol, 86% yield).

Step 3: 4-(4-(chloromethyl)-1H-imidazol-1-yl)benzonitrile

To a stirred solution of 4-(4-(hydroxymethyl)-1H-imidazol-1-yl)benzonitrile (1 g, 5.0 mmol) and chloroform (70 mL), thionyl chloride (0.440 mL, 6.0 mmol) was added drop wise at 0° C. and the resulting reaction mixture was refluxed for 2-3 h at 68° C. The reaction mixture was brought to 25° C. and diluted with water (100 mL). The product was extracted thrice with dichloromethane (10 mL). The combined dichloromethane layer was washed thrice with water (15 mL) and dried over anhydrous sodium sulphate. The dichloromethane layer was evaporated under reduced pressure to obtain 4-(4-(chloromethyl)-1H-imidazol-1-yl)benzonitrile (1 g, 4.64 mmol, 92% yield).

Step 4: 4-(4-((phenylthio)methyl)-1H-imidazol-1-yl)benzonitrile

To a stirred solution of 4-(4-(chloromethyl)-1H-imidazol-1-yl)benzonitrile (1 g, 4.6 mmol) and N,N-dimethylformamide (10 mL), thiophenol (0.568 mL, 5.5 mmol) and potassium carbonate (1.587 g, 11.5 mmol) were added at 0° C. The resulting reaction mixture was stirred at 25° C. for 16 h. After completion of the reaction, the reaction mixture was extracted twice with ethyl acetate (20 mL) and washed four times with water (25 mL). The combined ethyl acetate layer was dried over anhydrous sodium sulphate and concentrated under reduced pressure. The crude product was purified by column chromatography on silica gel using 80% ethyl acetate in hexane as eluent to obtain 4-(4-((phenylthio)methyl)-1H-imidazol-1-yl)benzonitrile (1.12 g, 3.8 mmol, 84% yield).

Step 5: N'-hydroxy-4-(4-((phenylthio)methyl)-1H-imidazol-1-yl)benzimidamide

To a stirred solution of 4-(4-((phenylthio)methyl)-1H-imidazol-1-yl)benzonitrile (1.14 g, 3.9 mmol) and ethanol (10 mL), 50% aqueous solution of hydroxylamine (0.435 mL, 7.0 mmol) was added at 0° C. and stirred for 8 h. After completion of the reaction, the reaction mixture was concentrated. The residue was added again ethyl acetate, stirred and then concentrated to obtain N'-hydroxy-4-(4-((phenylthio)methyl)-1H-imidazol-1-yl)benzimidamide (1.2 g, 3.70 mmol, 95% yield).

Step 6: 3-(4-(4-((phenylthio)methyl)-1H-imidazol-1-yl)phenyl)-5-(trifluoromethyl)-1,2,4-oxadiazole (compound no. 43)

To a stirred solution of N'-hydroxy-4-(4-((phenylthio)methyl)-1H-imidazol-1-yl)benzimidamide (1.49 g, 4.5 mmol) in tetrahydrofuran (7 mL), trifluoroacetic anhydride (0.973 mL, 6.8 mmol) was added at 0° C. and stirred for 16 h. After completion of the reaction, the reaction mixture was diluted with ethyl acetate (20 mL) and washed with aqueous sodium bicarbonate solution (20 mL). The ethyl acetate layer was dried over anhydrous sodium sulphate and concentrated to obtain crude compound. The crude residue was purified by column chromatography on silica gel using eluent 70% ethyl acetate in hexane to obtain 3-(4-(4-((phenylthio)methyl)-1H-imidazol-1-yl)phenyl)-5-(trifluoromethyl)-1,2,4-oxadiazole (1.43 g, 3.55 mmol, 77% yield). $^1$H-NMR (400 MHz, DMSO-d6) δ 8.38 (d, 1.2, 1H), 8.16 (dd, 6.9, 2.0, 2H), 7.87-7.90 (m, 2H), 7.77 (t, 0.6, 1H), 7.38-7.40 (m, 2H), 7.28-7.32 (m, 2H), 7.15-7.19 (m, 1H), 4.18 (s, 2H)—LCMS (M+H)=403.35.

The following compounds in table 9 were prepared by using the analogous procedure as described in example 9.

TABLE 9

| Compd no. | IUPAC name | Analytical Data | Yield |
|---|---|---|---|
| 64 | 3-(4-(4-(((4-methoxyphenyl)thio)methyl)-1H-imidazol-1-yl)phenyl)-5-(trifluoromethyl)-1,2,4-oxadiazole | $^1$H-NMR (400 MHz, DMSO-d6) δ 7.55 (d, 1H), 7.34 (dt, 2H), 7.05 (dt, 2H), 6.85 (d, 1H), 6.51-6.55 (m, 2H), 6.05-6.09 (m, 2H), 3.23 (s, 2H), 2.90 (s, 3H); LCMS (M + H) = 433 | 231 mg, 47% |

TABLE 9-continued

| Compd no. | IUPAC name | Analytical Data | Yield |
|---|---|---|---|
| 65 | 3-(4-(4-((isopropylthio)methyl)-1H-imidazol-1-yl)phenyl)-5-(trifluoromethyl)-1,2,4-oxadiazole | $^1$H-NMR (400 MHz, DMSO-d6) δ 7.54 (d, 1H), 7.35 (dt, 2H), 7.10 (dt, 2H), 6.94 (t, 1H), 2.85 (d, 2H), 2.15 (td, 1H), 0.41 (d, 6H); LCMS (M + H) = 369 | 640 mg, 69% |
| 66 | 3-(4-(4-(((2-fluorophenyl)thio)methyl)-1H-imidazol-1-yl)phenyl)-5-(trifluoromethyl)-1,2,4-oxadiazole | $^1$H-NMR (400 MHz, DMSO-d6) δ 8.38 (d, 1H), 8.16 (dt, 2H), 7.87-7.90 (m, 2H), 7.78 (d, 1H), 7.56 (td, 1H), 7.15-7.28 (m, 3H), 4.18 (s, 2H); LCMS (M + H) = 421.35 | 1.36 g 79% |
| 67 | 3-(4-(4-(((4-fluorophenyl)thio)methyl)-1H-imidazol-1-yl)phenyl)-5-(trifluoromethyl)-1,2,4-oxadiazole | $^1$H-NMR (400 MHz, DMSO-d6) δ 8.38 (d, 1H), 8.16 (dt, 2H), 7.88 (dt, 2H), 7.73 (t, 1H), 7.42-7.47 (m, 2H), 7.12-7.19 (m, 2H), 4.14 (s, 2H); LCMS (M + H) = 421.30 | 1.41 g, 73% |
| 68 | 3-(4-(4-(((3-chlorophenyl)thio)methyl)-1H-imidazol-1-yl)phenyl)-5-(trifluoromethyl)-1,2,4-oxadiazole | $^1$H-NMR (400 MHz, DMSO-d6) δ 7.58 (d, 1H), 7.34 (dt, 2H), 7.07 (dt, 2H), 6.98 (t, 1H), 6.65 (t, 1H), 6.48-6.55 (m, 2H), 6.38-6.41 (m, 1H), 3.41 (s, 2H); LCMS (M + H) = 437.30 | 1.45 g, 81% |
| 69 | 3-(4-(4-(((4-methoxybenzyl)thio)methyl)-1H-imidazol-1-yl)phenyl)-5-(trifluoromethyl)-1,2,4-oxadiazole | $^1$H-NMR (400 MHz, DMSO-d6) δ 8.38 (d, 1H), 8.17 (dt, 2H), 7.92 (dt, 2H), 7.72 (d, 1H), 7.27 (dt, 2H), 6.86-6.89 (m, 2H), 3.74 (s, 2H), 3.72 (s, 3H), 3.55 (d, 2H)LCMS (M + H) = 447.40 | 1.22 g, 64% |
| 70 | 3-(4-(4-((pyridin-2-ylthio)methyl)-1H-imidazol-1-yl)phenyl)-5-(trifluoromethyl)-1,2,4-oxadiazole | $^1$H-NMR (400 MHz, DMSO-d6) δ 8.46 (dq, 1H), 8.38 (d, 1H), 8.15 (dt, 2H), 7.89 (dt, 2H), 7.80 (t, 1H), 7.63-7.67 (m, 1H), 7.35 (dt, 1H), 7.12 (ddd, 1H), 4.36 (s, 2H); LCMS (M + H) – 404.40 | 990 mg, 64% |

Example 10: Preparation of 3-(4-(4-((phenylsulfonyl)methyl)-1H-imidazol-1-yl)phenyl)-5-(trifluoromethyl)-1,2,4-oxadiazole (Compound No. 71)

To a stirred solution of 3-(4-(4-((phenylthio)methyl)-1H-imidazol-1-yl)phenyl)-5-(trifluoromethyl)-1,2,4-oxadiazole (200 mg, 0.5 mmol) in methanol (5 m), oxone (1.2 g, 1.9 mmol) was added at 0° C. and stirred for 8 h. After completion of the reaction, the reaction was mixture was concentrated then quenched with water (20 mL) and extracted thrice with ethyl acetate (10 mL). The combined ethyl acetate layer was washed twice with brine solution (10 mL), dried over anhydrous sodium sulphate and evaporated under reduced pressure to obtain crude. The crude compound was purified by prep HPLC to obtain 3-(4-(4-((phenylsulfonyl)methyl)-1H-imidazol-1-yl)phenyl)-5-(trifluoromethyl)-1,2,4-oxadiazole (138 mg, 0.318 mmol, 64% yield). $^1$H-NMR (400 MHz, DMSO-d6) δ 8.34 (d, 1.2, 1H), 8.17 (dt, 9.2, 2H), 7.87 (dt, 2H), 7.78-7.81 (m, 2H), 7.75 (d, 1.2, 1H), 7.69-7.74 (m, 1H), 7.58-7.62 (m, 2H), 4.61 (s, 2H)—LCMS (M+H)=434.95.

The following compounds in table 10 were prepared by using the analogous procedure as described in example 10.

TABLE 10

| Compd no. | IUPAC name | Analytical Data | Yield |
|---|---|---|---|
| 72 | 3-(4-(4-(((4-methoxyphenyl)sulfonyl)methyl)-1H-imidazol-1-yl)phenyl)-5-(trifluoromethyl)-1,2,4-oxadiazole | $^1$H-NMR (400 MHz, DMSO-d6) δ 8.35 (d, 1H), 8.18 (dd, 2H), 7.89 (dd, 2H), 7.76 (d, 1H), 7.69 (dd, 2H), 7.10 (dd, 2H), 4.54 (s, 2H), 3.84 (s, 3H); LCMS (M + H) – 465.35 | 91 mg, 72% |
| 73 | 3-(4-(4-((isopropylsulfonyl)methyl)-1H-imidazol-1-yl)phenyl)-5-(trifluoromethyl)-1,2,4-oxadiazole | $^1$H-NMR (400 MHz, DMSO-d6) δ 8.47 (d, 1H), 8.19 (dt, 2H), 7.93-7.96 (m, 3H), 4.40 (s, 2H), 3.33-3.40 (m, 1H), 1.29 (d, 6H) ); LCMS (M + H) – 401 | 192 mg, 74% |
| 74 | 3-(4-(4-(((2-fluorophenyl)sulfonyl)methyl)-1H-imidazol-1-yl)phenyl)-5-(trifluoromethyl)-1,2,4-oxadiazole | $^1$H-NMR (400 MHz, DMSO-d6) δ 8.31 (d, 1H), 8.16 (dt, 2H), 7.86-7.88 (m, 3H), 7.76-7.81 (m, 1H), 7.68 (td, 1H), 7.51 (ddd, 1H), 7.37 (td, 1H), 4.71 (s, 2H); LCMS (M + H) – 453 | 152 mg, 71% |
| 75 | 3-(4-(4-(((4-fluorophenyl)sulfonyl)methyl)-1H-imidazol-1-yl)phenyl)-5-(trifluoromethyl)-1,2,4-oxadiazole | $^1$H-NMR (400 MHz, DMSO-d6) δ 8.35 (d, 1H), 8.18 (dd, 2H), 7.83-7.90 (m, 4H), 7.79 (d, 1H), 7.42-7.46 (m, 2H), 4.64 (s, 2H); LCMS (M + H) – 453.10 | 109 mg, 51% |

TABLE 10-continued

| Compd no. | IUPAC name | Analytical Data | Yield |
|---|---|---|---|
| 76 | 3-(4-(4-(((3-chlorophenyl)sulfonyl)methyl)-1H-imidazol-1-yl)phenyl)-5-(trifluoromethyl)-1,2,4-oxadiazole | $^1$H-NMR (400 MHz, DMSO-d6) δ 8.36 (d, 1H), 8.18 (dt, 2H), 7.88 (dt, 2H), 7.79-7.83 (m, 3H), 7.73-7.75 (m, 1H), 7.61-7.65 (m, 1H), 4.72 (s, 2H); LCMS (M + H) − 468.95 | 156 mg, 73% |
| 77 | 3-(4-(4-(((4-methoxybenzyl)sulfonyl)methyl)-1H-imidazol-1-yl)phenyl)-5-(trifluoromethyl)-1,2,4-oxadiazole | $^1$H-NMR (400 MHz, DMSO-d6) δ 8.52 (d, 1H), 8.20 (dd, 2H), 7.94-7.97 (m, 3H), 7.41 (dd, 2H), 6.96 (dd, 2H), 4.48 (s, 2H), 4.32 (s, 2H), 3.76 (s, 3H)); LCMS (M + H) − 479.15 | 122 mg, 46% |
| 78 | 3-(4-(4-((pyridin-2-ylsulfonyl)methyl)-1H-imidazol-1-yl)phenyl)-5-(trifluoromethyl)-1,2,4-oxadiazole | $^1$H-NMR (400 MHz, DMSO-d6) δ 8.85 (d, 1H), 8.32 (d, 1H), 8.16 (d, 2H), 8.09 (td, 1H), 7.92 (d, 1H), 7.87 (d, 2H), 7.80 (s, 1H), 7.75 (ddd, 1H), 4.76 (s, 2H) ); LCMS (M + H) − 435.95 | 69 mg, 26% |

Example 11-Preparation of imino(phenyl)((1-(4-(5-(trifluoromethyl)-1,2,4-oxadiazol-3-yl)phenyl)-1H-imidazol-4-yl)methyl)-λ$^6$-sulfanone (Compound No. 79)

To a stirred solution of 3-(4-(4-((phenylthio)methyl)-1H-imidazol-1-yl)phenyl)-5-(trifluoromethyl)-1,2,4-oxadiazole (200 mg, 0.4 mmol) in methanol (5 mL), iodobenzene diacetate (480 mg, 1.5 mmol) and ammonium carbamate (38.8 mg, 0.5 mmol) were added at 0° C. and stirred for 16 h. After completion of the reaction, the reaction mixture was concentrated to obtain crude compound. The crude compound was purified by prep HPLC chromatography to obtain imino(phenyl)((1-(4-(5-(trifluoromethyl)-1,2,4-oxadiazol-3-yl)phenyl)-1H-imidazol-4-yl)methyl)-λ$^6$-sulfanone (50 mg, 0.115 mmol, 23% yield). $^1$H-NMR (400 MHz, DMSO-d6) δ 8.32 (d, 2H), 8.18 (dt, 2H), 7.87 (dt, 2H), 7.79-7.82 (m, 2H), 7.72 (d, 1H), 7.61-7.66 (m, 1H), 7.52-7.56 (i, 2H), 4.43 (dd, 18.8, 14.2, 2H), 4.29 (s, 1H); 433.95.

The following compounds in table 10 were prepared by using the analogous procedure as described in example 10.

TABLE 11

| Compd no. | IUPAC name | Analytical Data | Yield |
|---|---|---|---|
| 80 | (2-fluorophenyl)(imino)((1-(4-(5-(trifluoromethyl)-1,2,4-oxadiazol-3-yl)phenyl)-1H-imidazol-4-yl)methyl)-λ$^6$-sulfanone | $^1$H-NMR (400 MHz, DMSO-d6) δ 8.27 (d, 1H), 8.16 (dt, 2H), 7.79-7.93 (m, 3H), 7.64-7.72 (m, 2H), 7.39-7.44 (m, 1H), 7.30 (td, 1H), 4.73 (s, 1H), 4.57 (dd, 2H); LCMS (M + H) − 435.95 | 122 mg, 38% |
| 121 | (4-fluorophenyl)(imino)((1-(4-(5-(trifluoromethyl)-1,2,4-oxadiazol-3-yl)phenyl)-1H-imidazol-4-yl)methyl)-λ$^6$-sulfanone | $^1$H-NMR (400 MHz, DMSO-d6) δ 8.41-8.24 (1H), 8.28-8.09 (2H), 7.92-7.86 (2H), 7.86-7.78 (2H), 7.78-7.68 (1H), 7.48-7.28 (2H), 4.51-4.42 (2H), 4.41-4.35 (1H) | 120 mg, 37% |
| 122 | (3-chlorophenyl)(imino)((1-(4-(5-(trifluoromethyl)-1,2,4-oxadiazol-3-yl)phenyl)-1H-imidazol-4-yl)methyl)-λ$^6$-sulfanone | $^1$H-NMR (400 MHz, DMSO-d6) δ 8.33 (d,, 1H), 8.18 (dt, 2H), 7.88 (dt, 2H), 7.76 (t, 2H), 7.70-7.74 (m, 2H), 7.58 (t, 1H), 4.45-4.54 (m, 3H); LCMS(M + H) − 467.90 | 147 mg, 46% |

Example 12: Preparation of 4-methyl-N-((1-(4-(5-(trifluoromethyl)-1,2,4-oxadiazol-3-yl)phenyl)-1H-imidazol-4-yl)methyl)benzenesulfonamide (compound no. 81)

Step-1: tert-butyl (tert-butoxycarbonyl)((1-(4-cyanophenyl)-1H-imidazol-4-yl)methyl)carbamate To a stirred solution of di-tert-butyl iminodicarboxylate (5 g, 23 mmol) in N,N-dimethylformamide (50 mL), potassium carbonate (6.4 g, 46 mmol) was added at 25° C. and stirred for 15 min at the same temperature. 4-(4-(chloromethyl)-1H-imidazol-1-yl)benzonitrile (5.0 g, 23 mmol) was added and the resulting reaction mixture was heated to 90° C. for 16 h. After completion of the reaction, the reaction mixture was quenched with ice-water (200 mL) and extracted thrice with ethyl acetate (100 mL). The combined ethyl acetate layer was dried over anhydrous sodium sulfate and evaporated to dryness under reduced pressure. The obtained crude was purified by flash chromatography using 2% methanol in dichloromethane as eluent to obtain tert-butyl (tert-butoxycarbonyl)((1-(4-cyanophenyl)-1H-imidazol-4-yl)methyl) carbamate (6.0 g, 66% yield) as a white solid.

Step-2: tert-butyl (tert-butoxycarbonyl)((1-(4-(N'-hydroxycarbamimidoyl)phenyl)-1H-imidazol-4-yl) methyl)carbamate To a stirred solution of tert-butyl (tert-butoxycarbonyl) ((1-(4-cyanophenyl)-1H-imidazol-4-yl)methyl)carbamate (2 g, 5 mmol) in methanol (20 mL), 50% aqueous solution of hydroxylamine (1.3 mL, 20 mmol) was added at 0° C. The resulting reaction mixture was stirred at 25° C. for 16 h. After completion of the reaction, the volatiles were evaporated under reduced pressure. The obtained crude compound was triturated with 10% ethyl acetate in hexane to obtain tert-butyl (tert-butoxycarbonyl)((1-(4-(N'-hydroxycarbamimidoyl)phenyl)-1H-imidazol-4-yl)methyl)carbamate (2.1 g, 4.9 mmol, 97% yield) as a white solid.

Step-3: tert-butyl (tert-butoxycarbonyl)((1-(4-(5-(trifluoromethyl)-1,2,4-oxadiazol-3-yl)phenyl)-1H-imidazol-4-yl)methyl)carbamate To a stirred solution of tert-butyl (tert-butoxycarbonyl)((1-(4-(N'-hydroxycarbamimidoyl)phenyl)-1H-imidazol-4-yl)methyl)carbamate (2.1 g, 4.8 mmol) in tetrahydrofuran (20 mL), trifluoroacetic anhydride (1.7 mL, 12 mmol) was added at 0° C. and the resulting reaction mixture was stirred at 25° C. for 16 h. After completion of the reaction, the volatiles were evaporated under reduced pressure. The obtained crude compound was triturated with 10% ethyl acetate in hexane to get tert-butyl (tert-butoxycarbonyl)((1-(4-(5-(trifluoromethyl)-1,2,4-oxadiazol-3-yl)phenyl)-1H-imidazol-4-yl)methyl)carbamate (2.4 g, 97% yield) as a sticky solid.

$^1$H-NMR (400 MHz, DMSO-d6) δ 8.35 (d, 1H), 8.16 (dd, 2H), 7.90 (dd, 2H), 7.61 (d, 1H), 4.64 (s, 2H), 1.42 (s, 18H); LCMS (M+H): 510.10.

Step-4: (1-(4-(5-(trifluoromethyl)-1,2,4-oxadiazol-3-yl)phenyl)-1H-imidazol-4-yl)methanamine hydrochloride To a stirred solution of tert-butyl (tert-butoxycarbonyl)((1-(4-(5-(trifluoromethyl)-1,2,4-oxadiazol-3-yl)phenyl)-1H-imidazol-4-yl)methyl)carbamate (2.5 g, 4.9 mmol) in tetrahydrofuran (25 mL), 4M hydrogen chloride in dioxane (6.1 mL, 25 mmol) was added at 0° C. The resulting reaction mixture was warmed to 25° C. and further heated to 70° C. for 4 h. After completion of the reaction, the volatiles were evaporated under reduced pressure. The obtained crude compound was co-distilled thrice with toluene (20 mL) to get (1-(4-(5-(trifluoromethyl)-1,2,4-oxadiazol-3-yl)phenyl)-1H-imidazol-4-yl)methanamine hydrochloride (1.5 g, 4.3 mmol, 88% yield). $^1$H-NMR (400 MHz, DMSO-d6) δ 9.01 (s, 1H), 8.59 (s, 3H), 8.25 (dt, 2.1, 2H), 8.16 (s, 1H), 7.96 (dt, 2H), 4.06 (q, 2H); LCMS (M+H): 310.10.

Step-5: 4-methyl-N-((1-(4-(5-(trifluoromethyl)-1,2,4-oxadiazol-3-yl)phenyl)-1H-imidazol-4-yl)methyl)benzenesulfonamide (Compound No. 81)

To a stirred solution of (1-(4-(5-(trifluoromethyl)-1,2,4-oxadiazol-3-yl)phenyl)-1H-imidazol-4-yl)methanamine hydrochloride (0.16 g, 0.5 mmol) in dichloromethane (5 mL) was added 4-methylbenzenesulfonyl chloride (0.088 g, 0.56 mmol) followed by triethylamine (0.13 mL, 0.9 mmol) at 0° C. Then resulted mixture was stirred at 0° C. for 30 min. After completion of the reaction, the reaction mixture was quenched with water (50 mL) and extracted twice with dichloromethane (50 mL). The combined dichloromethane layer was dried over sodium sulfate and evaporated under reduced pressure. The obtained crude was purified by prep-HPLC to obtain 4-methyl-N-((1-(4-(5-(trifluoromethyl)-1,2,4-oxadiazol-3-yl)phenyl)-1H-imidazol-4-yl)methyl)benzenesulfonamide (0.16 g, 72% yield) as a white solid. $^1$H-NMR (400 MHz, DMSO-d6) δ 8.29 (d, 1H), 8.15-8.17 (m, 2H), 7.94 (t, 1H), 7.79-7.82 (m, 2H), 7.67 (d, 2H), 7.48 (s, 1H), 7.33 (d, 2H), 3.92 (d, 2H), 2.30 (s, 3H) LCMS (M+H): 464.40.

The following compounds in table 12 were prepared by using the analogous procedure as described in example 12.

TABLE 12

| Compd no. | IUPAC name | Analytical data | Yield |
|---|---|---|---|
| 82 | N-((1-(4-(5-(trifluoromethyl)-1,2,4-oxadiazol-3-yl)phenyl)-1H-imidazol-4-yl)methyl)benzenesulfonamide | $^1$H-NMR (400 MHz, DMSO-d6) δ 8.29 (d, 1H), 8.16 (dt, 2H), 8.04 (t, 1H), 7.79-7.83 (m, 4H), 7.52-7.60 (m, 4H), 3.94 (d, 6.1, 2H),; LCMS(M + H): 450.10 | 200 mg, 44% |
| 86 | 4-fluoro-N-((1-(4-(5-(trifluoromethyl)-1,2,4-oxadiazol-3-yl)phenyl)-1H-imidazol-4-yl)methyl)benzenesulfonamide | $^1$H-NMR (400 MHz, DMSO-d6) δ 8.29 (d, 1H), 8.15-8.17 (m, 2H), 8.09 (t, 1H), 7.81-7.85 (m, 4H), 7.57 (d, 1H), 7.33-7.38 (m, 2H), 3.96 (d, 2H),; LCMS(M + H): 468 | 160 mg, 74% |
| 87 | N-((1-(4-(5-(trifluoromethyl)-1,2,4-oxadiazol-3-yl)phenyl)-1H-imidazol-4-yl)methyl)cyclopropanesulfonamide | $^1$H-NMR (400 MHz, DMSO-d6) δ 8.41 (d, 1H), 8.16-8.19 (m, 2H), 7.92 (dd, 2H), 7.78 (s, 1H), 7.47 (t, 1H), 4.14 (d, 2H), 2.55-2.61 (m, 1H), 0.86-0.94 (m, 4H),; LCMS(M + H): 413.95 | 110 mg, 96% |

Example 13: Preparation of N-((1-(4-(5-(trifluoromethyl)-1,2,4-oxadiazol-3-yl)phenyl)-1H-imidazol-4-yl)methyl)acetamide (Compound No. 85)

To a stirred solution of (1-(4-(5-(trifluoromethyl)-1,2,4-oxadiazol-3-yl)phenyl)-1H-imidazol-4-yl)methanamine hydrochloride (0.16 g, 0.45 mmol) in dichloromethane (5 mL), acetyl chloride (0.033 mL, 0.56 mmol) was added followed by triethylamine (0.13 mL, 0.93 mmol) at 0° C. The resulting reaction mixture was stirred at 0° C. for 30 min. After completion of the reaction, reaction was quenched with water (50 mL) and extracted twice with dichloromethane (50 mL), combined dichloromethane layer was dried over anhydrous sodium sulfate and evaporated under reduced pressure. The obtained crude was purified by prep HPLC to obtain N-((1-(4-(5-(trifluoromethyl)-1,2,4-oxadiazol-3-yl)phenyl)-1H-imidazol-4-yl)methyl)acetamide (0.05 g, 31% yield) as a white solid. $^1$H-NMR (400 MHz, DMSO-d6) δ 8.38 (d, 1H), 8.15-8.21 (m, 3H), 7.91 (dd, 2H), 7.69 (s, 1H), 4.18 (d, 2H), 1.85 (s, 3H) LCMS (M−H): 351.95.

The following compounds in table 13 were prepared by using the analogous procedure as described in example 13.

TABLE 13

| Compd no. | IUPAC name | Analytical data | yield |
|---|---|---|---|
| 88 | 4-(trifluoromethyl)-N-((1-(4-(5-(trifluoromethyl)-1,2,4-oxadiazol-3-yl)phenyl)-1H-imidazol-4-yl)methyl)benzamide | $^1$H-NMR (400 MHz, DMSO-d6) δ 9.16 (t, 5.7, 1H), 8.41 (d, 1H), 8.14-8.17 (m, 2H), 8.10 (d, 2H), 7.93 (d, 2H), 7.85 (d, 2H), 7.77 (s, 1H), 4.45 (d, 2H), LCMS (M + H): 482 | 150 mg, 60% |
| 89 | N-((1-(4-(5-(trifluoromethyl)-1,2,4-oxadiazol-3-yl)phenyl)-1H-imidazol-4-yl)methyl)isobutyramide | $^1$H-NMR (400 MHz, DMSO-d6) δ 8.38 (d, 1H), 8.17 (dt, 2H), 8.09 (t, 1H), 7.90 (dt, 2H), 7.64 (d, 1H), 4.19 (d, 2H), 2.39-2.46 (m, 1H), 1.01 (d, 6H),; LCMS (M + H): 380 | 150 mg, 68% |
| 90 | N-((1-(4-(5-(trifluoromethyl)-1,2,4-oxadiazol-3-yl)phenyl)-1H-imidazol-4-yl)methyl)cyclobutanecarboxamide | $^1$H-NMR (400 MHz, DMSO-d6) δ 8.38 (d, 1H), 8.15-8.18 (m, 2H), 8 (t, 1H), 7.90 (dd, 2H), 7.65 (s, 1H), 4.19 (d, 2H), 3.01-3.09 (m, 1H), 2.09-2.19 (m, 2H), 1.96-2.04 (m, 2H), 1.83-1.92 (m, 1H), 1.71-1.79 (m, 1H),; LCMS (M + H): 392.35 | 170 mg, 75% |
| 91 | N-((1-(4-(5-(trifluoromethyl)-1,2,4-oxadiazol-3-yl)phenyl)-1H-imidazol-4-yl)methyl)benzamide | $^1$H-NMR (400 MHz, DMSO-d6) δ 8.89 (t, 1H), 8.39 (d, 1H), 8.14-8.16 (m, 2H), 7.89-7.94 (m, 4H), 7.72 (d, 1H), 7.50-7.54 (m, 1H), 7.43-7.47 (m, 2H), 4.43 (d, 2H):,; LCMS(M + H): 414.05 | 210 mg, 44% |
| 92 | 4-methoxy-N-((1-(4-(5-(trifluoromethyl)-1,2,4-oxadiazol-3-yl)phenyl)-1H-imidazol-4-yl)methyl)benzamide | $^1$H-NMR (400 MHz, DMSO-d6) δ 8.95 (s, 1H), 8.77 (d, 1H), 8.23 (dd, 2H), 7.95-7.99 (m, 3H), 7.71 (td, 1H), 7.52-7.57 (m, 1H), 7.27-7.32 (m, 2H), 4.50 (d, 2H),; LCMS(M + H): 444.05 | 175 mg, 68% |
| 93 | 2-fluoro-N-((1-(4-(5-(trifluoromethyl)-1,2,4-oxadiazol-3-yl)phenyl)-1H-imidazol-4-yl)methyl)benzamide | $^1$H-NMR (400 MHz, DMSO-d6) δ 8.95 (s, 1H), 8.78 (s, 1H), 8.23 (dd, 2H), 7.95-7.99 (m, 3H), 7.71 (td, 1H), 7.52-7.57 (m, 1H), 7.27-7.32 (m, 2H), 4.50 (d, 5.6, 2H),; LCMS (M + H): 432 | 130 mg, 52% |
| 94 | N-((1-(4-(5-(trifluoromethyl)-1,2,4-oxadiazol-3-yl)phenyl)-1H-imidazol-4-yl)methyl)methanesulfonamide | $^1$H-NMR (400 MHz, DMSO-d6) δ 8.43 (d, 1H), 8.18 (dd, 2H), 7.92 (dd, 2H), 7.79 (d, 1H), 7.41 (t, 1H), 4.12 (d, 2H), 2.92 (s, 3H),; LCMS (M + H): 430.80 | 128 mg, 57% |
| 95 | N-((1-(4-(5-(trifluoromethyl)-1,2,4-oxadiazol-3-yl)phenyl)-1H-imidazol-4-yl)methyl)thiazole-2-carboxamide | $^1$H-NMR (400 MHz, DMSO-d6) δ 9.08 (t, 1H), 8.41 (s, 1H), 8.15 (dd, 2H), 8.03 (dd, 2H), 7.92 (dd, 2H), 4.44 (d, 2H); LCMS (M + H): 420.90 | 50 mg, 21% |

Example 14: Preparation of 2-(3,5-dimethyl-1-(4-(5-(trifluoromethyl)-1,2,4-oxadiazol-3-yl)phenyl)-1H-pyrazol-4-yl)-N-phenylacetamide (Compound No. 96)

Step-1: tert-Butyl-3-acetyl-4-oxopentanoate

A suspension of sodium hydride (0.320 g, 8 mmol) and anhydrous tetrahydrofuran (20 ML) was cooled to 0° C. A solution of pentane-2,4-dione (0.688 mL, 6.77 mmol) and anhydrous tetrahydrofuran (10 mL) was added to this suspension and mixture was stirred for 1 h. A solution of ethyl-2-bromoacetate (0.811 mL, 7.3 mmol) and anhydrous tetrahydrofuran (10 mL) was added to and the resulting reaction mixture was stirred for 18 h. The reaction mixture was quenched by adding an aqueous saturated aqueous ammonium chloride solution. The product was extracted with ethyl acetate (20 mL). The combined ethyl acetate layer was washed with brine solution (20 mL), dried over anhydrous magnesium sulfate and concentrated under reduced pressure to obtain tert-Butyl-3-acetyl-4-oxopentanoate (0.869 g, 98% yield) as a yellow oil.

Step-2: tert-Butyl-2-(3,5-dimethyl-1H-pyrazol-4-yl) acetate

To a solution of tert-butyl-3-acetyl-4-oxopentanoate (1.0 g, 4.67 mmol) in methanol (15 mL), hydrazine hydrate 80% solution (0.363 mL, 7 mmol) was added and the resulting reaction mixture was stirred at 25° C. for 3 h. The reaction mixture was concentrated under reduced pressure to obtain tert-butyl-2-(3,5-dimethyl-1H-pyrazol-4-yl)acetate (0.89 g, 4.23 mmol, 91% yield) as a colorless oil.

Step-3: tert-Butyl-2-(1-(4-cyanophenyl)-3,5-dimethyl-1H-pyrazol-4-yl)acetate To a solution of tert-butyl 2-(3,5-dimethyl-1H-pyrazol-4-yl)acetate (8.5 g, 40.4 mmol) in N,N-dimethylformamide (25 mL), cesium carbonate (14.37 g, 44.1 mmol) was added and stirred at 25° C. for 1 h. 4-fluorobenzonitrile (4.45 g, 36.7 mmol) was added and the resulting reaction mixture was stirred at 100° C. for 8 h. The reaction mixture was diluted with water and extracted twice with dichloromethane (50 mL). The combined dichloromethane layer was then washed with brine solution (50 mL), dried over anhydrous sodium sulfate and concentrated under reduced pressure. The obtained crude residue was purified by flash column chromatography on silica gel by eluent 30% of ethyl acetate in hexane to obtain tert-butyl-2-(1-(4-cyanophenyl)-3,5-dimethyl-1H-pyrazol-4-yl)acetate (7.5 g, 66% yield).

Step-4: tert-Butyl-2-(1-(4-(N'-hydroxycarbamimidoyl)phenyl)-3,5-dimethyl-1H-pyrazol-4-yl)acetate To a stirred solution of tert-butyl 2-(1-(4-cyanophenyl)-3,5-dimethyl-1H-pyrazol-4-yl)acetate (1 g, 3.21 mmol) in ethanol (15 mL), hydroxylamine solution 50 wt. % in water (0.743 mL, 11.2 mmol) was added at 25° C. and stirred at 60° C. for 3 h. The resulting reaction mixture was directly concentrated under reduced pressure to obtain of tert-butyl-2-(1-(4-(N'-hydroxycarbamimidoyl)phenyl)-3,5-dimethyl-1H-pyrazol-4-yl)acetate (1.08 g, 98% yield).

Step-5: tert-Butyl-2-(3,5-dimethyl-1-(4-(5-(trifluoromethyl)-1,2,4-oxadiazol-3-yl)phenyl)-1H-pyrazol-4-yl)acetate (compound no 44)

To a stirred solution of tert-butyl 2-(1-(4-(N'-hydroxycarbamimidoyl)phenyl)-3,5-dimethyl-1H-pyrazol-4-yl)acetate (1.1 g, 3.19 mmol) in tetrahydrofuran (15 mL), trifluoroacetic anhydride (0.812 mL, 5.7 mmol) was added slowly at 0-5° C. under nitrogen atmosphere and stirred for 18 h at 25° C. The resulting reaction mixture was suspended in 50 mL of ethyl acetate and washed with aqueous sodium bicarbonate solution (30 mL). The ethyl acetate layer was isolated, dried over anhydrous sodium sulfate and concentrated under reduced pressure. The crude residue was purified by flash column chromatography on silica gel using eluent 5% of ethyl acetate in hexane to obtain tert-butyl-2-(3,5-dimethyl-1-(4-(5-(trifluoromethyl)-1,2,4-oxadiazol-3-yl)phenyl)-1H-pyrazol-4-yl)acetate (1.302 g, 3.08 mmol, 97% yield).

Step-6: 2-(3,5-Dimethyl-1-(4-(5-(trifluoromethyl)-1,2,4-oxadiazol-3-yl)phenyl)-1H-pyrazol-4-yl)acetic acid To a stirred solution of tert-butyl-2-(3,5-dimethyl-1-(4-(5-(trifluoromethyl)-1,2,4-oxadiazol-3-yl)phenyl)-1H-pyrazol-4-yl)acetate (0.2 g, 0.5 mmol) in tetrahydrofuran (10 mL) and water (3 mL), concentrated hydrochloric acid (2 mL) was added slowly at 0-5° C. and stirred for 8 h at 60° C. The mixture was concentrated to half its volume, neutralized with saturated aqueous sodium bicarbonate solution to pH 8-9, and extracted with ethyl acetate (20 mL). The ethyl acetate layer was washed with water (20 mL). The combined aqueous layer was acidified to pH 3 with 10% aqueous hydrochloric acid solution and extracted with ethyl acetate (30 mL). The combined ethyl acetate layer was dried over anhydrous sodium sulfate and concentrated under reduced pressure to obtain 2-(3,5-dimethyl-1-(4-(5-(trifluoromethyl)-1,2,4-oxadiazol-3-yl)phenyl)-1H-pyrazol-4-yl) acetic acid (0.135 g, 78% yield). $^1$H-NMR (400 MHz, DMSO-d6) δ 12.31 (s, 1H), 8.16 (d, 2H), 7.77 (d, 2H), 3.38 (d, 2H), 2.31 (d, 3H), 2.14 (d, 3H); LCMS (M+H): 367.

Step-7: 2-(3,5-Dimethyl-1-(4-(5-(trifluoromethyl)-1,2,4-oxadiazol-3-yl)phenyl)-1H-pyrazol-4-yl)-N-phenylacetamide To a solution of 2-(3,5-dimethyl-1-(4-(5-(trifluoromethyl)-1,2,4-oxadiazol-3-yl)phenyl)-1H-pyrazol-4-yl)acetic acid (0.25 g, 0.7 mmol) in dichloromethane (10 mL), N,N-dimethylaminopyridine (0.183 g, 1.5 mmol), N-(3-dimethylaminopropyl)-N'-ethylcarbodiimide hydrochloride (0.288 g, 1.5 mmol) and aniline (0.076 g, 0.8 mmol) were added at 0-5° C. under nitrogen atmosphere. The resulting reaction mixture was stirred at 25° C. for 18 h. The reaction mixture was diluted in dichloromethane (20 mL), washed twice with water (30 mL), dried over anhydrous sodium sulfate and concentrated under reduced pressure. The crude product was purified by prep-HPLC to obtain pure 2-(3,5-dimethyl-1-(4-(5-(trifluoromethyl)-1,2,4-oxadiazol-3-yl) phenyl)-1H-pyrazol-4-yl)-N-phenylacetamide (0.097 g, 32% yield). $^1$H-NMR (400 MHz, DMSO-d6) δ 10.08 (s, 1H), 8.16 (dt, 2H), 7.80-7.76 (m, 2H), 7.59 (dd, 2H), 7.31-7.27 (m, 2H), 7.05-7.01 (m, 1H), 3.50 (s, 2H), 2.38 (d, 3H), 2.21 (s, 3H); LCMS (M+H): 442.15.

The following compounds in table 14 were prepared by using the analogous procedure as described in example 14.

TABLE 14

| Compd no. | IUPAC name | Analytical data | Yield |
|---|---|---|---|
| 98 | N-(4-Chlorophenyl)-2-(3,5-dimethyl-1-(4-(5-(trifluoromethyl)-1,2,4-oxadiazol-3-yl)phenyl)-1H-pyrazol-4-yl)acetamide | $^1$H-NMR (400 MHz, DMSO-d6) δ 10.22 (s, 1H), 8.16 (dd, 2H), 7.78 (dd, 2H), 7.63 (dd, 2H), 7.35 (dd, 2H), 3.51 (s, 2H), 2.38 (s, 3H), 2.20 (s, 3H); LCMS (M + H): 476. | 0.189 g, 58% |
| 99 | 2-(3,5-Dimethyl-1-(4-(5-(trifluoromethyl)-1,2,4-oxadiazol-3-yl)phenyl)-1H-pyrazol-4-yl)-N-(4-fluoro-2-methoxyphenyl)acetamide | $^1$H-NMR (400 MHz, DMSO-d6) δ 9.16 (s, 1H), 8.14 (dt, 2H), 7.81-7.74 (m, 3H), 6.94 (dd, 1H), 6.68 (td, 1H), 3.81 (s, 3H), 3.54 (s, 2H), 2.36 (s, 3H), 2.18 (s, 3H); LCMS (M + H): 490.05. | 0.162 g, 49% |
| 100 | 2-(3,5-Dimethyl-1-(4-(5-(trifluoromethyl)-1,2,4-oxadiazol-3-yl)phenyl)-1H-pyrazol-4-yl)-N-(pyridin-2-yl)acetamide | $^1$H-NMR (400 MHz, DMSO-d6) δ 10.64 (s, 1H), 8.32 (dq, 1H), 8.16 (dd, 2H), 8.06 (d, 1H), 7.80-7.73 (m, 3H), 7.09 (ddd, 1H), 3.60 (s, 2H), 2.38 (s, 3H), 2.20 (s, 3H); LCMS (M + H): 443.05. | 0.137 g, 45% |
| 101 | 2-(3,5-Dimethyl-1-(4-(5-(trifluoromethyl)-1,2,4-oxadiazol-3-yl)phenyl)-1H-pyrazol-4-yl)-N-(thiazol-2-yl)acetamide | $^1$H-NMR (400 MHz, DMSO-d6) δ 12.31 (s, 1H), 8.17-8.14 (m, 2H), 7.80-7.77 (m, 2H), 7.47 (d, 1H), 7.20 (d, 1H), 3.64 (s, 2H), 2.38 (s, 3H), 2.19 (s, 3H); LCMS (M + H): 449. | 0.158 g, 52% |
| 102 | N-(4-Chloro-3-fluorophenyl)-2-(3,5-dimethyl-1-(4-(5-(trifluoromethyl)-1,2,4-oxadiazol-3-yl)phenyl)-1H-pyrazol-4-yl)acetamide | $^1$H-NMR (400 MHz, DMSO-d6) δ 10.42 (s, 1H), 8.16 (dt, 2H), 7.81-7.76 (m, 3H), 7.51 (t, 1H), 7.35 (dq, 1H), 3.53 (s, 2H), 2.37 (s, 3H), 2.19 (s, 3H); LCMS (M + H): 494. | 0.114 g, 34% |
| 103 | N-(4-Chlorobenzyl)-2-(3,5-dimethyl-1-(4-(5-(trifluoromethyl)-1,2,4-oxadiazol-3-yl)phenyl)-1H-pyrazol-4-yl)acetamide | $^1$H-NMR (400 MHz, DMSO-d6) δ 8.44 (t, 1H), 8.16 (dt, 2H), 7.77 (dt, 2H), 7.38 (dt, 2H), 7.26 (d, 2H), 4.25 (d, 2H), 3.32 (s, 2H), 2.34 (s, 3H), 2.17 (s, 3H); LCMS (M + H): 490.05. | 0.175 g, 52% |

TABLE 14-continued

| Compd no. | IUPAC name | Analytical data | Yield |
|---|---|---|---|
| 123 | 2-(3,5-dimethyl-1-(4-(5-(trifluoromethyl)-1,2,4-oxadiazol-3-yl)phenyl)-1H-pyrazol-4-yl)-N-(2-methoxyethyl)acetamide | $^1$H-NMR (400 MHz, DMSO-d6) δ 8.16 (dt, 2H), 7.99 (t, 1H), 7.76 (dt, 2H), 3.34 (t, 2H), 3.25-3.19 (m, 7H), 2.33 (d, 3H), 2.15 (d, 3H); LCMS (M + H): 424.40. | 0.139 g, 48% |
| 124 | N-(cyclopropylmethyl)-2-(3,5-dimethyl-1-(4-(5-(trifluoromethyl)-1,2,4-oxadiazol-3-yl)phenyl)-1H-pyrazol-4-yl)acetamide | $^1$H-NMR (400 MHz, DMSO-d6) δ 8.15 (dt, 2H), 7.99 (t, 1H), 7.77 (dt, 2H), 3.24 (s, 2H), 2.94 (t, 2H), 2.34-2.32 (m, 3H), 2.17-2.14 (m, 3H), 0.94-0.86 (m, 1H), 0.42-0.37 (m, 2H), 0.14 (td, 2H); LCMS (M + H): 420.15 | 0.135 g, 47% |
| 125 | N-cyclopropyl-2-(3,5-dimethyl-1-(4-(5-(trifluoromethyl)-1,2,4-oxadiazol-3-yl)phenyl)-1H-pyrazol-4-yl)acetamide | $^1$H-NMR (400 MHz, DMSO-d6) δ 8.15 (dt, 2H), 8.03 (d, 1H), 7.79-7.75 (m, 2H), 3.18 (s, 2H), 2.61 (qd, 1H), 2.32 (t, 3H), 2.14 (d, 3H), 0.60 (td, 2H), 0.42-0.38 (m, 2H); LCMS (M + H): 406.35. | 0.173 g, 63% |

Example 15: Preparation of 3-(4-(4-(((4-fluorophenyl)sulfinyl)methyl)-1H-imidazol-1-yl)phenyl)-5-(trifluoromethyl)-1,2,4-oxadiazole (compound no 126)

To a stirred solution of 3-(4-(4-(((4-fluorophenyl)thio)methyl)-1H-imidazol-1-yl)phenyl)-5-(trifluoromethyl)-1,2,4-oxadiazole (300 mg, 0.7 mmol) in methanol (5 μl), oxone (263 mg, 0.4 mmol) was added at 0° C. and stirred for 16 h. After completion of the reaction, the reaction mixture was concentrated, quenched with water (20 mL) and extracted the mixture thrice with ethyl acetate (10 mL). The combined ethyl acetate layer was washed with brine solution (10 mL), dried over anhydrous sodium sulphate and evaporated to obtain crude compound. The crude compound was purified by prep HPLC to afford 3-(4-(4-(((4-fluorophenyl)sulfinyl)methyl)-1H-imidazol-1-yl)phenyl)-5-(trifluoromethyl)-1,2,4-oxadiazole (137 mg, 0.314 mmol, 44% yield). $^1$H-NMR (400 MHz, DMSO-d6) δ 8.41 (d, 1H), 8.18 (dt, 2H), 7.86-7.90 (m, 2H), 7.68 (d, 1H), 7.53-7.62 (m, 5H), 4.13-4.17 (m, 1H), 4.06 (d, 1H); LCMS (M+H)—418.90.

The following compounds in table 15 were prepared by using the analogous procedure as described in example 15.

TABLE 15

| Compd no. | IUPAC name | Analytical data | Yield |
|---|---|---|---|
| 127 | 3-(4-(4-((phenylsulfinyl)methyl)-1H-imidazol-1-yl)phenyl)-5-(trifluoromethyl)-1,2,4-oxadiazole | $^1$H-NMR (400 MHz, DMSO-d6) δ 8.41 (d, 1H), 8.18 (dt, 2H), 7.86-7.90 (m, 2H), 7.68 (d, 1H), 7.53-7.62 (m, 5H), 4.13-4.17 (m, 1H), 4.06 (d, 1H); LCMS (M + H) − 418.90 | 96 mg, 31% |

Example 16: (2-fluorophenyl)(methyl)(((1-(4-(5-(trifluoromethyl)-1,2,4-oxadiazol-3-yl)phenyl)-1H-pyrazol-4-yl)methyl)imino)-λ$^6$-sulfanone (Compound no 128)

Step-1: 4-(4-(chloromethyl)-1H-pyrazol-1-yl)benzonitrile

To a stirred solution of 4-(4-(hydroxymethyl)-1H-pyrazol-1-yl)benzonitrile (2.5 g, 12.55 mmol) and chloroform (50 mL), thionyl chloride (1.191 ml, 16.31 mmol) were added at 0° C. The resulting reaction mixture was stirred at 68° C. for 4 h. After completion of the reaction, the reaction mixture was diluted with dichloromethane (50 mL) and washed with water (50 mL). The dichloromethane layer was dried over anhydrous sodium sulphate and concentrated under reduced pressure to obtain 4-(4-(chloromethyl)-1H-pyrazol-1-yl)benzonitrile (2.2 g, 81% yield).

Step-2: 4-(4-((((2-fluorophenyl)(methyl)(oxo)-λ$^6$-sulfaneylidene)amino)methyl)-1H-pyrazol-1-yl)benzonitrile To a stirred solution of (2-fluorophenyl)(imino)(methyl)-λ$^6$-sulfanone (0.239 g, 1.380 mmol) and dimethylformamide (5 mL), potassium tert-butoxide (0.178 g, 1.587 mmol) was added at 0° C. The resulting reaction mixture was stirred for 15 minute at 25° C., 4-(4-(chloromethyl)-1H-pyrazol-1-yl)benzonitrile (0.300 g, 1.380 mmol) was added portion wise at 0° C. The resulting reaction mixture was stirred for 2 h at 25° C. After completion of the reaction, the reaction mixture was diluted with ethyl acetate (50 mL) and washed with water (50 mL). The ethyl acetate layer was dried over anhydrous sodium sulphate and concentrated under reduced pressure. The crude residue was purified by column chromatography using 40% ethyl acetate in hexane as an eluent on silica gel obtain 4-(4-((((2-fluorophenyl)(methyl)(oxo)-λ$^6$-sulfaneylidene)amino)methyl)-1H-pyrazol-1-yl)benzonitrile (300 mg, 61% yield).

Step-3: 4-(4-((((2-fluorophenyl)(methyl)(oxo)-λ$^6$-sulfaneylidene)amino)methyl)-1H-pyrazol-1-yl)-N'-hydroxybenzimidamide To a stirred solution of 4-(4-((((2-fluorophenyl)(methyl)(oxo)-λ$^6$-sulfanylidene)amino)methyl)-1H-pyrazol-1-yl)benzonitrile (300 mg, 0.84 mmol) and ethanol (15 mL), 50% aq. Solution of hydroxylamine (0.10 ml, 0.84 mmol) were added at 0° C. The resulting reaction mixture was stirred at 65° C. for 12 h. After completion of the reaction, the reaction mixture was concentrated under reduced pressure to obtain 4-(4-((((2-fluorophenyl)(methyl)(oxo)-λ$^6$-sulfaneylidene) amino)methyl)-1H-pyrazol-1-yl)-N'-hydroxybenzimidamide (220 mg, 67% yield).

Step-4: (2-fluorophenyl)(methyl)(((1-(4-(5-(trifluoromethyl)-1,2,4-oxadiazol-3-yl)phenyl)-1H-pyrazol-4-yl)methyl)imino)-λ$^6$-sulfanone To a stirred solution of 4-(4-((((2-fluorophenyl)(methyl)(oxo)-λ$^6$-sulfaneylidene)amino)methyl)-1H-pyrazol-1-yl)-N'-hydroxybenzimidamide (220 mg, 0.568 mmol) in tetrahydrofuran (15 mL), trifluoroacetic anhydride (0.12 mL, 0.852 mmol) was added at 0° C. and stirred at 25 (C for 12 h. The reaction mixture was diluted with ethyl acetate (150 mL) and washed twice with sodium bicarbonate solution (40 mL). The organic layer was dried over anhydrous sodium sulphate and concentrated under reduced pressure. The crude residue was purified by column chromatography using 38% ethyl acetate in hexane as an eluent on silica gel to obtain (2-fluorophenyl)(methyl)(((1-(4-(5-(trifluoromethyl)-1,2,4-oxadiazol-3-yl)phenyl)-1H-pyrazol-4-yl) methyl)imino)-λ$^6$-sulfanone (188 mg, 71% yield).

The following compounds in table 16 were prepared by using the analogous procedure as described in example 16.

TABLE 16

| Compd no. | IUPAC name | Analytical data | Yield |
|---|---|---|---|
| 129 | (4-methoxyphenyl)(methyl)(((1-(4-(5-(trifluoromethyl)-1,2,4-oxadiazol-3-yl)phenyl)-1H-pyrazol-4-yl)methyl)imino)-λ$^6$-sulfanone | $^1$H-NMR (400 MHz, DMSO-d6) δ 8.40 (s, 1H), 8.15 (dd, 2H), 8.04 (dd, 2H), 7.82 (dd, 2H), 7.69 (s, 1H), 7.12-7.16 (m, 2H), 3.96 (d, 1H), 3.81-3.84 (m, 4H), 3.16 (s, 3H). LCMS (M + 1) 478.4 | 50 mg, 17% |
| 130 | methyl(thiazol-2-yl)(((1-(4-(5-(trifluoromethyl)-1,2,4-oxadiazol-3-yl)phenyl)-1H-pyrazol-4-yl)methyl)imino)-λ$^6$-sulfanone | $^1$H-NMR (400 MHz, DMSO-d6) δ 8.37 (s, 1H), 8.12-8.19 (m, 4H), 8.01 (dt, 2H), 7.63 (s, 1H), 4.11 (d, 1H), 3.98 (d, 1H), 3.41 (s, 3H). LCMS (M + 1) 454.95 | 95 mg, 32% |
| 131 | methyl(pyridin-4-yl)(((1-(4-(5-(trifluoromethyl)-1,2,4-oxadiazol-3-yl)phenyl)-1H-pyrazol-4-yl)methyl)imino)-λ$^6$-sulfanone | $^1$H-NMR (400 MHz, DMSO-d6) δ 8.86 (dd, 2H), 8.40 (s, 1H), 8.16 (t, 1H), 8.14 (t, 1H), 8.03 (t, 1H), 8.01 (t, 1H), 7.85 (dd, 2H), 7.67 (s, 1H), 4.00 (d, 1H), 3.84 (d, 1H), 3.30 (s, 3H). LCMS (M + 1) 448.95 | 50 mg, 19% |
| 132 | methyl(phenyl)(((1-(4-(5-(trifluoromethyl)-1,2,4-oxadiazol-3-yl)phenyl)-1H-pyrazol-4-yl)methyl)imino)-λ$^6$-sulfanone | $^1$H-NMR (400 MHz, DMSO-d6) δ 8.41 (s, 1H), 8.18-8.14 (m, 2H), 8.04 (dd, 2H), 7.94-7.90(m, 2H), 7.70-7.60 (m, 4H), 3.98 (d, 1H), 3.84 (d, 1H), 3.22 (s, 3H); LCMS: m/e 448 (M + 1) | 90 mg, 30% |

BIOLOGY EXAMPLES

As described herein the compounds of general formula (I) show fungicidal activities which are exerted with respect to numerous phytopathogenic fungi which attack on important agricultural crops.

The compounds of the present invention were assessed for their activity as described in the following tests:

In Vitro Tests

Example 1: *Pyricularia oryzae* (Rice Blast)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification, each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to the one of the untreated control. Compounds 3 24 28 40 43 at 300 ppm gave a minimum of 70% control in these tests when compared to the untreated check which showed extensive disease development.

Example 2: *Botrytis cinerea* (Gray Mold)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification, each plate was seeded with a 5 mm size mycelial disc taken from the periphery of an actively growing virulent culture plate. Plates were incubated in growth chambers at 22° C. temperature and 90% relative humidity for seven days and then the radial growth was measured and compared to the one of the untreated control. Compound 28 at 300 ppm gave a minimum of 70% control in these tests when compared to the untreated check which showed extensive disease development.

Example 3: *Alternaria solani* (Early Blight of Tomato/Potato)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification, each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to the one of the untreated control. Compounds 1 24 25 28 36 37 38 at 300 ppm gave a minimum of 70% control in these tests when compared to the untreated check which showed extensive disease development.

Example 4: *Fusarium culmorum* (Foot Rot of Cereals)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification, each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to the one of the untreated control. Compounds 28 at 300 ppm gave a minimum of 70% control in these tests when compared to the untreated check which showed extensive disease development.

Example 5: *Parastagonospora nodorum* (PARANO)

Potato dextrose (PDB) liquid medium (Difco) containing a PARANO ($10^5$ spores/ml) spore suspension was prepared. For the inhibition assay, each test compound was solved in dimethyl sulfoxide. 100 µl of the test media-solution was added to a 96-well microtiter plate, consequently, the same volume (100 µl) of spore suspension was added to the well making the final test concentrations and the plate was incubated at 18° C. for 15-18 days. The growth inhibition was evaluated by measuring the OD600.

Percent inhibition was calculated with the below formula:

$$I=(C-B)-(T-B)/(C-B)*100$$

Where T=treatment, C=control, and B=blank

Compounds 3 6 15 16 17 24 28 29 30 43 at 300 ppm gave a minimum of 70% control in these tests when compared to the untreated check which showed extensive disease development.

Green House Test

Example 1: *Phakopsora pachyrhizi* Test in Soybean

Compounds were dissolved in 2% dimethyl sulfoxide/acetone and then mixed with water containing emulsifier to the calibrated spray volume of 50 mL. Each spray solution was poured into a spray bottle for further application.

To test the preventive activity of the compound, healthy young Soybean plants, raised in the greenhouse, were sprayed with the active compound preparation at the stated application rate inside the spray cabinets using hollow cone nozzles. One day aftertreatment, the plants were inoculated with a conidial suspension containing $2\times10^5$*Phakopsora pachyrhiziinoculum*. The inoculated plants were then kept in a greenhouse chamber at 22-24° C. temperature and 80-90% relative humidity for disease expression.

A visual assessment of the compound's performance was carried out by rating the disease severity (0-100% scale) on treated plants 3, 7, 10 and 15 days after application. Efficacy (% control) of the compound was calculated by comparing the disease rating in the treatment with the one of the untreated control. The sprayed plants were also assessed for plant damage by recording symptoms like necrosis, chlorosis and stunting. Compounds 1 2 3 4 5 6 7 8 9 10 11 12 13 14 15 16 17 18 19 20 21 22 23 25 27 29 30 showed≤70% at 500 ppm control in these at 500 ppm control in these tests when compared to the untreated check which showed extensive disease development.

The invention claimed is:

1. A compound formula (I),

Formula (I)

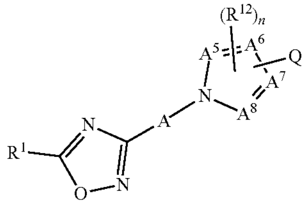

wherein, $R^1$ is $C_1$-$C_2$-haloalkyl;

A is $A^a$

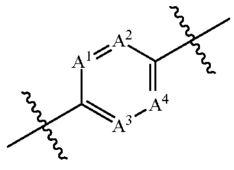

or $A^b$

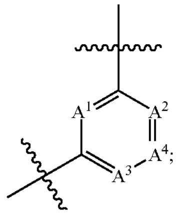

$A^1$, $A^2$, $A^3$ and $A^4$ are independently selected from $CR^9$ or N;

$A^5$, $A^6$, $A^7$ and $A^8$are independently selected from C or N; provided that at least one of $A^5$, $A^6$, $A^7$ and $A^8$ is C;

$R^9$ and $R^{12}$ are independently selected from the group consisting of hydrogen, halogen, nitro, cyano, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ thioalkyl and $C_3$-$C_6$ cycloalkoxy;

two $R^9$ each attached to adjacent C atoms, together with said C atoms, may form a 5- to 6-membered aromatic and non aromatic carbocyclic ring;

Q is selected from the group consisting of $Q_1$ to $Q_{12}$;

$Q_1$

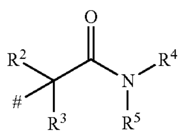

$Q_2$

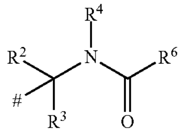

-continued

Q3

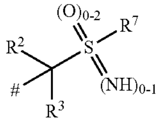

Q4

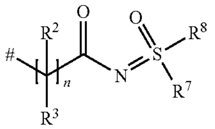

Q5

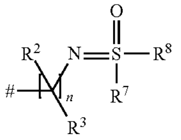

Q6

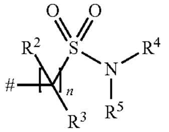

Q7

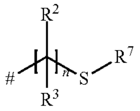

Q8

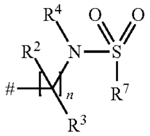

Q9

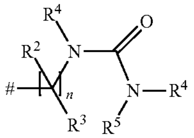

Q10

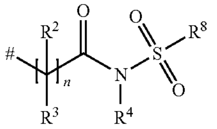

Q11

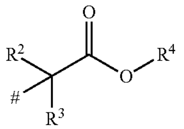

Q12

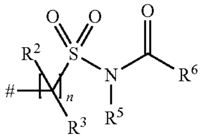

wherein, $R^2$ and $R^3$ are independently selected from the group consisting of hydrogen, halogen, $C_1$-$C_6$ alkyl, $C_1$-$C_6$ haloalkyl, $C_1$-$C_6$ alkoxy and $C_1$-$C_6$ haloalkoxy; or $R^2$ and $R^3$ together with the C atom to which they are attached may form a 3- to 6-membered nonaromatic carbocyclic ring or a 3- to 6-membered nonaromatic heterocyclic ring; wherein the hetero atom is selected from the group consisting of O, S or N; C atoms of said nonaromatic carbocyclic ring or said nonaromatic heterocyclic ring may be optionally substituted with C(═O) or C(═S); and said nonaromatic carbocyclic ring or said nonaromatic heterocyclic ring may be optionally substituted with halogen or $C_1$-$C_8$alkyl or $C_1$-$C_3$-alkoxy;

$R^4$, $R^5$, $R^6$, $R^7$, and $R^8$ are independently selected from the group consisting of hydrogen, halogen, $C_1$-$C_6$alkyl, $C_2$-$C_6$-alkenyl, $C_2$-$C_6$-alkynyl, $C_3$-$C_6$cycloalkyl, $C_1$-$C_6$ alkoxy, $C_1$-$C_6$ haloalkyl, $C_3$-$C_6$cycloalkyl-$C_1$-$C_6$alkyl, $C_1$-$C_6$alkoxy-$C_1$-$C_6$alkyl, $C_1$-$C_6$ alkoxycarbonyl, $C_1$-$C_6$ alkylsulfinyl, $C_1$-$C_6$ alkylsulfonyl, —$(CR^{10}R^{11})_{0-4}C_3$-$C_6$ non-aromatic carbocyclyl ring, —$(CR^{10}R^{11})_{0-4}C_6$-$C_{10}$ aromatic carbocyclyl ring, —$(CR^{10}R^{11})_{0-4}C_3$-$C_6$ non-aromatic heterocyclyl ring, —$(CR^{10}R^{11})_{0-4}C_6$-$C_{10}$ aromatic heterocyclyl ring, —$S(O)_{0-2}C_3$-$C_6$ non-aromatic carbocyclyl ring, —$S(O)_{0-2}C_6$-$C_{10}$ aromatic carbocyclyl ring, —$S(O)_{0-2}C_3$-$C_6$ non-aromatic heterocyclyl ring and —$S(O)_{0-2}C_6$-$C_{10}$ aromatic heterocyclyl ring; or $R^4$ and $R^5$, $R^8$ and $R^7$, $R^4$ and $R^6$, $R^5$ and $R^6$, $R^4$ and $R^7$ together with the atom to which they are attached may represent 4- to 8-membered nonaromatic heterocyclic ring; wherein the hetero atom is selected from the group consisting of O, $S(═O)_{0-2}$ or $NR^{13}$; C atom of said nonaromatic heterocyclic ring may be optionally substituted with C(═O) or C(═S);

$R^4$, $R^5$, $R^6$, $R^7$, and $R^8$ are optionally and independently may be substituted with halogen, cyano, amino, $C_1$-$C_6$ alkyl, $C_1$-$C_6$ alkoxy, $C_1$-$C_6$haloalkoxy, $C_1$-$C_6$ haloalkyl, $C_3$-$C_6$ cycloalkyl, $C_3$-$C_6$cycloalkyloxy; $C_1$-$C_6$ alkylamino, $C_1$-$C_6$ dialkylamino and $C_1$-$C_6$ trialkylamino;

$R^{10}$, $R^{11}$, and $R^{13}$ are independently selected from the group consisting of hydrogen, halogen, $C_1$-$C_6$ alkyl, $C_3$-$C_6$ cycloalkyl, $C_1$-$C_6$ haloalkyl and $C_1$-$C_6$ alkoxy;

n is an integer selected from 0, 1, 2 or 3;

or stereoisomers or agriculturally acceptable salts thereof.

2. The compound formula (I) according to claim 1, wherein $R^1$ is selected from the group consisting of —$CF_3$, —$CHF_2$ and —$CF_2Cl$;

A is phenyl or pyridyl;

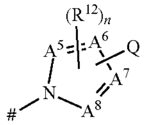

is selected from B1 to B5;

B1

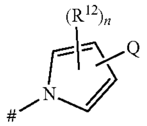

B2

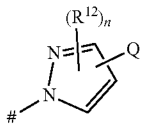

-continued

B3

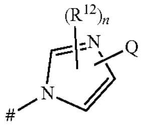

B4

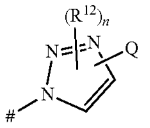

B5

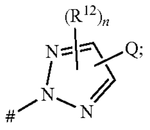

wherein, #represents attachment to A.

3. The compound of formula (I) according to claim 1, wherein said compound of formula (I) is selected from ethyl 2-(1-(4-(5-(trifluoromethyl)-1,2,4-oxadiazol-3-yl)phenyl)-1H-imidazol-4-yl)acetate, N-(4-methoxyphenyl)-2-(1-(4-(5-(trifluoromethyl)-1,2,4-oxadiazol-3-yl)phenyl)-1H-imidazol-4-yl)acetamide, 1-(pyrrolidin-1-yl)-2-(1-(4-(5-(trifluoromethyl)-1,2,4-oxadiazol-3-yl)phenyl)-1H-imidazol-4-yl) ethan-1-one, N-benzyl-2-(1-(4-(5-(trifluoromethyl)-1,2,4-oxadiazol-3-yl)phenyl)-1H-imidazol-4-yl)acetamide, N-(4-methoxybenzyl)-2-(1-(4-(5-(trifluoromethyl)-1,2,4-oxadiazol-3-yl)phenyl)-1H-imidazol-4-yl)acetamide, N-(4-fluorobenzyl)-2-(1-(4-(5-(trifluoromethyl)-1,2,4-oxadiazol-3-yl)phenyl)-1H-imidazol-4-yl)acetamide, N-(2-fluorobenzyl)-2-(1-(4-(5-(trifluoromethyl)-1,2,4-oxadiazol-3-yl)phenyl)-1H-imidazol-4-yl)acetamide, N-(p-tolyl)-2-(1-(4-(5-(trifluoromethyl)-1,2,4-oxadiazol-3-yl)phenyl)-1H-imidazol-4-yl)acetamide, N-(4-chlorophenyl)-2-(1-(4-(5-(trifluoromethyl)-1,2,4-oxadiazol-3-yl)phenyl)-1H-imidazol-4-yl)acetamide, N-(3-fluorophenyl)-2-(1-(4-(5-(trifluoromethyl)-1,2,4-oxadiazol-3-yl)phenyl)-1H-imidazol-4-yl)acetamide, 1-(piperidin-1-yl)-2-(1-(4-(5-(trifluoromethyl)-1,2,4-oxadiazol-3-yl)phenyl)-1H-imidazol-4-yl) ethan-1-one, N-(3-methoxyphenyl)-2-(1-(4-(5-(trifluoromethyl)-1,2,4-oxadiazol-3-yl)phenyl)-1H-imidazol-4-yl)acetamide, N-(pyridin-3-yl)-2-(1-(4-(5-(trifluoromethyl)-1,2,4-oxadiazol-3-yl)phenyl)-1H-imidazol-4-yl)acetamide, N-(2-bromophenyl)-2-(1-(4-(5-(trifluoromethyl)-1,2,4-oxadiazol-3-yl)phenyl)-1H-imidazol-4-yl)acetamide, N-phenyl-2-(1-(4-(5-(trifluoromethyl)-1,2,4-oxadiazol-3-yl)phenyl)-1H-imidazol-4-yl)acetamide, N-(5-methoxy-2-methylphenyl)-2-(1-(4-(5-(trifluoromethyl)-1,2,4-oxadiazol-3-yl)phenyl)-1H-imidazol-4-yl)acetamide, N-(4-fluoro-2-methoxyphenyl)-2-(1-(4-(5-(trifluoromethyl)-1,2,4-oxadiazol-3-yl)phenyl)-1H-imidazol-4-yl)acetamide, N-(4-oxido-1,4-) 6-oxathian-4-ylidene)-1-(4-(5-(trifluoromethyl)-1,2,4-oxadiazol-3-yl)phenyl)-1H-pyrazole-4-carboxamide, N-(methyl(oxo)(o-tolyl)-$\lambda^6$-sulfaneylidene)-1-(4-(5-(trifluoromethyl)-1,2,4-oxadiazol-3-yl)phenyl)-1H-pyrazole-4-carboxamide, N-((2-methoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-((4-methoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-(methyl(oxo)(phenyl)-$\lambda^6$-sulfaneylidene)-1-(4-(5-(trifluoromethyl)-1,2,4-oxadiazol-3-yl)phenyl)-1H-pyrazole-4-carboxamide, N-((3-fluorophenyl)(methyl)(oxo)-$\lambda^6$-sulfanylidene)-1-(4-(5-(trifluoromethyl)-1,2,4-oxadiazol-3-yl)phenyl)-1H-pyrazole-4-carboxamide, N-(methyl(oxo)(m-tolyl)-$\lambda^6$-sulfanylidene)-1-(4-(5-(trifluoromethyl)-1,2,4-oxadiazol-3-yl)phenyl)-1H-pyrrole-3-carboxamide, N-((2-methoxyethyl)(oxo)(pyridin-2-yl)-$\lambda^6$-sulfanylidene)-1-(4-(5-(trifluoromethyl)-1,2,4-oxadiazol-3-yl)phenyl)-1H-pyrrole-3-carboxamide, N-(methyl(oxo)(5-(trifluoromethyl)pyridin-2-yl)-$\lambda^6$-sulfanylidene)-1-(4-(5-(trifluoromethyl)-1,2,4-oxadiazol-3-yl)phenyl)-1H-pyrrole-3-carboxamide, N-((4-fluorophenyl)(methyl)(oxo)-$\lambda^6$-sulfanylidene)-1-(4-(5-(trifluoromethyl)-1,2,4-oxadiazol-3-yl)phenyl)-1H-pyrrole-3-carboxamid, N-((3-fluoropyridin-4-yl)(methyl)(oxo)-6-sulfanylidene)-1-(4-(5-(trifluoromethyl)-1,2,4-oxadiazol-3-yl)phenyl)-1H-pyrrole-3-carboxamid, N-((4-methoxypyridin-2-yl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide, N-(dimethyl(oxo)-$\lambda^6$-sulfanylidene)-1-(4-(5-(trifluoromethyl)-1,2,4-oxadiazol-3-yl)phenyl)-1H-pyrrole-3-carboxamide, N-((4-methoxyphenyl)(methyl)(oxo)-$\lambda^6$-sulfanylidene)-1-(4-(5-(trifluoromethyl)-1,2,4-oxadiazol-3-yl)phenyl)-1H-pyrrole-3-carboxamide, N-((2,4-dimethoxyphenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-((2,6-dichlorophenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-(methyl(oxo)(pyridin-4-yl)-$\lambda^6$-sulfaneylidene)-1-(4-(5-(trifluoromethyl)-1,2,4-oxadiazol-3-yl)phenyl)-1H-pyrazole-4-carboxamide, N-((2-methoxyethyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-(diethyl (oxo)-$\lambda^6$-sulfaneylidene)-1-(4-(5-(trifluoromethyl)-1,2,4-oxadiazol-3-yl)phenyl)-1H-pyrazole-4-carboxamide, N-(dimethyl (oxo)-$\lambda^6$-sulfaneylidene)-1-(4-(5-(trifluoromethyl)-1,2,4-oxadiazol-3-yl)phenyl)-1H-pyrazole-4-carboxamide, N-((4-chlorophenyl)(methyl)(oxo)-$\lambda^6$-sulfaneylidene)-1-(4-(5-(trifluoromethyl)-1,2,4-oxadiazol-3-yl)phenyl)-1H-pyrazole-4-carboxamide, N-((3-bromophenyl) (isopropyl)(oxo)-$\lambda^6$-sulfanylidene)-1-(4-(5-(trifluoromethyl)-1,2,4-oxadiazol-3-yl)phenyl)-1H-pyrrole-3-carboxamide, N-(methyl(oxo)(thiazol-2-yl)-$\lambda^6$-sulfanylidene)-1-(4-(5-(trifluoromethyl)-1,2,4-oxadiazol-3-yl)phenyl)-1H-pyrrole-3-carboxamide, 3-(4-(4-(piperidin-1-ylsulfonyl)-1H-pyrazol-1-yl)phenyl)-5-(trifluoromethyl)-1,2,4-oxadiazole, 3-(4-(4-((phenylthio)methyl)-1H-imidazol-1-yl)phenyl)-5-(trifluoromethyl)-1,2,4-oxadiazole, tert-Butyl-2-(3,5-dimethyl-1-(4-(5-(trifluoromethyl)-1,2,4-oxadiazol-3-yl)phenyl)-1H-pyrazol-4-yl)acetate, N-(4-fluorophenyl)-1-(4-(5-(trifluoromethyl)-1,2,4-oxadiazol-3-yl)phenyl)-1H-pyrazole-4-sulfonamide, N-ethyl-1-(4-(5-(trifluoromethyl)-1,2,4-oxadiazol-3-yl)phenyl)-1H-pyrazole-4-sulfonamide, N-(2,4-difluorophenyl)-N-methyl-1-(4-(5-(trifluoromethyl)-1,2,4-oxadiazol-3-yl)phenyl)-1H-pyrazole-4-sulfonamide, N-(2-fluorophenyl)-N-methyl-1-(4-(5-(trifluoromethyl)-1,2,4-oxadiazol-3-yl)phenyl)-1H-pyrazole-4-sulfonamide, 3-(4-(4-(azetidin-1-ylsulfonyl)-1H-pyrazol-1-yl)phenyl)-5-(trifluoromethyl)-1,2,4-oxadiazole, N-methyl-N-phenyl-1-(4-(5-(trifluoromethyl)-1,2,4-oxadiazol-3-yl)phenyl)-1H-pyrazole-4-sulfonamide, N-(3-methoxyphenyl)-N-methyl-1-(4-(5-(trifluoromethyl)-1,2,4-oxadiazol-3-yl)phenyl)-1H-pyrazole-4-sulfonamide, N-methyl-N-(p-tolyl)-1-(4-(5-(trifluoromethyl)-1,2,4-oxadiazol-3-yl)phenyl)-1H-pyrazole-4-sulfonamide, N-(3-fluorophenyl)-N-methyl-1-(4-(5-(trifluoromethyl)-1,2,4-oxadiazol-3-yl)phenyl)-1H-pyrazole-4-sulfonamide, N-(3-chlorophenyl)-N-methyl-1-(4-(5-(trifluoromethyl)-1,2,4-oxadiazol-3-yl)phenyl)-1H-pyrazole-4-sulfonamide, 3-(4-(4-((3-fluoropyrrolidin-1-yl) sulfonyl)-1H-pyrazol-1-yl) phenyl)-5-(trifluoromethyl)-1,2,4-oxadiazole, N-methyl-N-(pyridin-2-yl)-1-(4-(5-(trifluoromethyl)-1,2,4-oxadiazol-3-yl)phenyl)-1H-pyrazole-4-sulfonamide, 4-((1-(4-(5-(trifluoromethyl)-1,2,4-oxadiazol-3-yl)phenyl)-1H-pyrazol-4-yl) sulfonyl) morpholine, N-cyclopropyl-1-(4-(5-(trifluoromethyl)-1,2,4-oxadiazol-3-yl)phenyl)-1H-pyrazole-4-sulfonamide, N-benzyl-1-(4-(5-(trifluoromethyl)-1,2,4-oxadiazol-3-yl)phenyl)-1H-pyrazole-4-sulfonamide, 3-(4-(4-(((4-methoxyphenyl)thio) methyl)-1H-imidazol-1-yl)phenyl)-5-(trifluoromethyl)-1,2,4-oxadiazole, 3-(4-(4-((isopropylthio)methyl)-1H-imidazol-1-yl)phenyl)-5-(trifluoromethyl)-1,2,4-oxadiazole, 3-(4-(4-(((2-fluorophenyl)thio)methyl)-1H-imidazol-1-yl)phenyl)-5-(trifluoromethyl)-1,2,4-oxadiazole, 3-(4-(4-(((4-fluorophenyl)thio) methyl)-1H-imidazol-1-yl)phenyl)-5-(trifluoromethyl)-1,2,4-oxadiazole, 3-(4-(4-(((3-chlorophenyl)thio)methyl)-1H-imidazol-1-yl)phenyl)-5-(trifluoromethyl)-1,2,4-oxadiazole, 3-(4-(4-(((4-methoxybenzyl)thio)methyl)-1H-imidazol-1-yl)phenyl)-5-(trifluoromethyl)-1,2,4-oxadiazole, 3-(4-(4-((pyridin-2-ylthio)methyl)-1H-imidazol-1-yl)phenyl)-5-(trifluoromethyl)-1,2,4-oxadiazole, 3-(4-(4-((phenylsulfonyl)methyl)-1H-imidazol-1-yl)phenyl)-5-(trifluoromethyl)-1,2,4-oxadiazole, 3-(4-(4-(((4-methoxyphenyl) sulfonyl)methyl)-1H-imidazol-1-yl) phenyl)-5-(trifluoromethyl)-1,2,4-oxadiazole, 3-(4-(4-((isopropylsulfonyl)methyl)-1H-imidazol-1-yl)phenyl)-5-(trifluoromethyl)-1,2,4-oxadiazole, 3-(4-(4-(((2-fluorophenyl) sulfonyl)methyl)-1H-imidazol-1-yl)phenyl)-5-(trifluoromethyl)-1,2,4-oxadiazole, 3-(4-(4-(((4-fluorophenyl) sulfonyl)methyl)-1H-imidazol-1-yl)phenyl)-5-(trifluoromethyl)-1,2,4-oxadiazole, 3-(4-(4-(((3-chlorophenyl) sulfonyl)methyl)-1H-imidazol-1-yl)phenyl)-5-(trifluoromethyl)-1,2,4-oxadiazole, 3-(4-(4-(((4-methoxybenzyl) sulfonyl)methyl)-1H-imidazol-1-yl) phenyl)-5-(trifluoromethyl)-1,2,4-oxadiazole, 3-(4-(4-((pyridin-2-ylsulfonyl)methyl)-1H-imidazol-1-yl)phenyl)-5-(trifluoromethyl)-1,2,4-oxadiazole, imino (phenyl) ((1-(4-(5-(trifluoromethyl)-1,2,4-oxadiazol-3-yl)phenyl)-1H-imidazol-4-yl)methyl)-$\lambda^6$-sulfanone, (2 fluorophenyl) (imino)((1-(4-(5-(trifluoromethyl)-1,2,4-oxadiazol-3-yl) phenyl)-1H-imidazol-4-yl)methyl)-$\lambda^6$-sulfanone, 4-methyl-N-((1-(4-(5-(trifluoromethyl)-1,2,4-oxadiazol-3-yl)phenyl)-1H-imidazol-4-yl)methyl) benzenesulfonamide, N-((1-(4-(5-(trifluoromethyl)-1,2,4-oxadiazol-3-yl)phenyl)-1H-imidazol-4-yl)methyl) benzenesulfonamide, N-((1-(4-(5-(trifluoromethyl)-1,2,4-oxadiazol-3-yl)phenyl)-1H-imidazol-4-yl)methyl)acetamide, 4-fluoro-N-((1-(4-(5-(trifluoromethyl)-1,2,4-oxadiazol-3-yl)phenyl)-1H-imidazol-4-yl)methyl) benzenesulfonamide, N-((1-(4-(5-(trifluoromethyl)-1,2,4-oxadiazol-3-yl)phenyl)-1H-imidazol-4-yl)methyl) cyclopropanesulfonamide, 4-(trifluoromethyl)-N-((1-(4-(5-(trifluoromethyl)-1,2,4-oxadiazol-3-yl)phenyl)-1H-imidazol-4-yl)methyl) benzamide, N-((1-(4-(5-(trifluoromethyl)-1,2,4-oxadiazol-3-yl) phenyl)-1H-imidazol-4-yl)methyl) isobutyramide, N-((1-(4-(5-(trifluoromethyl)-1,2,4-oxadiazol-3-yl)phenyl)-1H-imidazol-4-yl)methyl) cyclobutanecarboxamide, N-((1-(4-(5-(trifluoromethyl)-1,2,4-oxadiazol-3-yl)phenyl)-1H-imidazol-4-yl)methyl) benzamide, 4-methoxy-N-((1-(4-(5-(trifluoromethyl)-1,2,4-oxadiazol-3-yl)phenyl)-1H-imidazol-4-yl)methyl) benzamide, 2-fluoro-N-((1-(4-(5-(trifluoromethyl)-1,2,4-oxadiazol-3-yl)phenyl)-1H-imidazol-4-yl)methyl) benzamide, N-((1-(4-(5-(trifluoromethyl)-1,2,4-oxadiazol-3-yl)phenyl)-1H-imidazol-4-yl)methyl) methanesulfonamide, N-((1-(4-(5-(trifluoromethyl)-1,2,4-oxadiazol-3-yl)phenyl)-1H-imidazol-4-yl)methyl) thiazole-2-carboxamide, 2-(3,5-dimethyl-1-(4-(5-(trifluoromethyl)-1,2,4-oxadiazol-3-yl) phenyl)-1H-pyrazol-4-yl)-N-phenylacetamide, N-(4-Chlorophenyl)-2-(3,5-dimethyl-1-(4-(5-(trifluoromethyl)-1,2,4-oxadiazol-3-yl)phenyl)-1H-pyrazol-4-yl)acetamide, 2-(3,5-Dimethyl-1-(4-(5-(trifluoromethyl)-1,2,4-oxadiazol-3-yl)phenyl)-1H-pyrazol-4-yl)-N-(4-fluoro-2-methoxyphenyl)acetamide, 2-(3,5-Dimethyl-1-(4-(5-(trifluoromethyl)-1,2,4-oxadiazol-3-yl)phenyl)-1H-pyrazol-4-yl)-N-(pyridin-2-yl)acetamide, 2-(3,5-Dimethyl-1-(4-(5-(trifluoromethyl)-1,2,4-oxadiazol-3-yl)phenyl)-1H-pyrazol-4-yl)-N-(thiazol-2-yl)acetamide, N-(4-Chloro-3-fluorophenyl)-2-(3,5-dimethyl-1-(4-(5-(trifluoromethyl)-1,2,4-oxadiazol-3-yl) phenyl)-1H-pyrazol-4-yl)acetamide, N-(4-Chlorobenzyl)-2-(3,5-dimethyl-1-(4-(5-(trifluoromethyl)-1,2,4-oxadiazol-3-yl)phenyl)-1H-pyrazol-4-yl)acetamide, 4-chloro-N-((1-(4-(5-(trifluoromethyl)-1,2,4-oxadiazol-3-yl)phenyl)-1H-pyrazol-4-yl)methyl) benzamide, N-((1-(4-(5-(trifluoromethyl)-1,2,4-oxadiazol-3-yl)phenyl)-1H-pyrazol-4-yl)methyl)acetamide, N-((1-(4-(5-(trifluoromethyl)-1,2,4-oxadiazol-3-yl)phenyl)-1H-pyrazol-4-yl)methyl) propionamide, 2-fluoro-N-((1-(4-(5-(trifluoromethyl)-1,2,4-oxadiazol-3-yl)phenyl)-1H-pyrazol-4-yl)methyl) benzamide, 4-fluoro-N-((1-(4-(5-(trifluoromethyl)-1,2,4-oxadiazol-3-yl)phenyl)-1H-pyrazol-4-yl)methyl) benzamide, 2-methyl-N-((1-(4-(5-(trifluoromethyl)-1,2,4-oxadiazol-3-yl)phenyl)-1H-pyrazol-4-yl)methyl) thiazole-5-carboxamide, N-((1-(4-(5-(trifluoromethyl)-1,2,4-oxadiazol-3-yl)phenyl)-1H-pyrazol-4-yl)methyl) cyclobutanecarboxamide, N-((1-(4-(5-(trifluoromethyl)-1,2,4-oxadiazol-3-yl)phenyl)-1H-pyrazol-4-yl)methyl) nicotinamide, N-((1-(4-(5-(trifluoromethyl)-1,2,4-oxadiazol-3-yl)phenyl)-1H-pyrazol-4-yl) methyl) methanesulfonamide, N-((1-(4-(5-(trifluoromethyl)-1,2,4-oxadiazol-3-yl)phenyl)-1H-pyrazol-4-yl)methyl) ethanesulfonamide, N-((1-(4-(5-(trifluoromethyl)-1,2,4-oxadiazol-3-yl)phenyl)-1H-pyrazol-4-yl)methyl) cyclopropanesulfonamide, 2-fluoro-N-((1-(4-(5-(trifluoromethyl)-1,2,4-oxadiazol-3-yl)phenyl)-1H-pyrazol-4-yl)methyl) benzenesulfonamide, 5-chloro-N-((1-(4-(5-(trifluoromethyl)-1,2,4-oxadiazol-3-yl)phenyl)-1H-pyrazol-4-yl)methyl) thiophene-2-sulfonamide, 4-fluoro-N-((1-(4-(5-(trifluoromethyl)-1,2,4-oxadiazol-3-yl)phenyl)-1H-pyrazol-4-yl)methyl) benzenesulfonamide, N-((1-(4-(5-(trifluoromethyl)-1,2,4-oxadiazol-3-yl)phenyl)-1H-pyrazol-4-yl)methyl) pyridine-3-sulfonamide, 1-(pyridin-3-yl)-3-((1-(4-(5-(trifluoromethyl)-1,2,4-oxadiazol-3-yl)phenyl)-1H-pyrazol-4-yl)methyl) urea, 1-(2-fluorophenyl)-3-((1-(4-(5-(trifluoromethyl)-1,2,4-oxadiazol-3-yl)phenyl)-1H-pyrazol-4-yl)methyl) urea, (4-fluorophenyl)(imino)((1-(4-(5-(trifluoromethyl)-1,2,4-oxadiazol-3-yl)phenyl)-1H-imidazol-4-yl)methyl)-$\lambda^6$-sulfanone, (3-chlorophenyl) (imino) ((1-(4-(5-(trifluoromethyl)-1,2,4-oxadiazol-3-yl) phenyl)-1H-imidazol-4-yl)methyl)-$\lambda^6$-sulfanone, 2-(3,5-dimethyl-1-(4-(5-(trifluoromethyl)-1,2,4-oxadiazol-3-yl) phenyl)-1H-pyrazol-4-yl)-N-(2-methoxyethyl)acetamide, N-(cyclopropylmethyl)-2-(3,5-dimethyl-1-(4-(5-(trifluoromethyl)-1,2,4-oxadiazol-3-yl)phenyl)-1H-pyrazol-4-yl) acetamide, N-cyclopropyl-2-(3,5-dimethyl-1-(4-(5-(trifluoromethyl)-1,2,4-oxadiazol-3-yl)phenyl)-1H-pyrazol-4-yl) acetamide, 3-(4-(4-(((4-fluorophenyl) sulfinyl)methyl)-1H-imidazol-1-yl)phenyl)-5-(trifluoromethyl)-1,2,4-oxadiazole, 3-(4-(4-((phenylsulfinyl)methyl)-1H-imidazol-1-yl)phenyl)-5-(trifluoromethyl)-1,2,4-oxadiazole, (2-fluorophenyl)

(methyl)(((1-(4-(5-(trifluoromethyl)-1,2,4-oxadiazol-3-yl) phenyl)-1H-pyrazol-4-yl)methyl) imino)-$\lambda^6$-sulfanone, (4-methoxyphenyl)(methyl)(((1-(4-(5-(trifluoromethyl)-1,2,4-oxadiazol-3-yl)phenyl)-1H-pyrazol-4-yl)methyl) imino)-$\lambda^6$-sulfanone, methyl (thiazol-2-yl) (((1-(4-(5-(trifluoromethyl)-1,2,4-oxadiazol-3-yl)phenyl)-1H-pyrazol-4-yl) methyl) imino)-$\lambda^6$-sulfanone, methyl (pyridin-4-yl) (((1-(4-(5-(trifluoromethyl)-1,2,4-oxadiazol-3-yl)phenyl)-1H-pyrazol-4-yl)methyl) imino)-6-sulfanone and methyl (phenyl) (((1-(4-(5-(trifluoromethyl)-1,2,4-oxadiazol-3-yl) phenyl)-1H-pyrazol-4-yl)methyl) imino)-$\lambda^6$-sulfanone.

4. A combination comprising the compound of formula (I) according to claim 1 and at least one further pesticidally active substance selected from the group consisting of fungicides, insecticides, nematicides, acaricides, biopesticides, herbicides, safeners, plant growth regulators, antibiotics, fertilizers and nutrients.

5. An agrochemical composition comprising the compound of formula (I) according to claim 1 and at least one agrochemically acceptable auxiliary.

6. The composition according to claim 5, wherein said composition further comprises at least one additional pesticidally active ingredient.

7. A method for controlling or preventing infestation of plants by phytopathogenic microorganisms in agricultural crops and/or horticultural crops wherein an effective amount of at least one compound of formula (I) as claimed in claim 1, is applied to the plants, to parts thereof or locus thereof.

* * * * *